United States Patent
Sekino et al.

(10) Patent No.: US 10,371,639 B2
(45) Date of Patent: Aug. 6, 2019

(54) DETECTING FLUORESCENT MATERIAL IN A STAINED PARTICLE BY COMPARISON WITH AN UNSTAINED PARTICLE OVER A PLURALITY OF FREQUENCY BANDS AND BY ESTIMATING A LINEAR COMBINATION OF BASE VECTORS

(71) Applicant: Sony Corporation, Tokyo (JP)

(72) Inventors: Masashi Sekino, Tokyo (JP); Yasunobu Kato, Kanagawa (JP); Tatsumi Ito, Kanagawa (JP)

(73) Assignee: Sony Corporation, Tokyo (JP)

( * ) Notice: Subject to any disclaimer, the term of this patent is extended or adjusted under 35 U.S.C. 154(b) by 82 days.

(21) Appl. No.: 13/897,875

(22) Filed: May 20, 2013

(65) Prior Publication Data
US 2013/0323825 A1    Dec. 5, 2013

(30) Foreign Application Priority Data

May 29, 2012    (JP) ................................ 2012-122161

(51) Int. Cl.
*G01N 21/64*    (2006.01)
*G01N 15/14*    (2006.01)
*G16B 99/00*    (2019.01)

(52) U.S. Cl.
CPC ..... *G01N 21/6486* (2013.01); *G01N 15/1429* (2013.01); *G01N 2015/1477* (2013.01); *G01N 2021/6441* (2013.01); *G16B 99/00* (2019.02)

(58) Field of Classification Search
None
See application file for complete search history.

(56) References Cited

FOREIGN PATENT DOCUMENTS

JP    2003-083894 A    3/2003

OTHER PUBLICATIONS

Farkas, "Multimode light microscopy and the dynamics of molecules, cells, and tissues," Ann. Rev. Physiol., vol. 55, pp. 785-817, 1993.*
Raub, "Image Correlation Spectroscopy of Multiphoton Images Correlates with Collagen Mechanical Properties," Biophys. J, vol. 94, pp. 2361-2373, 2008.*
Krutzik, "Fluorescent cell barcoding in flow cytometry allows high-throughput drug screening and signaling profiling," Nature methods, vol. 3.5, p. 361-368, 2006.*
Doroshenko, "Fluorescence Probing of Cell Membranes with Azacrown Substituted Ketocyanine Dyes," Journal of Fluorescence, vol. 12(3/4), p. 455-464, 2002.*

* cited by examiner

*Primary Examiner* — G Steven Vanni
(74) *Attorney, Agent, or Firm* — Wolf, Greenfield, & Sacks, P.C.

(57) ABSTRACT

Provided is an information processing apparatus, including a testing section performing statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band, a masking processing section setting, in a case where there is no significant difference between the simple staining data and the unstaining data for the frequency band, the simple staining data to 0 or a prescribed value, and an estimation section estimating, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

11 Claims, 37 Drawing Sheets

SYSTEM CONFIGURATION EXAMPLE

RESTRICTED LEAST SQUARE METHOD USING BEAD SIMPLE STAINING BASE VECTOR

RESTRICTED LEAST SQUARE METHOD USING CELL SIMPLE STAINING BASE VECTOR

PRESENT PROPOSED METHOD USING BEAD SIMPLE STAINING BASE VECTOR

FIG. 22
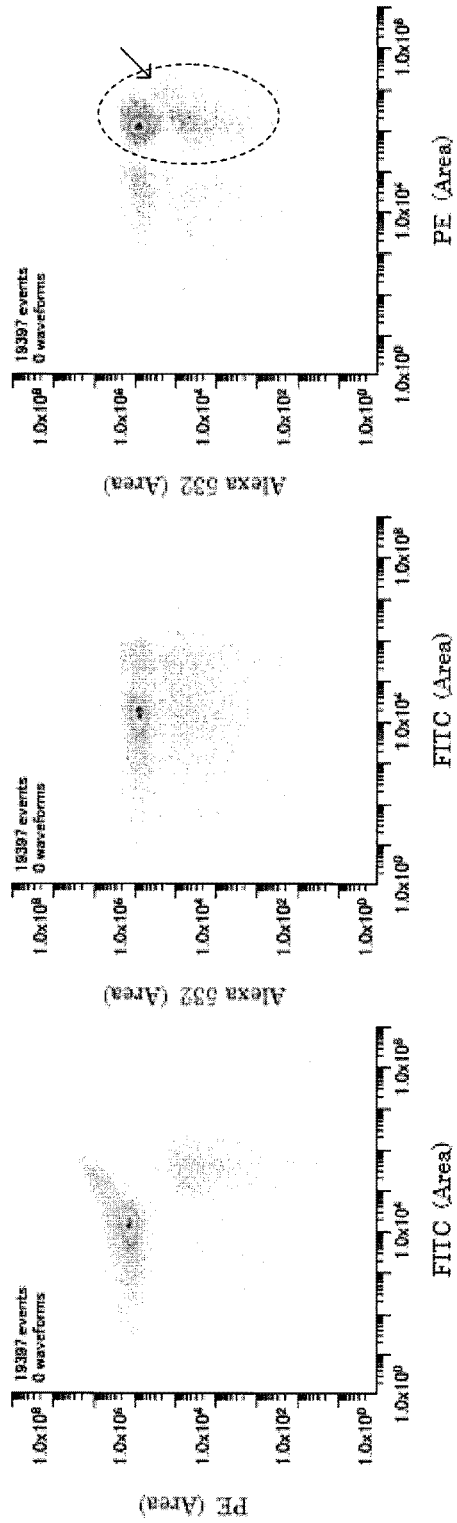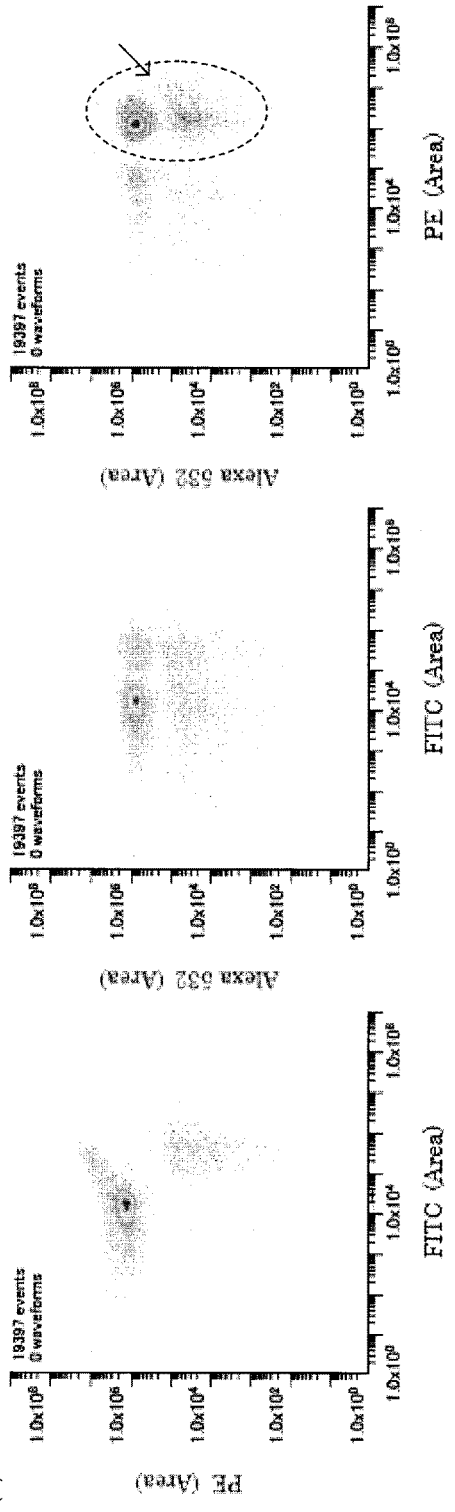

FIG. 25
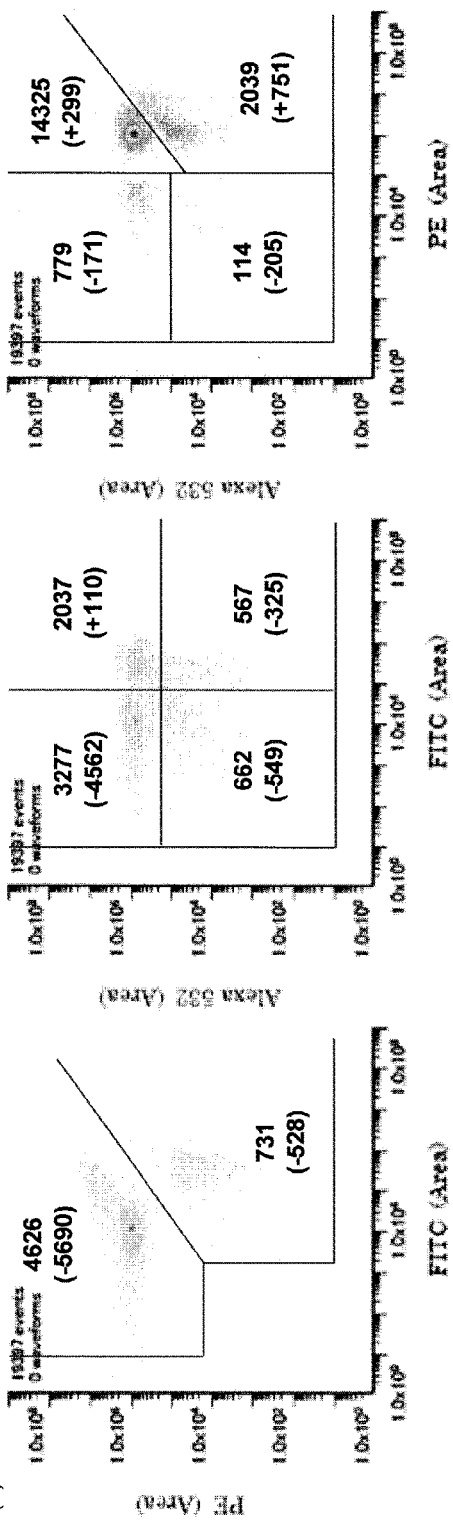
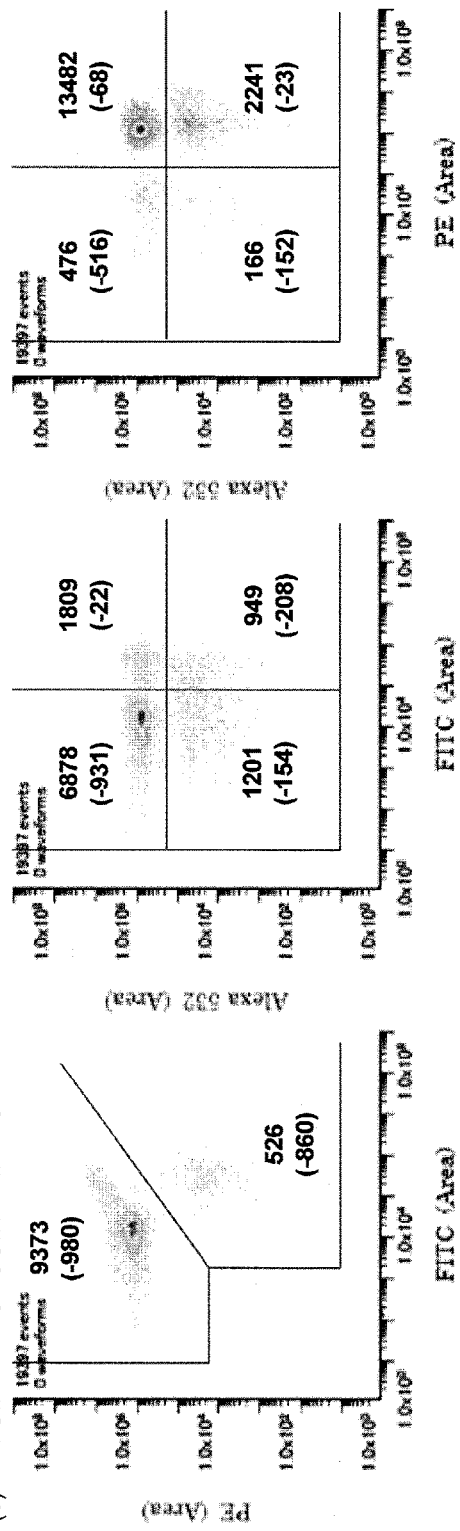

FIG. 29

(SETTING EXAMPLE OF MASKING: IN CASE OF NO MASKING)

| Laser | 488 nm | | | | | | | | | | | | | | | | | | | |
|---|---|---|---|---|---|---|---|---|---|---|---|---|---|---|---|---|---|---|---|---|
| Channel | 1 | 2 | 3 | 4 | 5 | 6 | 7 | 8 | 9 | 10 | 11 | 12 | 13 | 14 | 15 | 16 | 17 | 18 | 19 | 20 |
| FITC | 1 | 1 | 1 | 1 | 1 | 1 | 1 | 1 | 1 | 1 | 1 | 1 | 1 | 1 | 1 | 1 | 1 | 1 | 1 | 1 |
| PE-Cy7 | 1 | 1 | 1 | 1 | 1 | 1 | 1 | 1 | 1 | 1 | 1 | 1 | 1 | 1 | 1 | 1 | 1 | 1 | 1 | 1 |
| APC | 1 | 1 | 1 | 1 | 1 | 1 | 1 | 1 | 1 | 1 | 1 | 1 | 1 | 1 | 1 | 1 | 1 | 1 | 1 | 1 |

| 488 nm | | | | | | | | | | | | |
|---|---|---|---|---|---|---|---|---|---|---|---|---|
| 21 | 22 | 23 | 24 | 25 | 26 | 27 | 28 | 29 | 30 | 31 | 32 |
| 1 | 1 | 1 | 1 | 1 | 1 | 1 | 1 | 1 | 1 | 1 | 1 |
| 1 | 1 | 1 | 1 | 1 | 1 | 1 | 1 | 1 | 1 | 1 | 1 |
| 1 | 1 | 1 | 1 | 1 | 1 | 1 | 1 | 1 | 1 | 1 | 1 |

FIG. 30

(SETTING EXAMPLE OF MASKING: IN CASE OF NO MASKING)

| Laser | | 640 nm | | | | | | | | | | | | | | | | | | |
|---|---|---|---|---|---|---|---|---|---|---|---|---|---|---|---|---|---|---|---|---|
| Channel | 1 | 2 | 3 | 4 | 5 | 6 | 7 | 8 | 9 | 10 | 11 | 12 | 13 | 14 | 15 | 16 | 17 | 18 | 19 | 20 |
| FITC | 1 | 1 | 1 | 1 | 1 | 1 | 1 | 1 | 1 | 1 | 1 | 1 | 1 | 1 | 1 | 1 | 1 | 1 | 1 | 1 |
| PE-Cy7 | 1 | 1 | 1 | 1 | 1 | 1 | 1 | 1 | 1 | 1 | 1 | 1 | 1 | 1 | 1 | 1 | 1 | 1 | 1 | 1 |
| APC | 1 | 1 | 1 | 1 | 1 | 1 | 1 | 1 | 1 | 1 | 1 | 1 | 1 | 1 | 1 | 1 | 1 | 1 | 1 | 1 |

| 640 nm | | | | | | | | | | | |
|---|---|---|---|---|---|---|---|---|---|---|---|
| 21 | 22 | 23 | 24 | 25 | 26 | 27 | 28 | 29 | 30 | 31 | 32 |
| 1 | 1 | 1 | 1 | 1 | 1 | 1 | 1 | 1 | 1 | 1 | 1 |
| 1 | 1 | 1 | 1 | 1 | 1 | 1 | 1 | 1 | 1 | 1 | 1 |
| 1 | 1 | 1 | 1 | 1 | 1 | 1 | 1 | 1 | 1 | 1 | 1 |

FIG. 31

(MEAN WAVEFORM BY PERFORMING SIMPLE STAINING FOR EACH DYE: NO MASKING)

| Laser | | | | | 488 nm | | | | | |
|---|---|---|---|---|---|---|---|---|---|---|
| Channel | 1 | 2 | 3 | 4 | 5 | 6 | 7 | 8 | 9 | 10 |
| FITC | 0.2120 | 0.4411 | 0.7020 | 0.8959 | 0.8879 | 1 | 0.9629 | 0.8679 | 0.8010 | 0.6823 |
| PE-Cy7 | 0.0096 | 0.0125 | 0.0139 | 0.0148 | 0.0145 | 0.0155 | 0.0166 | 0.0166 | 0.0195 | 0.0219 |
| APC | 0.0247 | 0.0300 | 0.0337 | 0.0377 | 0.0393 | 0.0412 | 0.0425 | 0.0424 | 0.0463 | 0.0467 |
| unstained | 0.0301 | 0.0355 | 0.0416 | 0.0453 | 0.0444 | 0.0487 | 0.0503 | 0.0505 | 0.0553 | 0.0551 |

| | 11 | 12 | 13 | 14 | 15 | 488 nm 16 | 17 | 18 | 19 | 20 | 21 |
|---|---|---|---|---|---|---|---|---|---|---|---|
| | 0.6004 | 0.5458 | 0.3897 | 0.3468 | 0.2586 | 0.1576 | 0.1613 | 0.1309 | 0.1187 | 0.0425 | 0.0197 |
| | 0.0280 | 0.0392 | 0.0445 | 0.0636 | 0.0647 | 0.0386 | 0.0373 | 0.0310 | 0.0303 | 0.0128 | 0.0065 |
| | 0.0488 | 0.0475 | 0.0436 | 0.0464 | 0.0413 | 0.0361 | 0.0388 | 0.0381 | 0.0410 | 0.0248 | 0.0191 |
| | 0.0559 | 0.0576 | 0.0512 | 0.0537 | 0.0486 | 0.0421 | 0.0456 | 0.0445 | 0.0490 | 0.0310 | 0.0228 |

| | 22 | 23 | 24 | 25 | 26 | 488 nm 27 | 28 | 29 | 30 | 31 | 32 |
|---|---|---|---|---|---|---|---|---|---|---|---|
| | 0.0848 | 0.0537 | 0.0512 | 0.0468 | 0.0409 | 0.0346 | 0.0322 | 0.0299 | 0.0281 | 0.0260 | 0.0255 |
| | 0.0259 | 0.0165 | 0.0158 | 0.0176 | 0.0158 | 0.0169 | 0.0422 | 0.1690 | 0.5291 | 1 | 0.9920 |
| | 0.0787 | 0.0423 | 0.0333 | 0.0345 | 0.0325 | 0.0267 | 0.0246 | 0.0248 | 0.0238 | 0.0217 | 0.0208 |
| | 0.0961 | 0.0511 | 0.0372 | 0.0399 | 0.0375 | 0.0330 | 0.0299 | 0.0297 | 0.0274 | 0.0289 | 0.0289 |

FIG. 32

(MEAN WAVEFORM BY PERFORMING SIMPLE STAINING FOR EACH DYE: NO MASKING)

| Laser | | | | | | 640 nm | | | | | |
|---|---|---|---|---|---|---|---|---|---|---|---|
| Channel | 1 | 2 | 3 | 4 | 5 | 6 | 7 | 8 | 9 | 10 |
| FITC | 0.1449 | 0.1526 | 0.1565 | 0.1654 | 0.1579 | 0.1564 | 0.1557 | 0.1497 | 0.1529 | 0.1586 |
| PE-Cy7 | 0.0460 | 0.0477 | 0.0477 | 0.0493 | 0.0484 | 0.0487 | 0.0482 | 0.0459 | 0.0482 | 0.0486 |
| APC | 0.1477 | 0.1518 | 0.1519 | 0.1550 | 0.1556 | 0.1529 | 0.1506 | 0.1421 | 0.1530 | 0.1538 |
| unstained | 0.1732 | 0.1779 | 0.1801 | 0.1794 | 0.1811 | 0.1790 | 0.1825 | 0.1693 | 0.1787 | 0.1777 |

| | | | | | 640 nm | | | | | |
|---|---|---|---|---|---|---|---|---|---|---|
| 11 | 12 | 13 | 14 | 15 | 16 | 17 | 18 | 19 | 20 | 21 |
| 0.1490 | 0.1498 | 0.1583 | 0.1574 | 0.1526 | 0.1508 | 0.1475 | 0.1510 | 0.1731 | 0.1557 | 0.1643 |
| 0.0489 | 0.0471 | 0.0516 | 0.0531 | 0.0527 | 0.0498 | 0.0496 | 0.0507 | 0.0563 | 0.0539 | 0.0551 |
| 0.1525 | 0.1489 | 0.1597 | 0.1642 | 0.1581 | 0.1581 | 0.1603 | 0.1587 | 0.1771 | 0.1625 | 0.1829 |
| 0.1742 | 0.1727 | 0.1836 | 0.1869 | 0.1854 | 0.1798 | 0.1848 | 0.1838 | 0.2110 | 0.1910 | 0.2120 |

| | | | | | 640 nm | | | | | |
|---|---|---|---|---|---|---|---|---|---|---|
| 22 | 23 | 24 | 25 | 26 | 27 | 28 | 29 | 30 | 31 | 32 |
| 0.7948 | 0.7016 | 0.1072 | 0.1791 | 0.1774 | 0.1659 | 0.1523 | 0.1563 | 0.1588 | 0.1540 | 0.1518 |
| 0.2573 | 0.2293 | 0.0436 | 0.0677 | 0.0630 | 0.0607 | 0.0790 | 0.1692 | 0.4220 | 0.6687 | 0.6327 |
| 0.8762 | 1 | 0.9979 | 0.5668 | 0.3702 | 0.3113 | 0.3154 | 0.2741 | 0.2210 | 0.1852 | 0.1718 |
| 1 | 0.8850 | 0.1335 | 0.2175 | 0.2139 | 0.2057 | 0.1867 | 0.1978 | 0.1881 | 0.1887 | 0.1908 |

FIG. 35

(SETTING EXAMPLE OF MASKING: IN CASE OF MASKING)

488 nm

| Laser | | | | | | | | | | | | | | | | | | | | |
|---|---|---|---|---|---|---|---|---|---|---|---|---|---|---|---|---|---|---|---|---|
| Channel | 1 | 2 | 3 | 4 | 5 | 6 | 7 | 8 | 9 | 10 | 11 | 12 | 13 | 14 | 15 | 16 | 17 | 18 | 19 | 20 |
| FITC | 1 | 1 | 1 | 1 | 1 | 1 | 1 | 1 | 1 | 1 | 1 | 1 | 1 | 1 | 1 | 1 | 1 | 1 | 0 | 0 |
| PE-Cy7 | 0 | 0 | 0 | 0 | 0 | 0 | 0 | 0 | 0 | 0 | 0 | 0 | 0 | 0 | 1 | 1 | 0 | 0 | 0 | 0 |
| APC | 0 | 0 | 0 | 0 | 0 | 0 | 0 | 0 | 0 | 0 | 0 | 0 | 0 | 0 | 0 | 0 | 0 | 0 | 0 | 0 |

488 nm

| 21 | 22 | 23 | 24 | 25 | 26 | 27 | 28 | 29 | 30 | 31 | 32 |
|---|---|---|---|---|---|---|---|---|---|---|---|
| 0 | 0 | 0 | 0 | 0 | 0 | 0 | 0 | 0 | 0 | 0 | 0 |
| 0 | 0 | 0 | 0 | 0 | 0 | 0 | 1 | 1 | 1 | 1 | 1 |
| 0 | 0 | 0 | 0 | 0 | 0 | 0 | 0 | 0 | 0 | 0 | 0 |

FIG. 36

(SETTING EXAMPLE OF MASKING: IN CASE OF MASKING)

| Laser   | 640 nm | | | | | | | | | | | | | | | | | | | |
|---------|---|---|---|---|---|---|---|---|---|---|---|---|---|---|---|---|---|---|---|---|
| Channel | 1 | 2 | 3 | 4 | 5 | 6 | 7 | 8 | 9 | 10 | 11 | 12 | 13 | 14 | 15 | 16 | 17 | 18 | 19 | 20 |
| FITC    | 0 | 0 | 0 | 0 | 0 | 0 | 0 | 0 | 0 | 0 | 0 | 0 | 0 | 0 | 0 | 0 | 0 | 0 | 0 | 0 |
| PE-Cy7  | 0 | 0 | 0 | 0 | 0 | 0 | 0 | 0 | 0 | 0 | 0 | 0 | 0 | 0 | 0 | 0 | 0 | 0 | 0 | 0 |
| APC     | 0 | 0 | 0 | 0 | 0 | 0 | 0 | 0 | 0 | 0 | 0 | 0 | 0 | 0 | 0 | 0 | 0 | 0 | 0 | 0 |

| 640 nm | | | | | | | | | | | | |
|---|---|---|---|---|---|---|---|---|---|---|---|
| 21 | 22 | 23 | 24 | 25 | 26 | 27 | 28 | 29 | 30 | 31 | 32 |
| 0 | 0 | 0 | 0 | 0 | 0 | 0 | 0 | 0 | 0 | 0 | 0 |
| 0 | 0 | 0 | 1 | 1 | 1 | 0 | 0 | 1 | 1 | 1 | 1 |
| 0 | 0 | 0 | 1 | 1 | 1 | 0 | 0 | 0 | 0 | 0 | 0 |

FIG. 37

(MEAN WAVEFORM BY PERFORMING SIMPLE STAINING FOR EACH DYE: MASKING)

| Laser | | | | | | 488 nm | | | | | |
|---|---|---|---|---|---|---|---|---|---|---|---|
| Channel | 1 | 2 | 3 | 4 | 5 | 6 | 7 | 8 | 9 | 10 |
| FITC | 0.1940 | 0.4286 | 0.6959 | 0.8967 | 0.8884 | 1 | 0.9616 | 0.8624 | 0.7875 | 0.6628 |
| PE-Cy7 | 0 | 0 | 0 | 0 | 0 | 0 | 0 | 0 | 0 | 0 |
| APC | 0 | 0 | 0 | 0 | 0 | 0 | 0 | 0 | 0 | 0 |
| unstained | 0.0301 | 0.0355 | 0.0416 | 0.0453 | 0.0444 | 0.0487 | 0.0503 | 0.0505 | 0.0553 | 0.0551 |

| | | | | | | 488 nm | | | | | |
|---|---|---|---|---|---|---|---|---|---|---|---|
| | 11 | 12 | 13 | 14 | 15 | 16 | 17 | 18 | 19 | 20 | 21 |
| | 0.5764 | 0.5179 | 0.3594 | 0.3129 | 0.2253 | 0.1255 | 0.126 | 0.0956 | 0 | 0 | 0 |
| | 0 | 0 | 0 | 0.0450 | 0.0477 | 0.0239 | 0 | 0 | 0 | 0 | 0 |
| | 0.0559 | 0.0576 | 0.0512 | 0.0537 | 0.0486 | 0.0421 | 0.0456 | 0.0445 | 0.0490 | 0.0310 | 0.0228 |

| | | | | | | 488 nm | | | | | |
|---|---|---|---|---|---|---|---|---|---|---|---|
| | 22 | 23 | 24 | 25 | 26 | 27 | 28 | 29 | 30 | 31 | 32 |
| | 0 | 0 | 0 | 0 | 0 | 0 | 0 | 0 | 0 | 0 | 0 |
| | 0 | 0 | 0 | 0 | 0 | 0 | 0.0318 | 0.1601 | 0.5249 | 1 | 0.9923 |
| | 0.0961 | 0.0511 | 0.0372 | 0.0399 | 0.0375 | 0.0330 | 0.0299 | 0.0297 | 0.0274 | 0.0289 | 0.0289 |

FIG. 38

(MEAN WAVEFORM BY PERFORMING SIMPLE STAINING FOR EACH DYE: MASKING)

| Laser     |   |   |   |   |   | 640 nm |   |   |   |   |
|-----------|---|---|---|---|---|--------|---|---|---|---|
| Channel   | 1 | 2 | 3 | 4 | 5 | 6 | 7 | 8 | 9 | 10 |
| FITC      | 0 | 0 | 0 | 0 | 0 | 0 | 0 | 0 | 0 | 0 |
| PE-Cy7    | 0 | 0 | 0 | 0 | 0 | 0 | 0 | 0 | 0 | 0 |
| APC       | 0 | 0 | 0 | 0 | 0 | 0 | 0 | 0 | 0 | 0 |
| unstained | 0.1732 | 0.1779 | 0.1801 | 0.1794 | 0.1811 | 0.1790 | 0.1825 | 0.1693 | 0.1787 | 0.1777 |

| | | | | | 640 nm | | | | | |
|---|---|---|---|---|---|---|---|---|---|---|
| 11 | 12 | 13 | 14 | 15 | 16 | 17 | 18 | 19 | 20 | 21 |
| 0 | 0 | 0 | 0 | 0 | 0 | 0 | 0 | 0 | 0 | 0 |
| 0 | 0 | 0 | 0 | 0 | 0 | 0 | 0 | 0 | 0 | 0 |
| 0 | 0 | 0 | 0 | 0 | 0 | 0 | 0 | 0 | 0 | 0 |
| 0.1742 | 0.1727 | 0.1836 | 0.1869 | 0.1854 | 0.1798 | 0.1848 | 0.1838 | 0.2110 | 0.1910 | 0.2120 |

| | | | | | 640 nm | | | | | |
|---|---|---|---|---|---|---|---|---|---|---|
| 22 | 23 | 24 | 25 | 26 | 27 | 28 | 29 | 30 | 31 | 32 |
| 0 | 0 | 0 | 0 | 0 | 0 | 0 | 0 | 0 | 0 | 0 |
| 0 | 0 | 0 | 0 | 0 | 0 | 0 | 0.1000 | 0.3570 | 0.6071 | 0.5709 |
| 0 | 0 | 0.1335 | 0.3943 | 0.1746 | 0 | 0 | 0 | 0 | 0 | 0 |
| 0.8850 | 1 | 1 | 0.2175 | 0.2139 | 0.2057 | 0.1867 | 0.1978 | 0.1881 | 0.1887 | 0.1908 |

DETECTING FLUORESCENT MATERIAL IN A STAINED PARTICLE BY COMPARISON WITH AN UNSTAINED PARTICLE OVER A PLURALITY OF FREQUENCY BANDS AND BY ESTIMATING A LINEAR COMBINATION OF BASE VECTORS

CROSS-REFERENCE TO RELATED APPLICATIONS

This application claims priority to Japanese Patent Application Number 2012-122161, filed in the Japanese Patent Office on May 29, 2012, which is herein incorporated by reference in its entirety.

BACKGROUND

The present disclosure relates to an information processing apparatus, an information processing method, and a program.

In order to measure the characteristics of microparticles such as cells, an apparatus (for example, a flow cytometer or the like) is used which irradiates a laser beam to microparticles labeled with fluorescent dyes, and measures the intensity or pattern of fluorescence generated from the excited fluorescent dyes. Further, a technology called multi-color measurement, which labels microparticles by using a plurality of fluorescent dyes, and measures the fluorescence emitted from each fluorescent dye irradiated with a laser beam with a plurality of photodetectors having different light reception frequency bands, has also been used as a technology which analyzes the characteristics of microparticles in more detail. Note that a transparent frequency band of an optical filter installed in each photodetector for restricting the light reception frequency band is designed according to the fluorescent wavelength of the fluorescence emitted from the fluorescent dye to be measured.

For example, FITC (fluorescein isothiocyanate), PE (phycoerythrin) or the like are used as fluorescent dyes. When observing a fluorescence spectrum obtained by irradiating a laser beam to microparticles labeled using these fluorescent dyes, the presence of fluorescence frequency bands which mutually overlap one another is confirmed. That is, in the case where multi-color measurement is performed, a component of fluorescence emitted from a fluorescent dye other than an intended fluorescent dye can be considered to leak into the fluorescence spectrum detected by each photodetector, even if the fluorescence obtained by irradiating the laser beam to the microparticles is divided into separate frequency bands by an optical filter. When such a leakage of fluorescence occurs, a deviation may occur between the fluorescence intensity measured by each photodetector and the fluorescence intensity of the fluorescence actually emitted from the intended fluorescent dye. As a result, a measurement error occurs.

In order to correct such a measurement error, a fluorescence correction process (compensation) is performed which subtracts the fluorescence intensity of the leaking part from the fluorescence intensity measured by the photodetector. This fluorescence correction process adds a correction to the measured fluorescence intensity (hereinafter, called a fluorescence correction), so that the fluorescence intensity measured by the photodetector approaches the fluorescence intensity of the fluorescence actually emitted from the intended fluorescent dye. For example, a method which mathematically corrects the fluorescence intensity is disclosed in JP 2003-83894A as a method which performs a fluorescence correction.

The method disclosed in JP 2003-83894A calculates the fluorescence intensity of the fluorescence actually emitted from the intended fluorescent dye, by considering a vector which has a fluorescence intensity (detection value) measured by each photodetector set as an element, and by applying an inverse matrix of a correction matrix set in advance in this vector. Note that the above described correction matrix is sometimes called a leakage matrix. The above described correction matrix is created by analyzing a florescence wavelength distribution of microparticles singly labeled with each fluorescent dye, and is arranged by setting the florescence wavelength distributions of each fluorescent dye as a row vector.

SUMMARY

Note that the fluorescence correction process disclosed in JP 2003-83894A allows negative values for the matrix elements of the correction matrix. Therefore, when this fluorescence correction process is applied, there are cases where the fluorescence intensity after correction has a negative value. The problem with the fluorescence intensity after correction taking a negative value is that noise included in a detection value of each photodetector affects the values of the matrix elements. However, the fluorescence intensity does not actually have a negative value. Further, calculating the fluorescence intensity of fluorescence emitted from some fluorescent dye as a negative value has the meaning that an error is simultaneously occurring in the positive direction for a calculation value of a fluorescence intensity related to another fluorescent dye.

For example, a case will be considered where a sub-group (hereinafter, called a sub-population), in which the fluorescence intensity of some fluorescent dye has a negative value, is present in a microparticle group to be analyzed (hereinafter, called a population). In this case, when a two-dimensional correlation diagram (hereinafter, a called a cytogram) is created, which plots the fluorescence intensity of this fluorescent dye on a logarithmic scale, the sub-population may not be plotted on the cytogram. Therefore, the population plotted on the cytogram may be seen to be smaller than the actual population.

Further, when subtracting the detection value of autofluorescence emitted from microparticles from the detection value of each photodetector as a background, the fluorescence correction process such as described in JP 2003-83894A uses a mean value of the autofluorescence intensities of the entire population for the operation. The intensity or pattern of the autofluorescence differs for each sub-population. Therefore, when an operation is performed which subtracts the above described mean value uniformly for all the sub-populations, an error in the calculated values of fluorescence intensity may occur. This error becomes significant in the case where the autofluorescence intensity varies widely between the sub-populations to be analyzed.

Incidentally, a situation in which a peak present in some frequency band originates from a plurality of chemical species may not occur in only the fluorescence spectrum of the microparticles labeled by the fluorescent dyes. For example, a similar situation may occur in an emission spectrum, an absorption spectrum or the like in which a plurality of chemical species coexist.

Therefore, a correction method has been widely demanded which effectively suppresses the components of other light emission elements leaking into the spectrum of light emitted from an intended light emission element, when executing a process which analyzes the spectrum of light emitted from a plurality of light emission elements for each light emission element. By considering such a situation, the present inventors have already disclosed a technique which extracts an intended spectrum component from a measured spectrum with higher accuracy (for example, Japanese Patent Application No. 2011-161758).

Incidentally, usually a dye emits fluorescence in a specific frequency band and does not emit fluorescence in the other frequency bands. However, there are times when the fluorescence intensity is observed in frequency bands other than the specific frequency band. This means that noise originating from the autofluorescence of a cell or from the apparatus (hereinafter, called noise or the like) is observed, similar to when measuring an undyed sample. Therefore, even if the observation results of microparticles singly labeled by some dye are used as base vectors, there are times where the application of these base vectors may occur in the observation results of samples not including this dye, due to the influence of noise or the like. As a result, there is a concern that an adverse influence may be exerted on the fluorescence correction.

Accordingly, the present disclosure proposes an information processing apparatus, an information processing method, and a program capable of extracting an intended spectrum component from a measured spectrum with higher accuracy.

According to an embodiment of the present disclosure, there is provided an information processing apparatus, including a testing section which performs statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band, a masking processing section which sets, in a case where there is no significant difference between the simple staining data and the unstaining data for the frequency band, the simple staining data to 0 or a prescribed value, and an estimation section which estimates, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

According to an embodiment of the present disclosure, there is provided an information processing method, including performing statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band, setting, in a case where there is no significant difference between the simple staining data and the unstaining data for the frequency band, the simple staining data to 0 or a prescribed value, and estimating, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

According to an embodiment of the present disclosure, there is provided a program for causing a computer to implement a testing function which performs statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band, a masking processing function which sets, in a case where there is no significant difference between the simple staining data and the unstaining data for the frequency band, the simple staining data to 0 or a prescribed value, and an estimation function which estimates, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

Further, according to an embodiment of the present disclosure, there is provided a computer-readable recording medium recording the above described program.

According to the embodiments of the present disclosure such as described above, it is possible to extract an intended spectrum component from a measured spectrum with higher accuracy.

BRIEF DESCRIPTION OF THE DRAWINGS

FIG. 22 is a graph chart which shows a two-dimensional correlation diagram of a mixed sample;

FIG. 25 is a graph chart which shows a two-dimensional correlation diagram of a mixed sample;

FIG. 29 is an explanatory diagram which shows a setting example of a mask for each channel;

FIG. 30 is an explanatory diagram which shows a setting example of a mask for each channel;

FIG. 31 is an explanatory diagram which shows a mean waveform (no masking) by performing simple staining for each dye;

FIG. 32 is an explanatory diagram which shows a mean waveform (no masking) by performing simple staining for each dye;

FIG. 35 is an explanatory diagram which shows a setting example of a mask for each channel;

FIG. 36 is an explanatory diagram which shows a setting example of a mask for each channel;

FIG. 37 is an explanatory diagram which shows a mean waveform (masking) by performing simple staining for each dye;

FIG. 38 is an explanatory diagram which shows a mean waveform (masking) by performing simple staining for each dye;

DETAILED DESCRIPTION OF THE EMBODIMENT(S)

Figure 1:
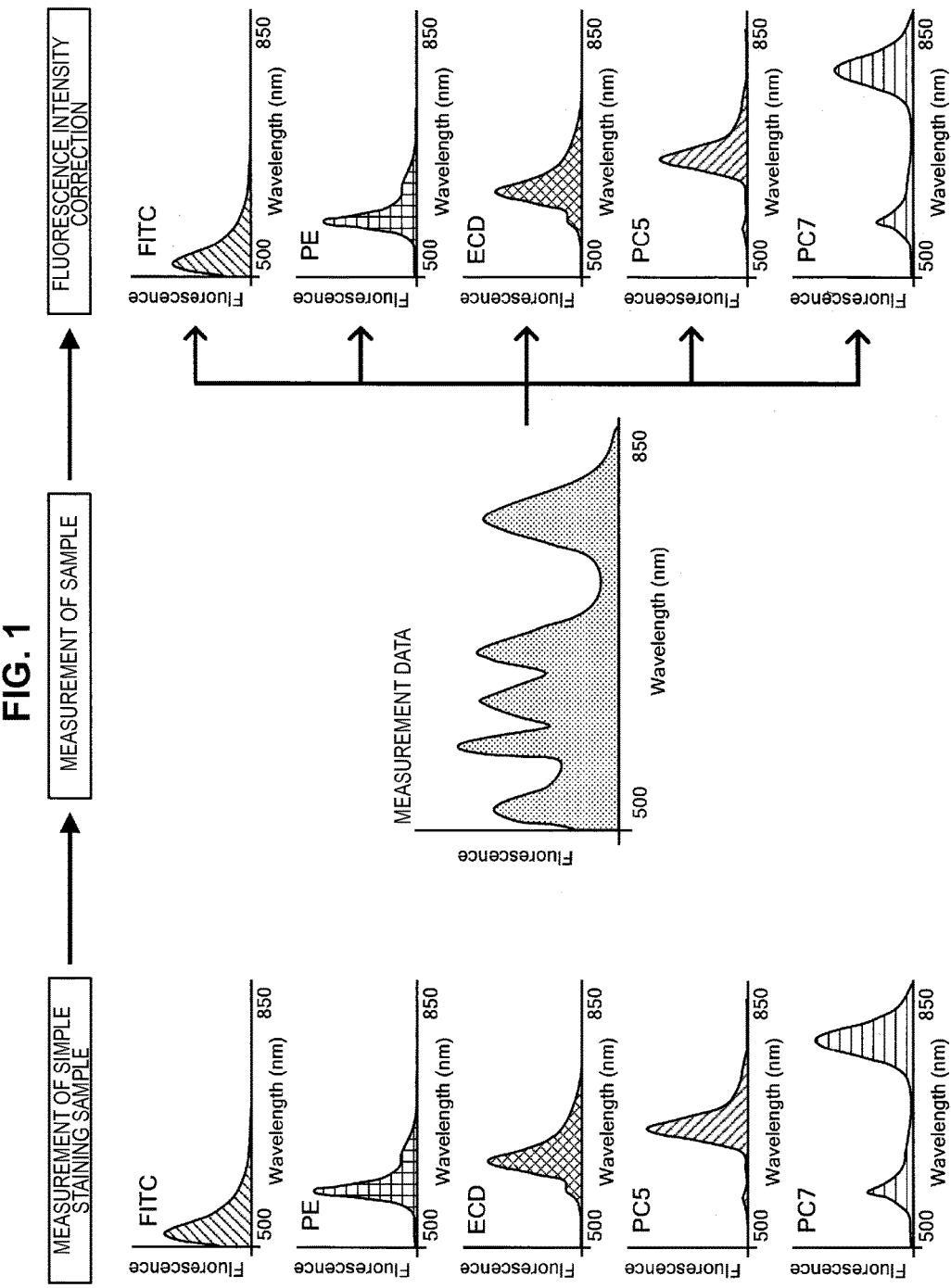
FIG. 1 is an explanatory diagram for describing a fluorescence intensity correction process.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Here, the flow of the description will be described. First, before the technology according to the present embodiment is described in detail, the contents of the technology related to this technology will be introduced. Further, the problems faced by the related technology will be described, and an outline of the technology of the present embodiment enabled to solve these problems will be described. Then, the technology according to the present embodiment will be described in detail. Within this, the contribution for reflecting the technical idea according to the present embodiment in a specific configuration, a configuration example of a system according to this technical idea, and an example of the configuration example of an apparatus and the processing contents will be described.

In addition, a result (example) which specifically verifies the effect obtained by the application of the technology according to this embodiment will be shown, and the effect accomplished by this technology will be confirmed. Further, a hardware configuration example capable of executing the functions of the apparatus showing the configuration example in the present disclosure will be introduced. Finally, the technical ideas according to the present embodiment will be brought together, and the operation and effect obtained by the application of this technical idea will be referred to.

DESCRIPTION ITEMS

1: Introduction
   1-1: Correction method of fluorescence intensity
   1-2: Outline of the present embodiment
2: Details of the Embodiments
   2-1: Example configuration of the system
   2-2: Example configuration of the apparatus
   2-3 Process flow
   2-4: Example
   2-5: Masking process
3: Example Hardware Configuration
4: Conclusion

1: INTRODUCTION

First of all, before the technology according to the present embodiment is described in detail, the technology related to this technology and an outline of the technology according to the present embodiment will be introduced. Specifically, correction methods of fluorescence intensity based on an "inverse matrix method" and "restricted least square method" will be introduced.

1-1: Correction Method of Fluorescence Intensity

First, a correction method of fluorescence intensity will be briefly described with reference to FIGS. 1 to 4. FIGS. 1 to 4 are explanatory diagrams for describing a correction method of fluorescence intensity.

Hereinafter, a method which measures a fluorescence spectrum, such as biological cells labeled by fluorescent dyes, in a flow cyclometer and applies a fluorescence intensity correction to this measurement result will be described as an example. In particular, a case will be considered where microparticles such as biological cells are subjected to multiple staining using plural types of fluorescent dyes, and the fluorescence spectrum of the stained microparticles is measured.

First, a simple staining sample, in which microparticles are stained using each fluorescent dye individually, is prepared. Then, the fluorescence spectrum of the simple staining sample is measured in advance, as shown in FIG. 1. In the example shown in FIG. 1, in the case where five types of fluorescent dyes, FITC, PE, ECD, PC5, and PC7, are each used individually, the fluorescence spectra are measured in advance. Afterwards, a sample is subjected to multiple staining with the plural types of fluorescent dyes, and a fluorescence spectrum is measured. The measured fluorescence spectrum is a spectrum in which the florescence intensities originating from the respective fluorescent dyes used for labeling overlap one other. Accordingly, the ratio at which the fluorescence intensity originating from a fluorescent dye overlaps the other fluorescent intensities is specified by performing a fluorescence intensity correction process on the fluorescence spectrum obtained by measurement.

Here, a method which uses the correction matrix disclosed in JP 2003-83894A (hereinafter, also called an inverse matrix method) will be introduced. This method calculates, as a measurement result, a genuine fluorescence intensity (FL) by applying an inverse matrix of the correction matrix to the fluorescence intensity (MI) obtained by the respective photodetectors, as shown in the following Equation (1).

$$\begin{pmatrix} FL_1 \\ FL_2 \\ FL_3 \\ FL_4 \\ FL_5 \end{pmatrix} = \begin{pmatrix} a_{11} & a_{21} & a_{31} & a_{41} & a_{51} \\ a_{12} & a_{22} & a_{32} & a_{42} & a_{52} \\ a_{13} & a_{23} & a_{33} & a_{43} & a_{53} \\ a_{14} & a_{24} & a_{34} & a_{44} & a_{54} \\ a_{15} & a_{25} & a_{35} & a_{45} & a_{55} \end{pmatrix}^{-1} \begin{pmatrix} MI_1 \\ MI_2 \\ MI_3 \\ MI_4 \\ MI_5 \end{pmatrix} \quad (1)$$

Figures 2, 3:
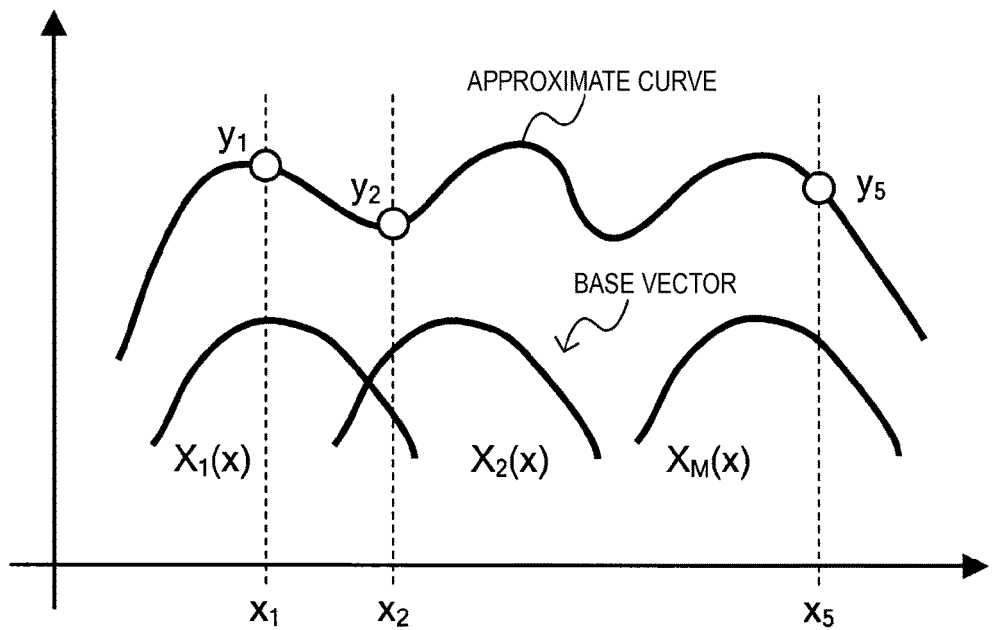
FIG. 2 is an explanatory diagram for describing a fluorescence intensity correction process.
FIG. 3 is an explanatory diagram for describing a fluorescence intensity correction process.

FIG. 2 schematically shows a fluorescence intensity correction method by the inverse matrix method. It can be said that the fluorescence intensity correction method by the inverse matrix method is a method which sets fluorescence spectra of superimposed individual fluorescent dyes as base vectors, and calculates an approximate curve through measurement data measured by the respective photodetectors. For example, when measurement data of photodetectors $x_1$ to $x_5$ is set to be represented by $y_1$ to $y_5$ and the base vectors are set to be represented by $X_1(x)$ to $X_M(x)$, this fluorescence intensity correction is implemented by requesting an approximate curve through all of the measurement data $y_1$ to $y_5$ using the base vectors $X_1(x)$ to $X_M(x)$.

However, in the case of the inverse matrix method, the genuine fluorescence intensity may sometimes become a negative value. Further, in the case of the inverse matrix method, it may be necessary to set the number of installed photodetectors to be the same as the number of used fluorescent dyes. In addition, a condition in which the measurement data of each photodetector is present on an approximate straight line may cause an error in the calculated fluorescence intensity.

Accordingly, a method for resolving the problems of the inverse matrix method such as described above has been examined. First of all, a method has been conceived which calculates a likely approximate curve estimated from the measurement data of each photodetector, by using a least square method, as shown in FIG. 3, without requesting an approximate curve through the measurement data of each photodetector. This method is a method which sets the measurement data of photodetectors $x_1$ to $x_N$ to be represented by $y_1$ to $y_N$, sets the base vectors to be respectively represented by $X_1(x)$ to $X_M(x)$, and calculates an approximate curve with the smallest error between the measurement data $y_1$ to $y_N$ by using the base vectors $X_1(x)$ to $X_M(x)$.

Figure 4:
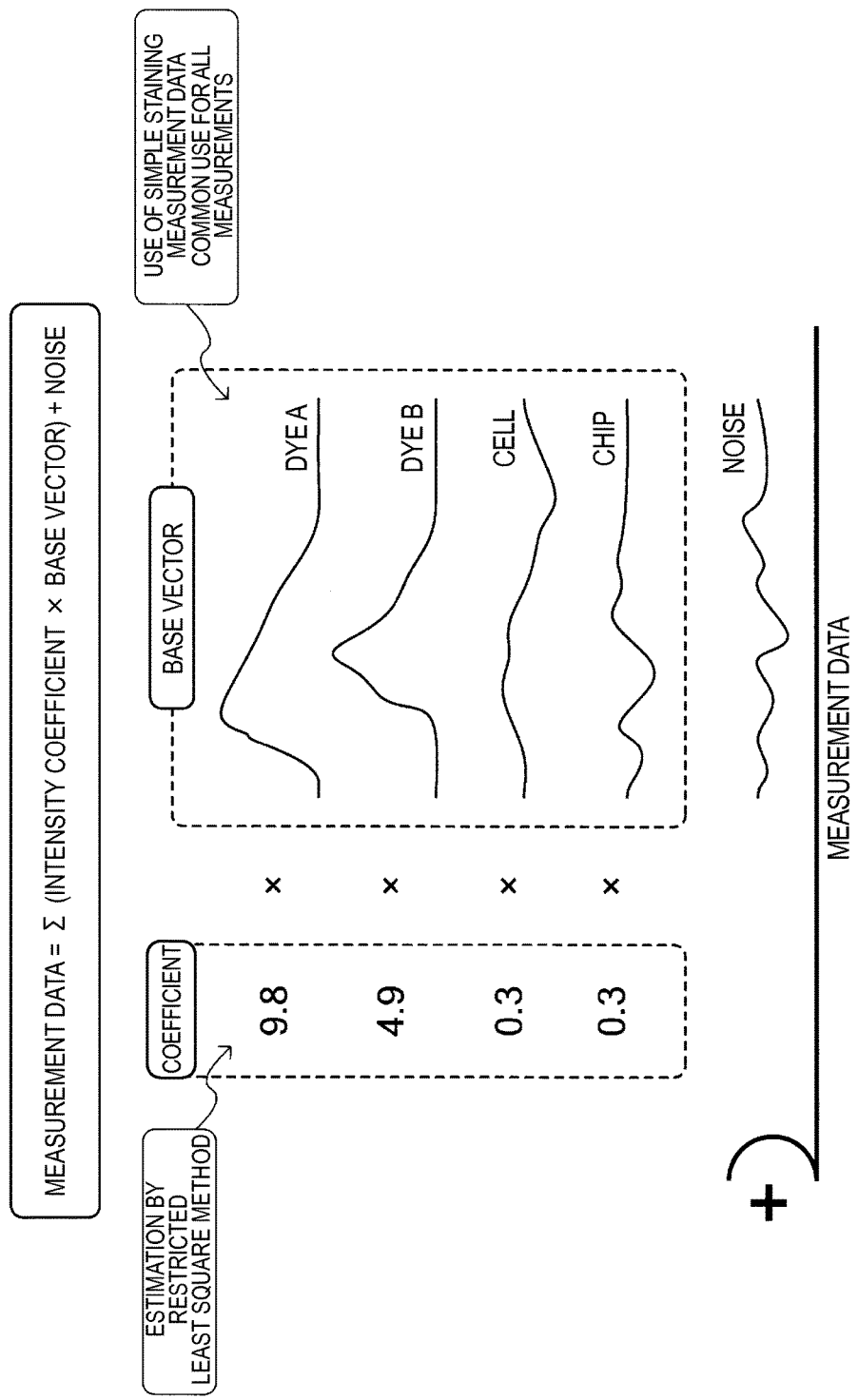
FIG. 4 is an explanatory diagram for describing a fluorescence intensity correction process.

The fluorescence intensity correction method using this least square method can be schematically expressed as in FIG. 4. Here, a further description for the fluorescence intensity correction method using the least square method will be carried forward with reference to FIG. 4.

A set (that is, a fluorescence spectrum) of measurement data measured by each photodetector is a set in which noise is superimposed on a linear sum multiplying prescribed coefficients (intensity coefficients) by a fluorescence spectrum which is a reference used as a base vector (for example, fluorescence spectra in the case where a sample is subjected to simple staining with an individual fluorescent dye, autofluorescence spectra of a sample or the like). Moreover, a specific value of each intensity coefficient is determined by the least square method, based on the measurement data by each photodetector. The intensity coefficient determined in this case becomes the fluorescence intensity after correction (that is, the genuine fluorescence intensity).

Here, when the least square method is performed for requesting the intensity coefficients shown in FIG. 4, the present inventors have recognized an idea which includes a restriction of the value of the intensity coefficient being equal to or more than a prescribed minimum value (for example, equal to or more than zero). When using this idea, the defect of the inverse matrix method, in which the calculated genuine fluorescence intensity may become a negative value, can be resolved. A method which implements this idea is hereinafter called a "restricted least square method".

Hereinafter, a further description for the restricted least square method will be carried forward in combination with specific equations.

First, when a measured fluorescence spectrum is set to be $y(x)$, a base vector of a fluorescent dye k (k=1, . . . , M) is set to be $X_k(x)$, and an intensity coefficient of the fluorescent dye k is set to be $a_k$, the measured fluorescence spectrum $y(x)$ is represented such as in the following Equation (2). Here, when the measurement data by the $i^{th}$ (i=1, . . . , N) photodetector is set to be represented by $y_i$, the least square method under consideration can result in the problem in which the intensity coefficient $a_k$ is requested which provides the minimum value of an evaluation function $\chi^2$ represented in the following Equation (3).

Note that in the following Equation (3), $\sigma_i$ represents an inverse number of a weighted coefficient for the measurement value of the $i^{th}$ photodetector. Note that, for example, a measurement error variance of the $i^{th}$ photodetector may be used as the inverse number of the weighting coefficient, or may be treated as 1. Further, the intensity coefficient $a_k$ satisfies the following Equation (4). The following Equation (4) represents a restriction condition (lower limit value condition) in which the intensity coefficient $a_k$ is larger than a prescribed value ($U_k$).

$$y(x) = \sum_{k=1}^{M} a_k \cdot X_k(x) \quad (2)$$

$$\chi^2 \equiv \sum_{i=t}^{N} \left[ \frac{y_1 - \sum_{k=1}^{M} a_k \cdot X_k(x_i)}{\sigma_i} \right]^2 \quad (3)$$

$$a_k \geq U_k \quad (4)$$

The above described $U_k$ represents a lower limit of the fluorescence intensity of each calculated fluorescent dye. Further, it is possible for a calculation method of the intensity coefficient $a_k$, which provides the minimum value of an evaluation function represented in the above described Equation (3), to be used by any known method.

(Example of a Calculation Method of the Intensity Coefficient $a_k$)

Hereinafter, the procedures for requesting $a_k$ will be specifically described.

When setting an N×M dimensional matrix S having $X_k(x_i)$ as an element, an M dimensional matrix a having $a_k$ as an element, and an N dimensional vector y having $y_i$ as an element, requesting the parameter $a_k$, in which the evaluation function represented in Equation (3) becomes a minimum value while satisfying Equation (4), is identical to solving the following problems.

$$\text{Minimize} \|Sa-y\| \quad (5)$$

$$\text{subject to } Aa \leq b \quad (6)$$

$$a \geq 0 \quad (7)$$

An M×M dimensional matrix A and an M×1 dimensional matrix b are set, such as in the following Equation (8) and Equation (9), by setting a restricting inequality such as the fluorescence intensity a is equal to or above a prescribed value (U).

$$A = \begin{pmatrix} -1 & 0 & \cdots & 0 \\ 0 & -1 & & 0 \\ \vdots & & \ddots & \vdots \\ 0 & 0 & \cdots & -1 \end{pmatrix} \quad (8)$$

$$b = \begin{pmatrix} -U_1 \\ -U_2 \\ \vdots \\ -U_M \end{pmatrix} \quad (9)$$

When the above described Equation (5) is squared and expanded, it becomes the following Equation (10).

$$\|Sa - y\|^2 = (Sa - y)^T(Sa - y) \quad (10)$$
$$= a^T S^T S a - a^T S^T y - y^T S a + y^T y$$
$$= a^T (S^T S) a - 2 y^T S a + y^T y$$

In order to minimize Equation (10), the final item $y^T y$ can be disregarded. Therefore, minimizing Equation (10) is equal to minimizing the following Equation (11).

$$\tfrac{1}{2} a^T (S^T S) a - y^T S a \quad (11)$$

Equation (11) and the above Equation (6) and Equation (7) are known as quadratic programming problems. A quadratic programming problem is a problem which, at the time when an n×n dimensional non-negative constant value symmetric matrix is set to D, an n dimensional vector is set to c, an m×n dimensional matrix is set to A, and an m dimensional vector is set to b, requests a for minimizing an intended function "$f(a)=a^T A a/2 + c^T a$" provided in a two-dimensional form, from among n dimensional vectors a which satisfy a linear restriction condition "$Aa \leq b, a \geq 0$". Note that the quadratic programming problem is known as a special non-linear programming problem in which a strict optimum solution is obtained by repeating a limited number of times.

The intensity coefficient $a_k$ can be calculated by solving the above described quadratic programming problem.

Incidentally, when solving the above described quadratic programming problem, the lower limit value $U_j$ (j=1~M) as a restriction condition is set to an appropriate value, by measuring unstained microparticles not labeled with fluorescent dyes and setting a minimum detection value for the $j^{th}$ fluorescent dye.

For example, an unstaining mean value $V_j$ of the $j^{th}$ fluorescent dye, which is requested from the mean value of the detection values for each photodetector acquired by irradiating light to microparticles not labeled with the $j^{th}$ fluorescent dye, can be used as a setting method of the lower limit value $U_j$. However, a mean value or the like of the detection values in a detector unit, in which the simple staining spectrum of the $j^{th}$ fluorescent dye has the maximum detection values, can be used as the unstaining mean value $V_j$. Needless to say, a method which uses random numbers along with a prescribed probability density function and a normal distribution, a method which sets the lower limit value to 0 or the like can be considered as the setting method of the lower limit value $U_j$ in addition to the method using a mean value. By applying such methods, a desired intensity coefficient $a_k$ can be calculated by solving the above described quadratic programming problem.

(Examination for the Intensity Correction Method by the Restricted Least Square Method)

Here, the effectiveness of the intensity correction method by the restricted least square method, such as described above, will be examined. Through various verifications, the intensity correction method by the restricted least square method described above has been understood to have a considerable improvement in accuracy compared to the intensity correction method based on the inverse matrix method disclosed in JP 2003-83894A. On the other hand, the present inventors have recognized that the following points may be necessary for consideration in the intensity correction method by the restricted least square method described above.

First, in an operation in which a sample to be measured is subjected to simple staining with each dye and the fluorescence spectrum is measured, there are many cases where the time taken for the measurement and a specimen used in the measurement are wasted. Further, in the case where cells are under consideration as a measurement target, there are many cases where it is difficult to prepare cells having completely identical conditions in proportion to the number of dyes.

In addition, while a base vector is common in all of the measurement data in the restricted least square method, in actual fact it is natural to consider non-uniformities existing in the base vector in each measurement due to various causes. Further, as a matter of course, the measurement data in the case where multiple staining cells are subjected to simple staining may not be able to be obtained. That is, a base vector itself may not be originally known.

From the consideration of these points, the present inventors have recognized that the non-uniformity of the base vector itself may be necessary for consideration, and that there is a possibility that an error in the intensity correction process can be suppressed by considering the non-uniformity of the base vector.

Further, while the above described description shows an example which uses measurement data by a sample subjected to simple staining with some dye as the base vector, of course it is possible to also use, for example, the autofluorescence of cells or fluorescence originating from a chip or a tube of a microchannel of a flow cytometer as the base vectors.

Further, as described above, when considering the time to prepare a simple staining sample of cells or the like, the fluorescence spectrum of simple staining beads (such as latex beads) can be considered, instead of the sample of cells or the like, as the base vector. However, since the mean of the fluorescence spectrum of the simple staining beads may deviate from the fluorescence spectrum of the simple staining sample of cells or the like, in the case where the base vector generated from the fluorescence spectrum of the beads is used, the result of the fluorescence intensity correction process may be considerably different compared to the case where the base vector generated from the fluorescence spectrum of the sample of cells or the like is used.

Further, in the restricted least square method described above, it is implicitly assumed that the fluorescence intensities in a plurality of frequency bands obtained from a plurality of photodetectors have comparable non-uniform noise. However, since there is a range in the signal intensity capable of being measured with an appropriate S/N ratio in a photodetector represented by a photomultiplier tube, there is a concern that when the restricted least square method is applied to the measurement data obtained without considering the sensitivity of each photodetector, there is the possibility that an adverse influence may be exerted on the intensity correction processing result.

Accordingly, the present inventors have carried forward improvements based on the above described considerations, and have conceived an intensity correction method capable of performing an intensity correction process with higher accuracy by eliminating the error causes of the intensity correction process, based on the non-uniformity of the base vector. Further, the present inventors have examined the diversity of the measurement data capable of being applied as the base vector and the detection accuracy of the photodetectors, in addition to an improvement in accuracy of the intensity correction process, and have created a new idea for this content (hereinafter, called the prior technique). This content is already disclosed as JP 2011-161758A.

1-2: Outline of the Present Embodiment

The technology according to the present embodiment is related to technology which further improves the "restricted least square method" and "prior technique" described above, and which can extract an intended spectrum component with higher accuracy.

In the case where a sample is subjected to simple staining with some dye, the base vector is a vector which removes noise from an observation vector obtained in the case of fluorescence intensity of one unit. In the technique of JP 2003-83894A, the mean of the observation vector, in which an analysis target is subjected to simple staining with each dye, is used as the base vector in the observation vector of all multiple staining, and this coefficient is sought after by the restricted least square method.

Usually, a dye emits fluorescence in a specific frequency band and does not emit fluorescence in the other frequency bands. However, there are times when the fluorescence intensity is observed in frequency bands other than the specific frequency band. This means that noise originating from the autofluorescence of a cell or from the apparatus (hereinafter, called noise or the like) is observed, similar to when measuring an unstaining sample. Therefore, even if the observation results of microparticles singly labeled by some dye are used as base vectors, there are times where the application of these base vectors may occur in the observation results of samples not including this dye, due to the influence of noise or the like. As a result, there is a concern that an adverse influence may be exerted on the fluorescence correction.

Such matters of concern also exist in the prior technique. Accordingly, the present inventors have conceived a technique (hereinafter, called the present technique) which does not consider the fluorescence of a dye in a region where the dye does not shine (the value of the base vector is set to 0). Hereinafter, not considering (the value of the base vector is set to 0) some channel (frequency) will be called "applying a mask" to this channel. The present technique is related to technology which specifically solves the problem of "how to decide the channel to which to apply a mask".

While it will be described in detail later, the present technique adopts a technique which performs a t-test for unstaining observation data and simple staining observation data in each channel, and a mask is applied if a hypothesis (null hypothesis) of "no difference" is not rejected under a set level of significance p, and a mask is not applied if the hypothesis is rejected. In the case where the simple staining observation data includes stained cells and unstained cells, the simple staining observation data is clustered into an unstaining cluster and a simple staining cluster, and a t-test is performed for the observation data allocated to the simple staining cluster and the unstaining observation data.

By such a configuration, it becomes possible to appropriately eliminate the influence of noise or the like originating from the autofluorescence of a cell or from the apparatus, and it becomes possible to perform fluorescence correction so that an intended spectrum component can be extracted with higher accuracy. Note that while a description is carried forward hereinafter in accordance with an example in which the fluorescence intensity of a masked channel is set to 0, a method can also be considered which fixes the fluorescence intensity of a masked channel at a small value without being set to 0.

Further, while a description is carried forward which includes a t-test as an example of the testing technique, it is also possible to use a statistical testing technique other than that of a t-test. For example, it is possible to use techniques such as the Mann-Whitney U test, two-sample Kolmogorov-Smirnov test, Van der Waerden test, or median test.

2: DETAILS OF THE EMBODIMENTS

Hereinafter, the present embodiment will be described in detail with reference to FIGS. 5 to 10.

2-1: Example Configuration of the System

Figure 5:
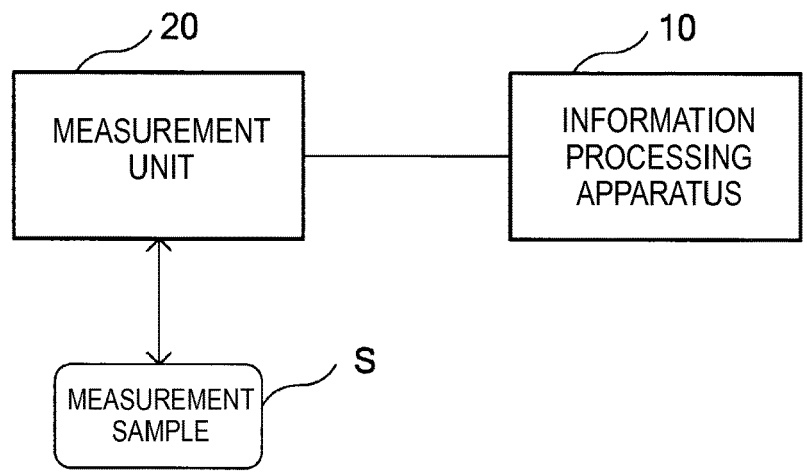
FIG. 5 is an explanatory diagram which shows an information processing system according to a first embodiment of the present disclosure.

First, a configuration example of a system according to the present embodiment will be described with reference to FIG. 5. FIG. 5 is an explanatory diagram which shows a configuration example of a system according to the present embodiment.

As shown in FIG. 5, the system according to the present embodiment mainly includes an information processing apparatus 10, and various measurement units 20 which measure the spectrum of a measurement sample S.
(Outline of the Measurement Sample S)

Biological microparticles such as cells, microbes or liposomes, or synthetic particles such as latex particles, gel particles, or industrial particles, for example, can be used as microparticles which are used as the measurement sample S.

Chromosomes included in various cells, liposomes, mitochondria, organelles (cell organelles) or the like are included as the biological microparticles. Animal cells (such as blood cells) and plant cells are included as the cells. Bacilli such as colon bacilli, viruses such as tobacco mosaic viruses, and fungi such as yeast are included as the microbes. Nucleic acids, proteins, and biological polymers such as composites may also be included as the biological microparticles.

Further, for example, organic polymeric materials, inorganic polymeric materials, metals or the like are used as the industrial particles. Further, for example, polystyrene, styrene divinylbenzene, polymethylmethacrylate or the like are used as the organic polymeric materials. For example, glass, silica, magnetic materials or the like are used as the inorganic polymeric materials. For example, gold colloid, aluminum or the like are used as the metals. The shape of these microparticles may be spherical, or they may be non-spherical. In addition, the size, mass or the like of these microparticles are not particularly limited.
(Outline of the Information Processing Apparatus 10)

The information processing apparatus 10 acquires the measurement data of the measurement sample S measured by the measurement unit 20, and performs an intensity correction process which corrects the intensity of a spectrum which is the acquired measurement data. In the example of FIG. 5, while the information processing apparatus 10 is described as an apparatus separate from the measurement unit 20, the functions of the information processing apparatus 10 may be implemented by a computer which controls the measurement unit 20, or may be implemented within the casing of the measurement unit 20. Note that a detailed configuration of the information processing apparatus 10 will be described in detail later.
(Outline of the Measurement Unit 20)

The measurement unit 20 irradiates a laser beam to the measurement sample S, and measures fluorescence, phosphorescence or the like emitted from the measurement sample S, measures scattered light by the measurement sample S, or measures the absorption spectrum by the measurement sample S. The measurement unit 20 may measure either one or two or more of the emission spectrum, the scatter spectrum, or the absorption spectrum of the measurement sample S. Note that in the present disclosure, these spectra are called "light intensity distributions".

Note that hereinafter, an example will be described in which a flow cytometer measuring the fluorescence spectrum of the measurement sample S (for example, refer to FIGS. 6 and 7) is used as the measurement unit 20.
(Details of the Measurement Sample S)

The microparticles which are used as the measurement sample S are multiply labeled (multiple staining) by a plurality of fluorescent dyes before the measurement of the fluorescence spectrum. Fluorescent dye labeling of the microparticles can be performed according to a well-known arbitrary technique. For example, in the case where a measurement target is set as cells, a fluorescence labeled antibody for cell surface molecules is mixed with the cells, and an antibody is bonded with the cell surface molecules. The fluorescence labeled antibody may be a fluorescent dye directly bonded with the antibody, or may be a fluorescent dye, in which avidin is bonded with a biotin labeled antibody, bonded according to an avidin-biotin reaction. Further, the antibody may be a monoclonal antibody or a polyclonal antibody.

Two or more well-known substances can be combined and used in the fluorescent dye for multiply labeling the microparticles. For example, phycoerythrin (PE), FITC, PE-Cy5, PE-Cy7, PE-Texas red, allophy-cocyanin (APC), APC-Cy7, ethidium bromide, propidium iodide, Hoechst 33258/33342, DAPI, acridine orange, chromomycin, mithramycin, olivomycin, pyronin Y, thiazole orange, rhodamine 101, isothiocyanate, BCECF, BCECF-AM, C.SNARF-1, C.SNARF-1-AMA, aequorin, Indo-1, Indo-1-AM, Fluo-3, Fluo-3-AM, Fura-2, Fura-2-AM, oxonol, Texas red, rhodamine 123, 10-N-nonyl acridine orange (acridine orange), fluorescein, fluorescein diacetate, carboxyfluorescein, carboxyfluorescein diacetate, carboxydichlorofluorescein, or carboxydichlorofluorescein diacetate can be used as the fluorescent dye. Needless to say, the fluorescent dye capable of being used in the present embodiment is not limited to the above described examples.

2-2: Example Configuration of the Apparatus

Hereinafter, the configurations of the measurement unit 20 and the information processing apparatus 10 will be described in more detail.
(Details of the Measurement Unit 20)

Figure 6:
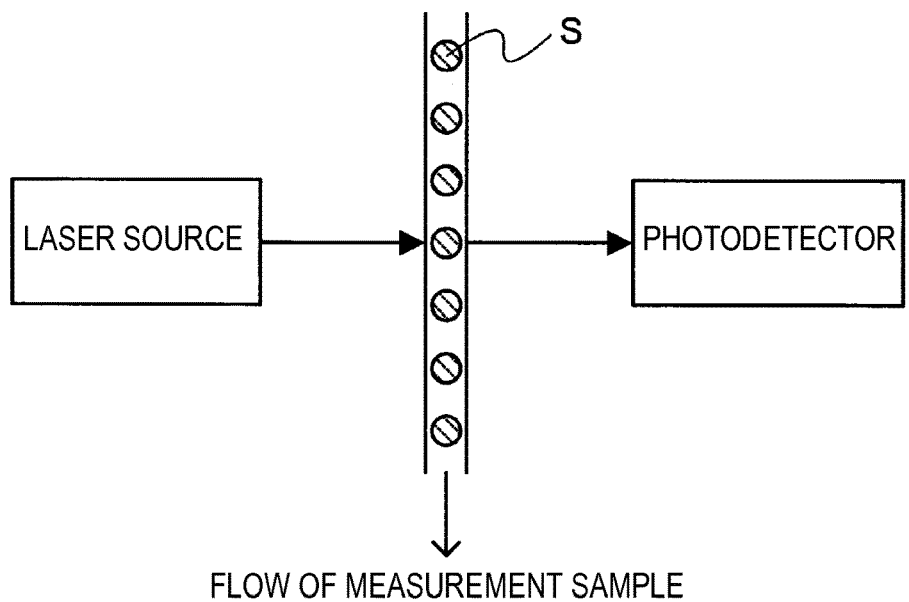
FIG. 6 is an explanatory diagram which shows an example of a measurement unit according to the first embodiment.

The flow cytometer, which is an example of the measurement unit 20, emits a laser beam having a wavelength capable of exciting a fluorescent dye used to stain the sample S, as shown in FIG. 6, to the microparticles S subjected to multiple staining flowing along a microchannel from the laser source. Further, the photodetector installed in the flow cytometer detects the fluorescence released from the microparticles radiated with the laser beam by a photodetector such as a photomultiplier tube or the like. Note that while only one laser source is shown in the example of FIG. 6, a plurality of laser sources may be included which mutually emit laser beams of different wavelengths.

Figure 7:
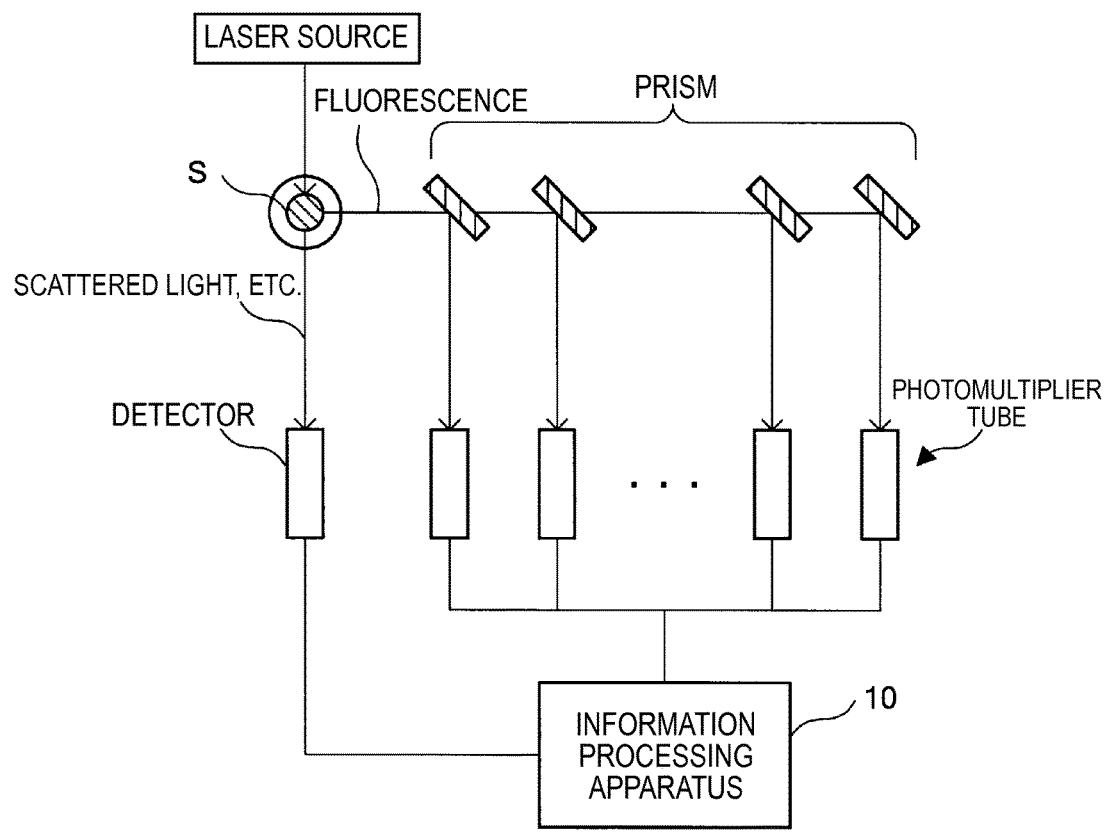
FIG. 7 is an explanatory diagram which shows an example of a measurement unit according to the first embodiment.

While it is possible for the flow cytometer which performs such a measurement process to have a well-known configuration, it has the configuration, for example, such as shown in FIG. 7.

As shown in FIG. 7, the flow cytometer has a laser source which emits a laser beam with a prescribed wavelength (for example, a laser beam with a wavelength of 488 nm or 640 nm), an optical system (not shown in the figures) such as a lens for guiding the laser beam to the measurement sample S, various photodetectors for detecting scattered light, such as forward-scattered or backward-scattered light, or fluorescence from the measurement sample S, and various optical systems for guiding the scattered light or fluorescence to the photodetectors.

Here, in the example shown in FIG. 7, detectors such as a CCD (Charge Coupled Device), a CMOS (Complementary Metal Oxide Semiconductor), photodiodes or the like for detecting scattered light or the like from the measurement sample S, and a plurality of (for example, 32) photomultiplier tubes for detecting fluorescence of the measurement sample S are included as the photodetectors.

Note that in the case where the technology according to the present embodiment is applied, the number of photodetectors may be set so as to be greater than the number of fluorescent dyes used to performing multiple staining on the measurement sample S. That is, in the case where the intensity correction process of the present embodiment, which is described below, is applied, a desired result can be obtained with high accuracy, even for the setting condition of (the number of fluorescent dyes)<(the number of photodetectors).

The fluorescence from the measurement sample S, which is caused by the laser beam emitted from the laser source, is spectrally separated by a prism installed between the measurement sample S and each photomultiplier tube, and is guided to each photomultiplier tube. Each photomultiplier tube outputs measurement data showing a detection result of the fluorescence of the corresponding frequency band to the information processing apparatus 10.

As described above, the information processing apparatus 10 obtains fluorescence spectra in which the fluorescence from the measurement sample S is continuously measured. Further, the measurement data of the scattered light or the like detected by a detector such as a CCD, CMOS, or photodiode may be configured so as to be output to the information processing apparatus 10.

Note that while a series of optical systems for detecting the scattered light from the measurement sample S are included in the flow cytometer shown in the example of FIG. 7, such optical systems may not be included. Further, while the fluorescence from the measurement sample S is spectrally separated by the prisms and guided to the photomultiplier tubes in the flow cytometer shown in FIG. 7, the fluorescence from the measurement sample S may be separated by a plurality of wavelength selection filters and guided to each photomultiplier tube. That is, if there is a configuration in which the fluorescence spectrum obtained by exciting the sample S subjected multiple staining with the laser beam can be selectively measured for each prescribed wavelength, and this measurement result can be output to the information processing apparatus 10, part of the structural components may be arbitrary modified.

Heretofore, a configuration example of the measurement unit 20 has been described.

(Details of the Information Processing Apparatus 10)

Figure 8:
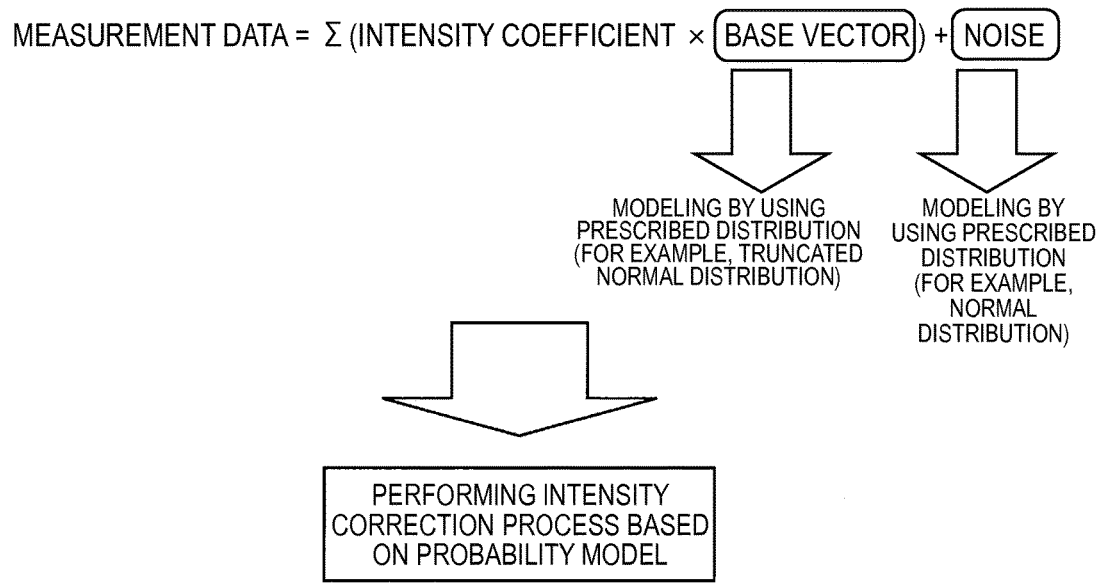
FIG. 8 is an explanatory diagram which shows an outline of an intensity correction process according to the first embodiment.
Figure 9:
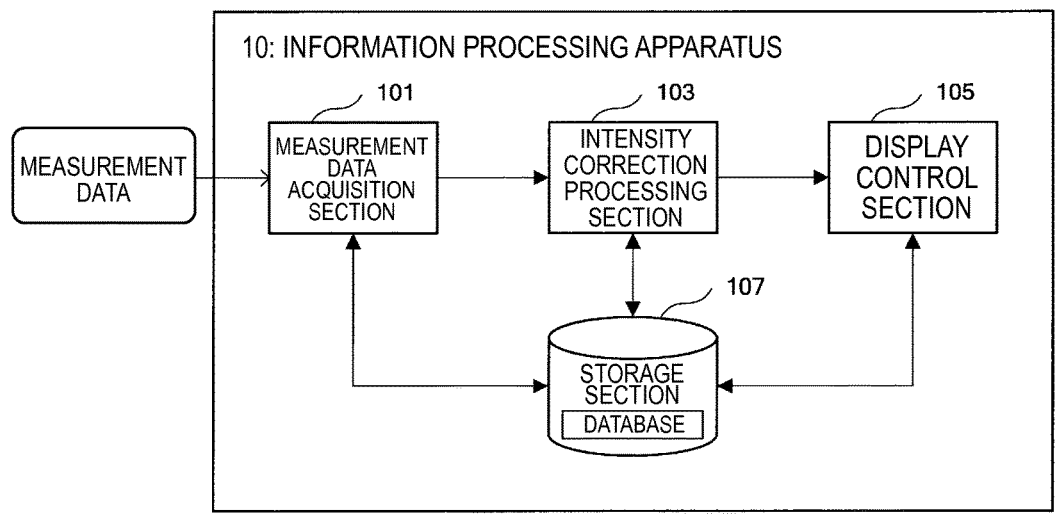
FIG. 9 is a block diagram which shows an example of a configuration of an information processing apparatus according to the first embodiment.
Figure 10:
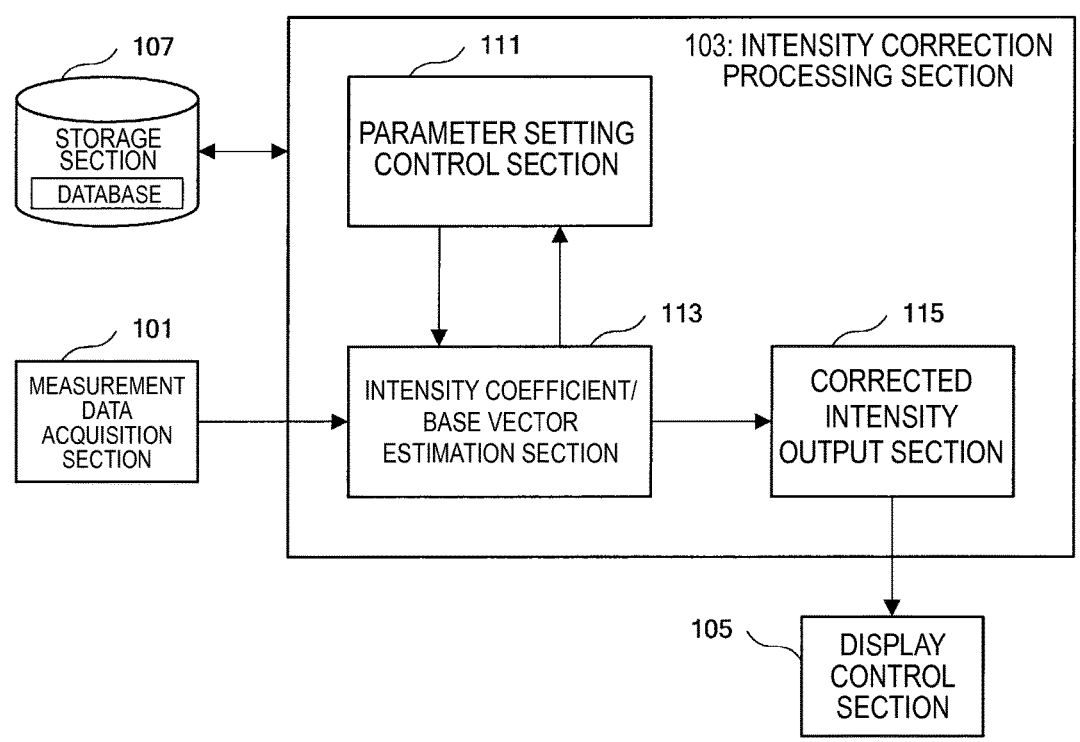
FIG. 10 is a block diagram which shows an example of a configuration of an intensity correction processing section according to the first embodiment.

Next, the configuration of the information processing apparatus 10 will be described in more detail with reference to FIGS. 8 to 10. FIG. 8 is an explanatory diagram for describing an outline of an intensity correction process by the information processing apparatus 10. FIG. 9 is a block diagram which shows the configuration of the information processing apparatus 10. FIG. 10 is a block diagram which shows a detailed configuration of an intensity correction processing section 103 of the information processing apparatus 10.

First, FIG. 8 will be referred to.

As shown in FIG. 8, the information processing apparatus 10 deals with "measurement data which superimposes noise on a linear sum multiplying intensity coefficients by base vectors used in the intensity correction process". Moreover, the information processing apparatus 10 models the base vectors by using a prescribed distribution (for example, a truncated normal distribution), models the noise by using a prescribed distribution (for example, a normal distribution), and performs the intensity correction process based on a probability model. Hereinafter, the prescribed distribution which represents the base vectors will be sometimes called a prior distribution.

The information processing apparatus 10 improves the non-uniformity of the base vectors in each measurement by modeling the base vectors using the prescribed distribution, estimating the base vector in each measurement data by the probability model, and correcting the prior distribution. In this way, it becomes possible to estimate the base vector of each measurement data (each measurement spectrum), or to estimate a base vector common to each measurement data.

Further, the information processing apparatus 10 performs estimation of the base vector, and estimates not only the base vector of the fluorescent dye, but also the fluorescence of a measurement sample such as a cell itself or the fluorescence of a microchannel chip. Accordingly, the information processing apparatus 10 can diversify measured data capable of being used as the base vector. In addition, the information processing apparatus 10 can also use a spectrum measured in advance or prior knowledge, such as a database related to the spectrum, as an initial value of the prior distribution.

Further, the information processing apparatus 10 can implement the intensity correction process, which takes into consideration the sensitivity of each photodetector, by modeling a vector which represents noise (a noise vector) by a normal distribution with variances having no correlation and which are different in each dimension, and estimating the variance of each noise dimension.

Next, FIG. 9 will be referred to.

As shown in FIG. 9, the information processing apparatus 10 mainly has a measurement data acquisition section 101, an intensity correction processing section 103, a display control section 105, and a storage section 107.

The measurement data acquisition section 101 is implemented by, for example, a CPU (Central Processing Unit), a ROM (Read Only Memory), a RAM (Random Access Memory), an input device, a communication device and the like. The measurement data acquisition section 101 acquires measurement data of the measurement sample S obtained by the measurement unit 20.

The measurement data of the measurement sample S acquired from the measurement unit 20 is, for example, data which represents the intensity of a spectrum produced by irradiating a laser beam with a prescribed wavelength to one microparticle or a prescribed number of microparticles. There is a time duration, which is minute, in the measurement of the spectrum of one microparticle or a prescribed number of particles. Accordingly, an accumulated intensity, the maximum intensity, a mean intensity or the like in this minute time duration is used in the measurement data according to the present embodiment.

When the measurement data of the measurement sample S under consideration is acquired, the measurement data acquisition section 101 inputs the acquired measurement data to the intensity correction processing section 103, which is described later. Further, the measurement data acquisition section 101 may store the acquired measurement data in the storage section 107, which is described later, as history information in association with time information such as an acquisition date of this measurement data.

The intensity correction processing section 103 is implemented by, for example, a CPU, a DSP (Digital Signal Processor), a ROM, a RAM and the like. The intensity correction processing section 103 performs an intensity correction process of various spectra measured by the measurement unit 20, by using measurement data of the measurement sample S output from the measurement data acquisition section 101, and a prior knowledge database or the like related to base vectors stored in the storage section 107 or the like, which is described later.

The intensity correction processing section 103 calculates a genuine intensity for each base vector by the intensity correction method previously described above. Accordingly, the calculated genuine intensity becomes more accurate even compared to the result obtained by the intensity correction method using the restricted least square method.

The intensity correction processing section 103 inputs the intensity correction processing result of various spectra output from the measurement data acquisition section 101 to the display control section 105, which is described later. The display control section 105 presents the user with the input processing result. Further, the intensity correction processing section 103 may perform an update process of various databases stored in the storage section 107 or the like, which is described later, by using the intensity correction processing result.

Further, the intensity correction processing section 103 may present the user with the intensity correction processing result as printed material via an output device such as a printer, or may output data which represents the obtained intensity correction processing result to various recording media such as a CD, DVD, or Blu-ray disc, or to a USB memory. Further, the intensity correction processing section 103 may output the data which represents the obtained intensity correction processing result to an external apparatus via various communication networks. In addition, the intensity correction processing section 103 may store the data which represents the intensity correction processing result in the storage section 107, which is described later, as history information in association with time information related to a generation date or the like of this data.

Note that the configuration of the intensity correction processing section 103 will be described later in more detail.

The display control section 105 is implemented by, for example, a CPU, ROM, RAM, communication apparatus, output device and the like. The display control section 105 performs display control of a display screen in a display device, such as a display included in the information processing apparatus 10 or a display installed outside of the information processing apparatus 10.

More specifically, the display control section 105 performs display control of the display screen, based on information related to the intensity correction processing result (the spectrum intensities after correction) of the various spectra notified from the intensity correction processing section 103. It becomes possible for the user of the information processing apparatus 10 to comprehend the result of the intensity correction process, by having the display control section 105 perform display control of the display screen for the intensity correction processing result notified from the intensity correction processing section 103.

The functions of the storage section 107 are implemented by, for example, a RAM or storage device included in the information processing apparatus 10. Various databases used by the intensity correction processing section 103 in the intensity correction process of the spectrum, information related to the prior knowledge or the like is stored in this storage section 107. Further, various measurement data or the like acquired by the measurement data acquisition section 101 is also stored in the storage section 107.

In addition, execution data corresponding to various applications used by the intensity correction processing section 103 or the display control section 105 for displaying various types of information on the display screen can also be stored in the storage section 107. Further, various parameters, which may become necessary to maintain when performing some process of the information processing apparatus 10, the progress of the processes or the like, or various databases or the like are appropriately stored in this storage section 107. This storage section 107 is configured so that each processing section included in the information processing apparatus 10 can freely read/write information.

(Details of the Intensity Correction Processing Section 103)

Here, the configuration of the intensity correction processing section 103 will be described in more detail with reference to FIG. 10.

The intensity correction processing section 103 provides a prior distribution for each base vector and noise vector upon formulating the measurement data, and estimates the base vector and noise vector in each measurement data (refer to FIG. 8). Afterwards, the intensity correction processing section 103 calculates the intensity coefficients in the equation shown in FIG. 8, by using the estimated base vectors and noise vectors.

Further, the intensity correction processing section 103 calculates a posteriori distribution of the base vector and noise vector in each measurement data, based on an initial value of the prior distribution such as described above, and updates the parameter type which represents the prior distribution by using the obtained posteriori distribution. In this way, the prior distribution of the base vectors or noise vectors used in the intensity correction process is frequently corrected so as to be suitable for the measurement data.

Here, the intensity correction processing section 103 may store in advance data related to a typical prior distribution in a database under consideration as a database in the storage section 107 or the like, and may use this typical data as an initial value of the prior distribution.

For example, in the case where the fluorescence spectrum of cells stained with various fluorescent dyes is under consideration, the fluorescence spectrum can be measured by using a simple staining sample of cells or beads by part or all of the fluorescent dyes, and the obtained fluorescence spectrum can be used as an initial value of the prior distribution. Further, it is also possible to use the fluorescence spectrum measured by using a mixture with a simple staining sample of cells or beads, or the fluorescence spectrum measured by using a sample of cells or beads subjected to multiple staining, as an initial value of the prior distribution.

The intensity correction processing section 103 may update the initial value of the prior distribution such as described above by using the posteriori distribution of the estimated base vectors, and may correct the initial value so that it becomes suitable for the measurement data. Note that when obtaining the prior distribution of the based vectors by using the mixture with the simple staining sample, it is preferable to select the combined fluorescent dyes so that the overlap of observation peaks in spectroscopic spectra of each corresponding fluorescent dye partially decreases.

Further, the intensity correction processing section 103 can stipulate not only the base vector of the fluorescent dye used to measure the fluorescence spectrum, but also a prior distribution for a fluorescence spectrum of a chip or an autofluorescence spectrum of cells, and can update this prior distribution. In this way, it is possible for the intensity correction processing section 103 to obtain a prior distribution, such as that of the fluorescence spectrum of a chip or an autofluorescence spectrum of cells, by a learning process.

For example, by using the fluorescence spectrum measured without flow to a chip or the fluorescence spectrum measured by flow of only a liquid used for flowing cells, the intensity correction processing section 103 corrects the stipulated prior distribution so as to become suitable for this measurement data. In this way, the intensity correction processing section 103 can obtain the prior distribution which represents the fluorescence spectrum of a chip.

Similarly, the intensity correction processing section 103 uses a fluorescence spectrum measured by flowing unstained cells to a chip, and corrects the stipulated prior distribution so as to become more suitable for the measurement data obtained by this measurement. By these processes, the intensity correction processing section 103 can obtain a prior distribution which represents the autofluorescence of cells.

Here, the intensity correction processing section 103 may not estimate the base vector in each measurement data, but may similarly estimate a base vector capable of being used in common for all measurement data, and calculate the intensity coefficient by using this base vector capable of being used in common. That is, the intensity correction processing section 103 may estimate the base vector capable of being used in common for all the measurement data, and may calculate the intensity coefficient by converting various parameters, which represent the obtained base vector, for each intensity correction process.

Note that hereinafter, the intensity correction processing section 103 will be specifically described with the use of mathematical expressions. In this case, measurement data (hereinafter, also called a measurement vector) of some event n (1≤n≤N) is represented by $y_n \in R^K$ (K is the number of channels of a photodetector). Further, a base vector of a half positive value corresponding to a factor i (1≤i≤M) is represented by $\varphi_{ni}$ ($\varphi_{ni} \geq 0$), and a coefficient (intensity coefficient) of the half positive value of the factor i is represented by $w_{ni}$ ($w_{ni} \geq 0$). In addition, a matrix in which the base vectors are arranged is represented by $\Phi_n = (\varphi_{n1}, \ldots, \varphi_{nM})$, and a vector in which the intensity coefficients are arranged is represented by $w_n = (w_{n1}, \ldots, w_{nM})^T$.

As shown in FIG. 10, the intensity correction processing section 103 mainly includes a parameter setting control section 111, an intensity coefficient/base vector estimation section 113, and a corrected intensity output section 115.

The functions of the parameter setting control section 111 are implemented by, for example, a CPU, a DSP, a ROM, a RAM and the like. The parameter setting control section 111 sets various parameters used in the intensity correction process, such as a parameter which represents a prior distribution of the base vectors and a parameter which represents a distribution of the noise vectors, and updates the values of these parameters according to the processing result by the intensity coefficient/base vector estimation section 113, which is described later.

Specifically, the parameter setting control section 111 sets a prior distribution of the base vector $\varphi_{ni}$ in an event n, such as in the following Equation (14), and sets the distribution of the noise vector $\varepsilon_n$, such as in the following Equation (15).

$$\varphi_{ni} \sim N_{\varphi ni \geq 0}(\mu_i, \Sigma_i) \quad (14)$$

$$\varepsilon_n \sim N(0, \mathrm{diag}(\lambda)^{-1}) \quad (15)$$

Here, the above Equation (14) has a probability density proportional to a normal distribution with a mean parameter $\mu_i$ and a covariance parameter $\Sigma_i$ in a range satisfying the base vector $\varphi_{ni} \geq 0$, and represents a truncated normal distribution having no probability density in other ranges. Further, in the above Equation (15), $\lambda = (\lambda_1, \ldots, \lambda_K)^T$ represents the variance of each photodetector. The above Equation (15) represents setting an independent variance parameter $\lambda_k$ in each photodetector. By considering the variance in this way, in the case when the sensitivities of the photodetectors are different from each other, it is possible to implement the intensity correction process in which the differences of the sensitivities of the photodetectors are considered.

A probability model is created of a measurement vector $y_n$ corresponding to the measurement data, as in the following Equation (16), by the parameter setting control section 111 setting the base vector and the noise vector, as in the above Equation (14) and Equation (15).

$$y_n \sim N_{y_n = 0}(\Phi_n w_n, \mathrm{diag}(\lambda)^{-1}) \quad (16)$$

Note that the parameter setting control section 111 may not set the prior distribution of the base vector $\varphi_{ni}$ based on Equation (14), and may, as described previously, use various spectrum data stored in various databases or various spectra measured in advance as the prior distribution of the base vector $\varphi_{ni}$.

The parameter setting control section 111 updates the parameters and the noise vectors of the prior distributions, by using $w_n$ or $\Phi_n$ calculated by the intensity coefficient/base vector estimation section 113, which is described later. Specifically, the parameter setting control section 111 updates the noise vectors based on the following Equation (17).

$$\lambda_k^{-1} = \frac{1}{N} \sum_{n=1}^{N} (y_{nk} - \varphi_{nk}^T w_n)^2 \quad (17)$$

$T_{nk}$: Element of the $k^{th}$ row of $\Phi_n$

Further, the parameter setting control section 111 updates the mean parameter $\mu_i$ and the covariance parameter $\Sigma_i$, which are parameters of the prior distribution, by a method such as type II maximum likelihood estimation. While it is possible for an updating method of the mean parameter and the covariance parameter $\Sigma_i$ to be appropriately set, the parameter setting control section 111 can update, for example, the mean parameter and the covariance parameter $\Sigma_i$ so that an expected value E related to $\{\varphi_{ni}\}_{n=1 \sim N}$, represented by the following Equation (18) and Equation (19), is maximized.

In the case where updating of the parameters is performed based on the following Equation (18), all of the base vectors $\varphi_{ni}$ are similarly reflected for the parameters $\mu_i$ and $\Sigma_i$. However, as described later, since the intensity coefficient vector $w_n$ is subjected to an estimation process under the restriction of $w_n \geq 0$, the case where the intensity coefficient $w_{ni} = 0$ can be considered to occur many times. In such a case, the mean of the base vectors $\varphi_{ni}$ remains $\mu_i$. Further, even in the case where the value of the intensity coefficient $w_{ni}$ is small, the mean of the base vectors $\varphi_{ni}$ remains $\mu_i$.

Therefore, in the case where the base vectors $\varphi_{ni}$ are used uniformly in the updating process, there is the possibility that the prior distribution may be strongly dependent on an initial value. Accordingly, the parameter setting control section 111 may update the mean parameter and the covariance parameter $\Sigma_i$ so that the weighted estimated value E is maximized with the intensity coefficient $w_{ni}$, as shown in the following Equation (19). Further, in methods other than this method, the parameter setting control section 111 may also set a prescribed value multiplied by the maximum value of $\{w_{ni}\}_{n=1 \sim N}$ as a threshold value, and perform an updating process by using only an intensity coefficient equal to or more than the threshold value.

$$E\left[\sum_{n=1}^{N} \ln p\left(\phi_{ni} \mid \mu_i, \sum_i\right)\right] \quad (18)$$

$$E\left[\sum_{n=1}^{N} w_{ni} \ln p\left(\phi_{ni} \mid \mu_i, \sum_i\right)\right] \quad (19)$$

The intensity coefficient/base vector estimation section 113, which is an example of an estimation section, is implemented by, for example, a CPU, a DSP, a ROM, a RAM and the like. The intensity coefficient/base vector estimation section 113 estimates a likely intensity coefficient corresponding to the measurement vector $y_n$, and estimates the base vector, based on the measurement vector $y_n$ corresponding to the measurement data and the parameters (the parameters related to the base vector and noise vector) set by the parameter setting control section 111.

Further, when estimated values of the intensity coefficient and parameters of the base vector are obtained, the intensity coefficient/base vector estimation section 113 performs convergence determination which determines whether or not the obtained estimated values converge. In the case where it is determined that the obtained estimated values do not converge, the intensity coefficient/base vector estimation section 113 outputs the obtained estimated values to the parameter setting control section 111, and requests an update of various parameters. Moreover, the intensity coefficient/base vector estimation section 113 again estimates the intensity coefficient and base vector by using the updated various parameters.

The intensity coefficient/base vector estimation section 113 can estimate the likely intensity coefficient corresponding to the measurement vector, and can estimate the base vector, with high accuracy by repeatedly performing the operation such as described above.

Further, in the case where the obtained estimated values converge, the intensity coefficient/base vector estimation section 113 outputs the obtained estimated values of the intensity coefficient to the corrected intensity output section 115, which is described later.

It is possible for the intensity coefficient/base vector estimation section 113 to use a well-known method, such as MAP (Maximum A Posteriori) estimation, various Bayesian estimations such as Bayesian estimation or variational Bayesian estimation based on sampling, maximum likelihood estimation or the like as the method used for estimating the intensity coefficient and the base vector.

Note that during the process, while it is possible to use the base vector estimated by MAP estimation or the like as it is, a method can also be considered which uses the base vector to which prescribed normalization is applied. For example, a method which normalizes by the maximum value or an integral value of the fluorescence spectrum, and a method which normalizes by the norm (for example, the Euclidean norm) of the base vector, can be considered as a method of normalization.

Hereinafter, a specific description will be made for an example case where the intensity coefficient/base vector estimation section 113 performs estimation by using MAP estimation.

First, the intensity coefficient/base vector estimation section 113 performs MAP estimation for $\{w_n, \Phi_n\}_{n=1 \sim N}$ and $\lambda$ set by the parameter setting control section 111. In this case, the simultaneous distribution considered by the intensity coefficient/base vector estimation section 113 is represented as in the following Equation (20).

$$p\left(\{y_n, w_n, \Phi_n\}_{n=1}^{N}, \lambda \mid \{\mu_i, \sum_i\}_{i=1}^{M}\right) = \quad (20)$$

$$\prod_{n=1}^{N} (p(y_n \mid \Phi_n, w_n, \lambda) \prod_{i=1}^{M} p(\phi_{ni} \mid \mu_i, \sum_i))$$

Here, when the logarithm of the above Equation (20) is taken and the item related to the intensity coefficient vector $w_n$ is under consideration, the following Equation (21) can be obtained. Here, since $w_n \geq 0$, the intensity coefficient/base vector estimation section 113 can obtain an optimum intensity coefficient vector $w_n$ which satisfies the above Equation (20) and the following Equation (21), by solving a quadratic programming problem represented by the following Equation (22) under the restriction of $w_n \geq 0$.

$$\ln p(\{y_n, w_n, \Phi_n\}_{n=1}^{N}, \lambda \mid \{\mu_i, \Sigma_i\}_{i=1}^{M}) = -\frac{1}{2}\{w_n^T(\Phi_n^T \operatorname{diag}(\lambda)\Phi_n)w_n - 2y_n^T \operatorname{diag}(\lambda)\Phi_n w_n\} + \text{const.} \quad (21)$$

$$\hat{w}_n = \arg\min_{\Phi_n w_n} w_n^T(\Phi_n^T \operatorname{diag}(\lambda)\Phi_n)w_n - 2y_n^T \operatorname{diag}(\lambda)\Phi_n w_n \quad (22)$$

Further, when the logarithm of the above Equation (20) is taken and the item related to a base vector matrix $\Phi_n$ is under consideration, the following Equation (23) can be obtained. Here, in the following Equation (20), $\operatorname{diag}(\lambda)$ is a diagonal matrix which has $\lambda$ in a diagonal component, $\operatorname{diag}(\Sigma_1^{-1}, \ldots, \Sigma_M^{-1})$ is a block diagonal matrix which has $\Sigma_1^{-1}, \ldots, \Sigma_M^{-1}$ in a diagonal component, and $I_K$ is a K-dimensional unit matrix. Further, in the following Equation (23), $\operatorname{vec}(\Phi_n)$ is a vector represented by the following Equation (24), and $\mu$ is a vector represented by the following Equation (25).

$$\ln p\left(\{y_n, w_n, \Phi_n\}_{n=1}^{N}, \lambda \mid \{\mu_i, \sum_i\}_{i=1}^{M}\right) = \quad (23)$$

$$-\frac{1}{2}\left\{\begin{array}{c}(y_n - (w_n^T \otimes I_K)\operatorname{vec}(\Phi_n))^T \operatorname{diag}(\lambda)(y_n - (w_n^T \otimes I_K)\operatorname{vec}(\Phi_n)) + \\ (\operatorname{vec}(\Phi_n) - \mu)^T \operatorname{diag}\left(\sum_1^{-1}, \ldots, \sum_M^{-1}\right)(\operatorname{vec}(\Phi_n) - \mu)\end{array}\right\} =$$

$$-\frac{1}{2}\left[\begin{array}{c}\operatorname{vec}(\Phi_n)^T \left\{\begin{array}{c}(w_n^T \otimes I_K)^T \operatorname{diag}(\lambda)(w_n^T \otimes I_K) + \\ \operatorname{diag}\left(\sum_1^{-1}, \ldots, \sum_M^{-1}\right)\end{array}\right\} \\ \operatorname{vec}(\Phi_n) - 2\left\{\begin{array}{c}(w_n^T \otimes I_K)^T \operatorname{diag}(\lambda)y_n + \\ \operatorname{diag}\left(\sum_1^{-1}, \ldots, \sum_M^{-1}\right)\mu\end{array}\right\}^T \operatorname{vec}(\Phi_n)\end{array}\right]$$

-continued ($\otimes$: Kroneckerproduct) (24)

$$vec(\Phi_n) = \begin{pmatrix} \phi_{n1} \\ \vdots \\ \phi_{nM} \end{pmatrix}$$

$$\mu = \begin{pmatrix} \mu_1 \\ \vdots \\ \mu_M \end{pmatrix} \quad (25)$$

Here, since $\Phi_n \geq 0$, the intensity coefficient/base vector estimation section 113 can obtain an optimum intensity coefficient vector $\Phi_n$ which satisfies the above Equation (20) and Equation (23), by solving a quadratic programming problem represented by the following Equation (26) under the restriction of $\Phi_n \geq 0$.

$$vec(\hat{\Phi}_n) = \underset{vec(\Phi_n)}{\operatorname{argmin}} vec(\Phi_n)^T \quad (26)$$

$$\left\{ (w_n^T \otimes I_K)^T \operatorname{diag}(\lambda)(w_n^T \otimes I_K) + \operatorname{diag}\left( \sum_1^{-1}, \ldots, \sum_M^{-1} \right) \right\} vec(\Phi_n) -$$

$$2 \left\{ (w_n^T \otimes I_K)^T \operatorname{diag}(\lambda) y_n + \operatorname{diag}\left( \sum_1^{-1}, \ldots, \sum_M^{-1} \right) \mu \right\}^T vec(\Phi_n)$$

The corrected intensity output section 115 is implemented by, for example, a CPU, a ROM, a RAM, a communication device and the like. The corrected intensity output section 115 outputs the intensity coefficient after converging $w_{ni}$, which is notified from the intensity coefficient/base vector estimation section 113, as an intensity after the intensity correction process of the measurement data under consideration (a corrected intensity).

For example, the corrected intensity output section 115 inputs the intensity coefficient $w_{ni}$ notified from the intensity coefficient/base vector estimation section 113 to the display control section 105, and outputs the corrected intensity to the user via a display screen by the display control section 105. Further, the corrected intensity output section 115 may output the corrected intensity to the user via an output device such as a printer, or may output data which represents the corrected intensity to various recording media such as a CD, DVD, or Blu-ray disc, or to a USB memory. Further, the corrected intensity output section 115 may output the data which represents the obtained corrected intensity to an external apparatus capable of communicating with the information processing apparatus 10 via various communication networks.

Heretofore, the configuration of the intensity correction processing section 103 has been described with reference to FIG. 10.

Note that while an example of the case where the prior distribution of the base vectors or noise vectors is set as a normal distribution is included in the above description, the prior distribution may be a distribution other than a normal distribution, such as a Student-t distribution or a Laplace distribution.

Further, in the case where the intensity correction process such as described above is performed for the fluorescence spectrum of cells, since the autofluorescence of the cells can be considered to be different for each type of cell, the prior distribution of the base vectors corresponding to the autofluorescence of the cells may be set as a mixed distribution.

In this way, it becomes possible to perform an estimation process which estimates the autofluorescence of the cells while estimating the type of cells.

Here, the mixed distribution used in the prior distribution of the base vectors corresponding to the autofluorescence of the cells can be generated by processing a measurement vector group, which is measured using an unstaining cell group, by an EM (Expectation Maximization) algorithm, a variational Bayesian estimation algorithm, or clustering.

Further, while an intensity correction process according to the present embodiment has been specifically described in the above described description, by an example of a fluorescence spectrum of cells subjected to multiple staining, it is also possible for the intensity correction process according to the present embodiment to be applied to a spectrum other than a fluorescence spectrum of cells subjected multiple staining.

For example, it is also possible for the intensity correction method according to the present embodiment to be applied to a case where a mixture, in which a plurality of compounds are considered to be mixed, is under consideration, and intensity correction is performed on the fluorescence spectrum, an absorption spectrum, a scattering spectrum or the like of such a mixture, by using a well-known spectrum database of a compound. In this case, the corrected intensity obtained by the intensity correction method according to the present embodiment corresponds to a quantitative analysis result which shows how much of a corresponding compound is included.

Further, in the intensity correction method according to the present embodiment, since estimation of the base vector is performed based on a measured spectrum using a well-known spectrum database or the like, it becomes possible to obtain not only the quantitative analysis described above, but also knowledge related to which compound is mixed (that is, a quantitative analysis of the mixed compound).

Heretofore, an example configuration of the information processing apparatus 10 has been described. However, the functions related to the masking process have not been referred to here. The functional configuration related to the masking process will be described in detail later. Note that each of the above described structural elements may be configured by using general members or circuits, or may be configured by hardware specialized for the functions of each structural element. Further, the functions of each structural element may all be performed by a CPU or the like. Therefore, it is possible to arbitrarily modify the configuration to be used according to the technical level when the present embodiment is implemented.

Note that it is possible for a computer program configured to implement each function of the information processing apparatus according to the present embodiment such as described above to be developed, and mounted on a personal computer or the like. Further, a computer readable recording medium storing such a computer program can also be provided. The recording medium is, for example, a magnetic disk, an optical disc, a magneto-optical disc, or a flash memory. Further, the above described computer program may be delivered via a network, for example, without using the recording medium.

2-3 Process Flow

Figure 11:
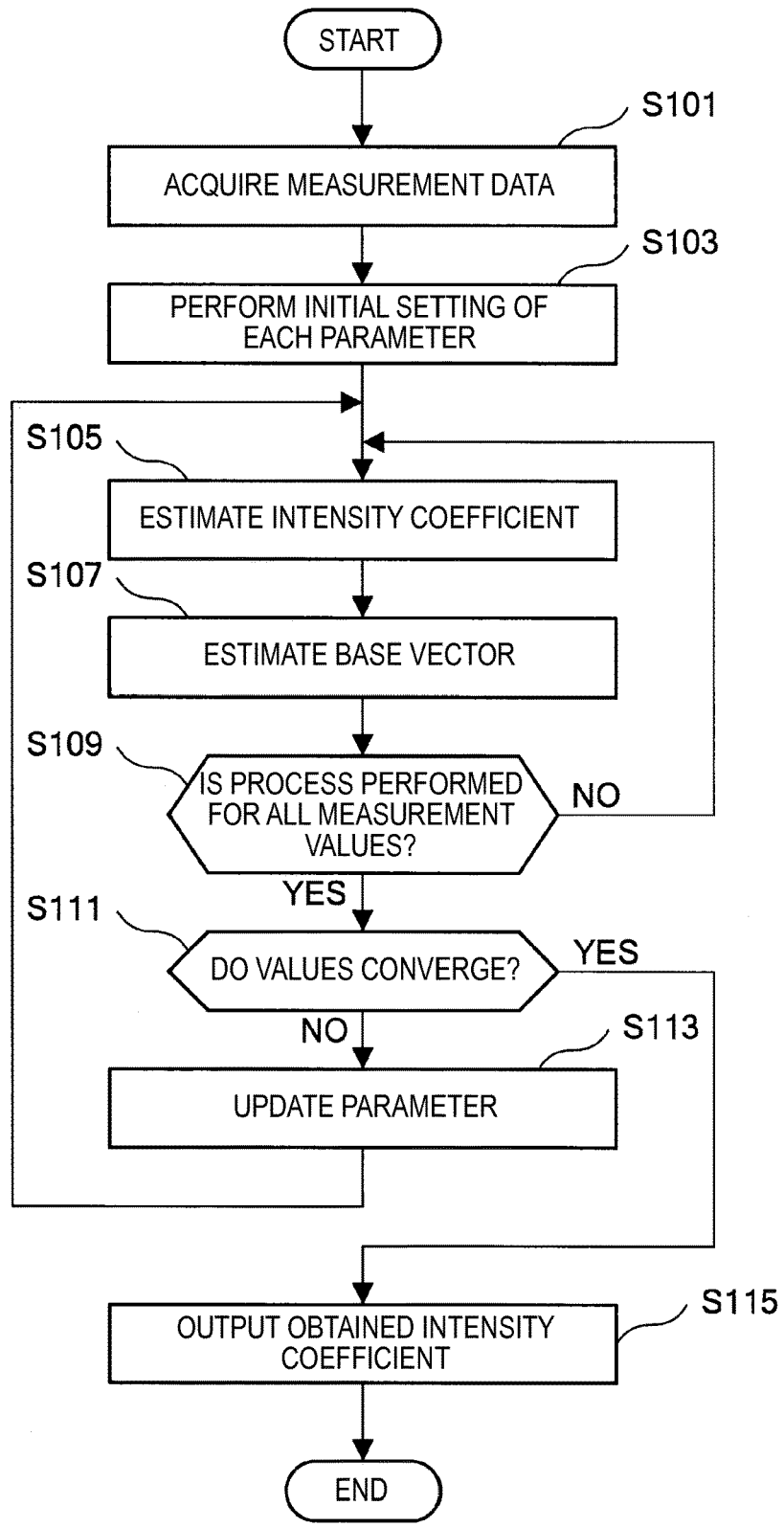
FIG. 11 is a flow chart which shows an example of the flow of an information processing method according to the first embodiment.

Next, the flow of the intensity correction method according to the present embodiment will be described with reference to FIG. 11. FIG. 11 is a flow chart which shows the flow of the intensity correction process according to the present embodiment. This intensity correction process is implemented mainly by each functional block of the information processing apparatus 10.

As shown in FIG. 11, first the measurement data acquisition section 101 acquires data (measurement data) of the spectrum measured by the measurement unit 20 (step S101), and outputs the obtained measurement data to the intensity correction processing section 103.

Next, the parameter setting control section 111 of the intensity correction processing section 103 performs initial setting of the parameters related to the base vectors and noise vectors (step S103), and outputs information related to each set parameter to the intensity coefficient/base vector estimation section 113.

The intensity coefficient/base vector estimation section 113 estimates the intensity coefficient by the above Equation (22), for example, by using measurement data notified from the measurement data acquisition section 101 and the various parameters set by the parameter setting control section 111 (step S105). Further, the intensity coefficient/base vector estimation section 113 estimates the base vector by the above Equation (26), for example, by using measurement data notified from the measurement data acquisition section 101 and the various parameters set by the parameter setting control section 111 (step S107).

Here, the intensity coefficient/base vector estimation section 113 judges whether or not the process is performed for all the measured values (step S109). In the case where the process is not performed for all the measured values, the intensity coefficient/base vector estimation section 113 continues the process by returning to step 105. On the other hand, in the case where the process is performed for all the measured values, the intensity coefficient/base vector estimation section 113 judges whether or not the obtained estimated values converge (step S111).

In the case where the obtained estimated values do not converge, the intensity coefficient/base vector estimation section 113 outputs the obtained estimated values to the parameter setting control section 111. The parameter setting control section 111 updates the parameters related to the base vectors and noise vectors, by using the notified estimated values (step S113), and outputs the parameters after updating to the intensity coefficient/base vector estimation section 113. The intensity coefficient/base vector estimation section 113 uses the parameters after updating, and continues the process by returning again to step S105.

Further, in the case where the estimated values converge, the intensity coefficient/base vector estimation section 113 outputs the obtained intensity coefficient to the corrected intensity output section 115. The corrected intensity output section 115 outputs the intensity coefficient output from the intensity coefficient/base vector estimation section 113 as the intensity after correction processing (that is, the genuine intensity) (step S115). In this way, it becomes possible for the user to understand the intensity correction processing result related to the spectrum under consideration.

Heretofore, the overall flow of the intensity correction process according to the present embodiment has been described.

Specific Application Example

Figure 12:
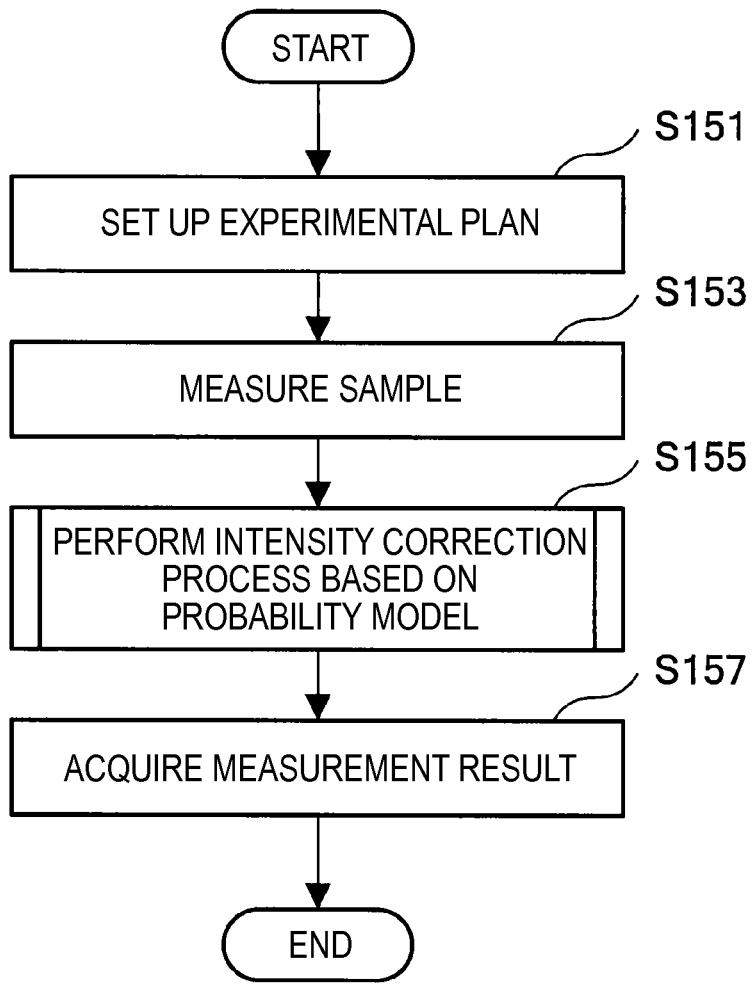
FIG. 12 is a flow chart which shows an example of the flow of a fluorescence intensity correction process using the information processing method according to the first embodiment.
Figure 13:
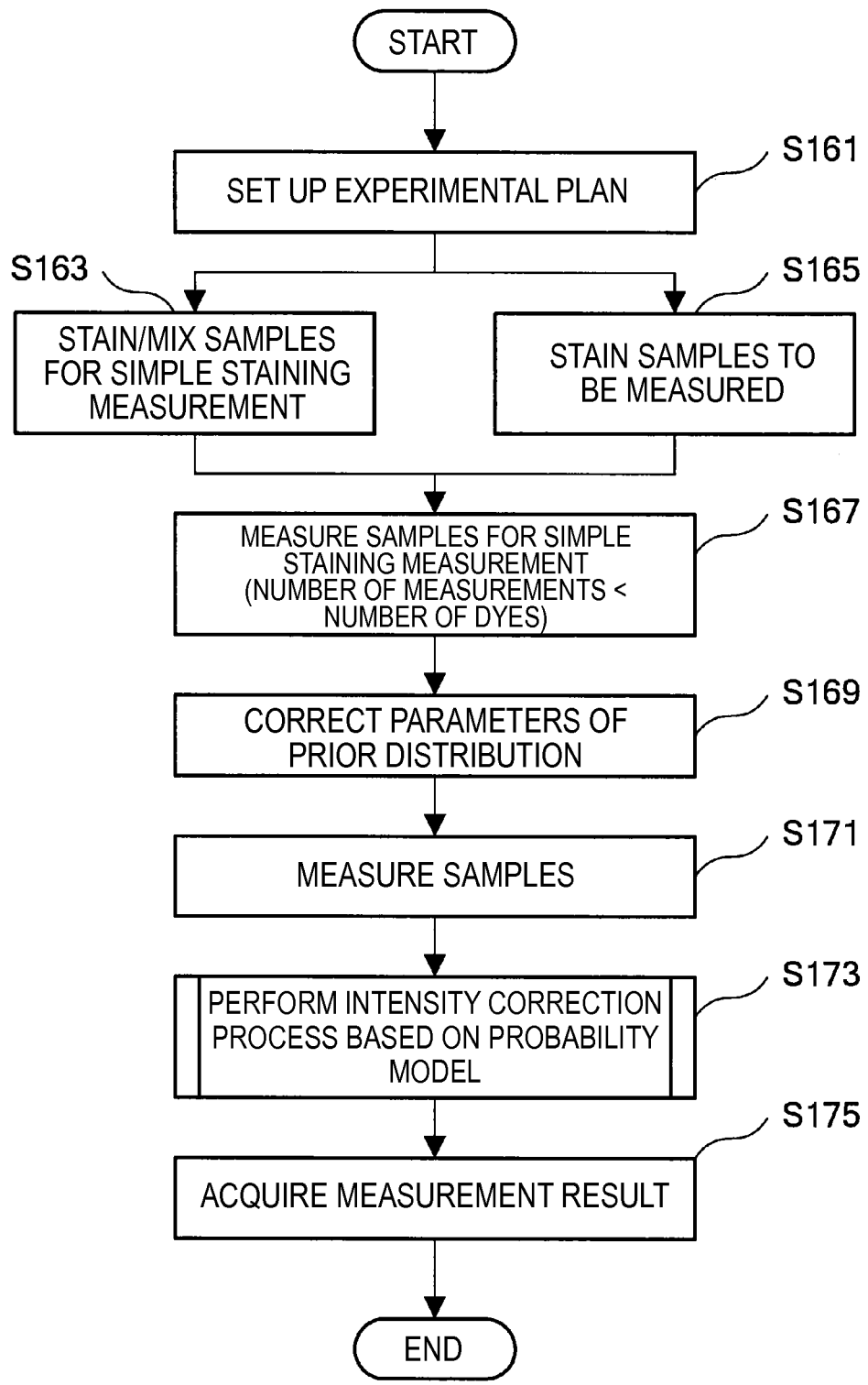
FIG. 13 is a flow chart which shows an example of the flow of a fluorescence intensity correction process using the information processing method according to the first embodiment.

Here, a case in which the above described intensity correction process is applied to a fluorescence spectrum of cells subjected multiple staining will be described with reference to FIGS. 12 to 15. FIGS. 12 and 13 are flow charts which show the flow of the fluorescence intensity correction process using the intensity correction method according to the present embodiment.

First, the flow of the case where the fluorescence spectrum of the simple staining sample is not measured will be described with reference to FIG. 12.

In the case where the intensity correction method according to the present embodiment is used, the measurer of the fluorescence spectrum first sets up an experimental plan for how to perform multiple staining for the cells to be measured by using a fluorescent dye (step S151), and performs multiple staining of the cells to be measured. As well as this, the measurer of the fluorescence spectrum measures the fluorescence spectrum of the cells subjected to multiple staining by using a flow cytometer, such as shown in FIGS. 6 and 7 (step S153).

The measurer of the fluorescence spectrum transmits the measurement data output from the flow cytometer, such as shown in FIGS. 6 and 7, to the information processing apparatus 10, such as shown in FIGS. 9 and 10. The information processing apparatus 10 according to the present embodiment performs the intensity correction process based on the above described probability model while using a database or the like related to the fluorescence characteristics of the fluorescent dyes (step S155), and outputs the obtained intensity correction processing result. In this way, the measurer of the fluorescence spectrum can acquire the value of the fluorescence intensity (that is, the measurement result of the fluorescence spectrum) originating from each fluorescent dye (step S157).

The intensity correction processing method according to the present embodiment corrects the base vector corresponding to the fluorescence spectrum in the case where each fluorescent dye is used independently, by using the measurement result measured by a measurement unit such as a flow cytometer. Accordingly, by using the intensity correction method according to the present embodiment, an intensity correction process is performed which automatically reflects information in the case where a sample of cells or the like under consideration is subjected to simple staining, and the accuracy of the calculated correction intensity can be improved.

Next, the flow of the process in the case where the fluorescence spectrum of the simple staining sample is performed will be described with reference to FIG. 13.

In the case where the intensity correction method according to the present embodiment is used, the measurer of the fluorescence spectrum first sets up an experimental plan for how to perform multiple staining for cells to be measured by using a fluorescent dye (step S161). Afterwards, the measurer of the fluorescence spectrum prepares a mixed sample by mixing several simple staining samples obtained after the samples are stained for performing simple staining measurement (step 163), and also performs multiple staining for the samples to be measured (step S165).

Afterwards, the measurer of the fluorescence spectrum measures the fluorescence spectrum of this sample with the flow cytometer, such as shown in FIGS. 6 and 7, by using the samples for the simple staining measurement prepared in step S163 (step S167). At this time, in the case where the intensity correction method according to the present embodiment is used, since a mixed sample is used in which several simple staining samples are mixed, the number of measurements of the sample for the simple staining measurement can be set to be less than the number of fluorescent dyes to be used in the multiple staining of the cells.

When the measurement of the sample for the simple staining measurement is completed, the measurer of the fluorescence spectrum transmits the obtained measurement result of the sample for simple staining measurement to the information processing apparatus 10, such as shown in FIGS. 9 and 10. The information processing apparatus 10 corrects the contents of the prior distribution parameters by using the input measurement result, so as to be suitable for the cells under consideration (step S169).

After performing pre-processing such as described above, the measurer of the fluorescence spectrum measures the fluorescence spectrum of the multiple staining cells under consideration, by using the flow cytometer or the like, such as shown in FIGS. 6 and 7 (step S171). The measurer of the fluorescence spectrum transmits the measurement data output from the flow cytometer used in the measurement to the information processing apparatus 10, such as shown in FIGS. 9 and 10.

The information processing apparatus 10 performs the intensity correction process based on the above described probability model by using the corrected prior distribution parameters and measurement data (step S173), and outputs the obtained intensity correction processing result. In this way, the measurer of the fluorescence spectrum can acquire the value of the fluorescence intensity (that is, the measurement result of the fluorescence spectrum) originating from each fluorescent dye (step S175).

(Generation Process of the Base Vectors)

Figure 14:
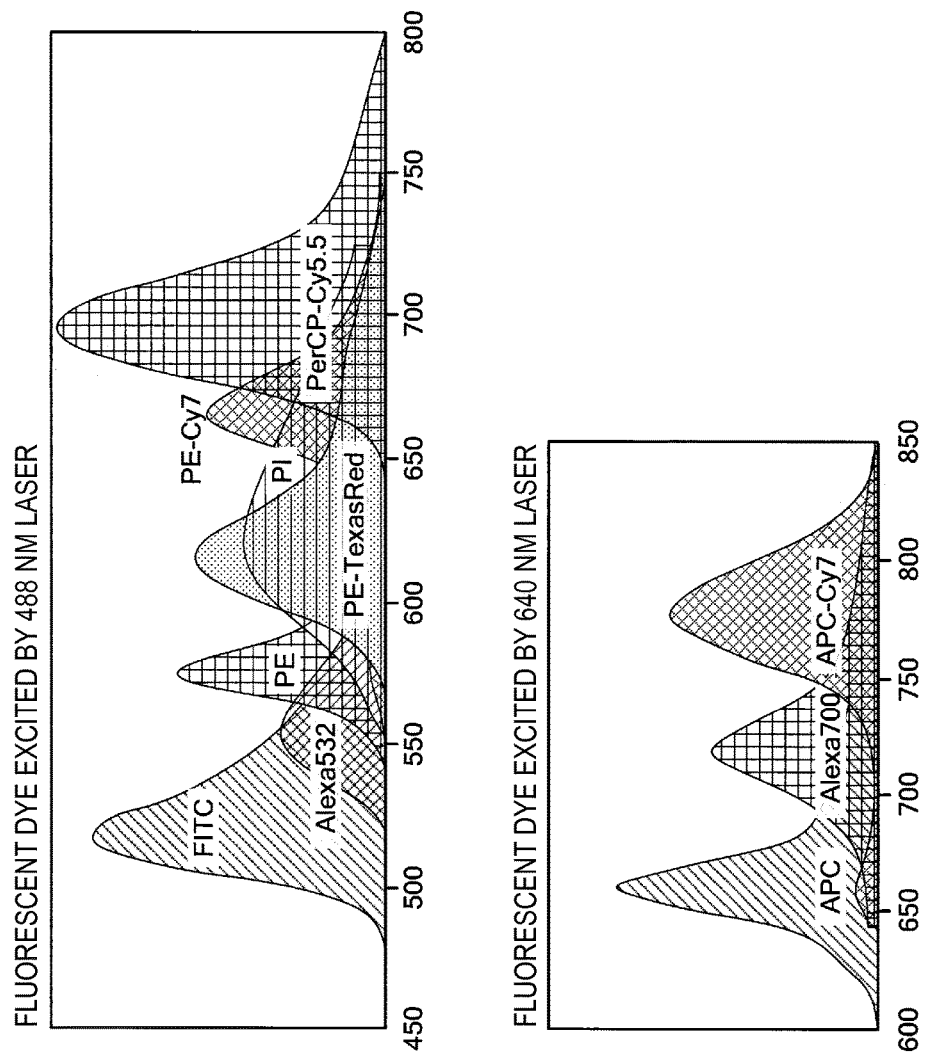
FIG. 14 is an explanatory diagram for describing a generation process of base vectors using the information processing method according to the first embodiment.
Figure 15:
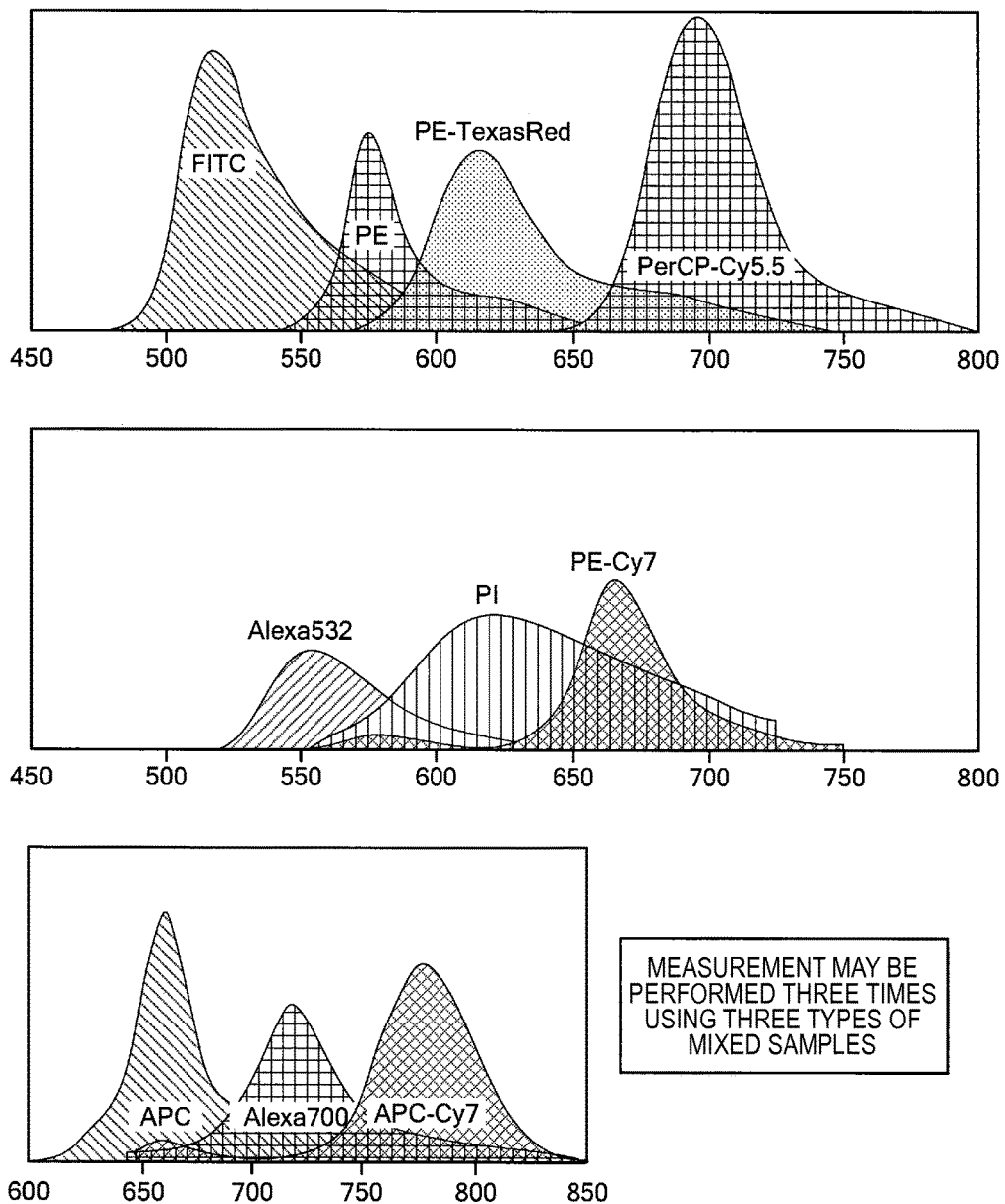
FIG. 15 is an explanatory diagram for describing a generation process of base vectors using the information processing method according to the first embodiment.

Here, the generation process of base vectors will be described with reference to FIGS. 14 and 15. FIGS. 14 and 15 are explanatory diagrams for describing the generation process of base vectors using the information processing method according to the present embodiment.

As shown in FIG. 14, a case will be considered where a sample is subjected to multiple staining by using a total of ten types of fluorescent dyes, with seven of the types of fluorescent dyes excited by a laser beam of 480 nm and three of the types of fluorescent dyes excited by a laser beam of 640 nm. With reference to FIG. 14, it can be understood in this example that the seven types of fluorescent dyes excited by a laser beam of 480 nm have several peak overlaps which show the fluorescence characteristics.

In the case where the intensity correction method according to the present embodiment is not used, it may be necessary to prepare ten types of simple staining samples using each fluorescent dye and perform the measurement ten times in order to generate the base vectors of these ten types of fluorescent dyes. However, by using the intensity correction method according to the present embodiment, the simple staining spectrum can be measured by using a combined mixed sample so that the peak overlaps are reduced in the measured fluorescence spectrum.

Specifically, as shown in FIG. 15, for example, the prior distribution to be used as the base vector can be generated from the actual measurement spectrum, by preparing three types of mixed samples upon considering the combination of the fluorescent dyes in which the peak wavelengths do not mutually overlap one another, and by performing the measurement a total of three times. In this way, by using the intensity correction method according to the present embodiment, the time or cost which may be necessary for obtaining the measurement result of the simple staining sample can be considerably reduced.

2-4: Example

Here, an example is shown.

In the example shown hereinafter, the usability of the information processing method (intensity correction method) according to the present embodiment will be examined, by producing a mixed sample using blood gathered from two different people, and by using data of the fluorescence spectrum measured upon performing multiple staining on this mixed sample with three types, FITC, Alexa 532, and PE, of fluorescent dyes.

Figure 16:
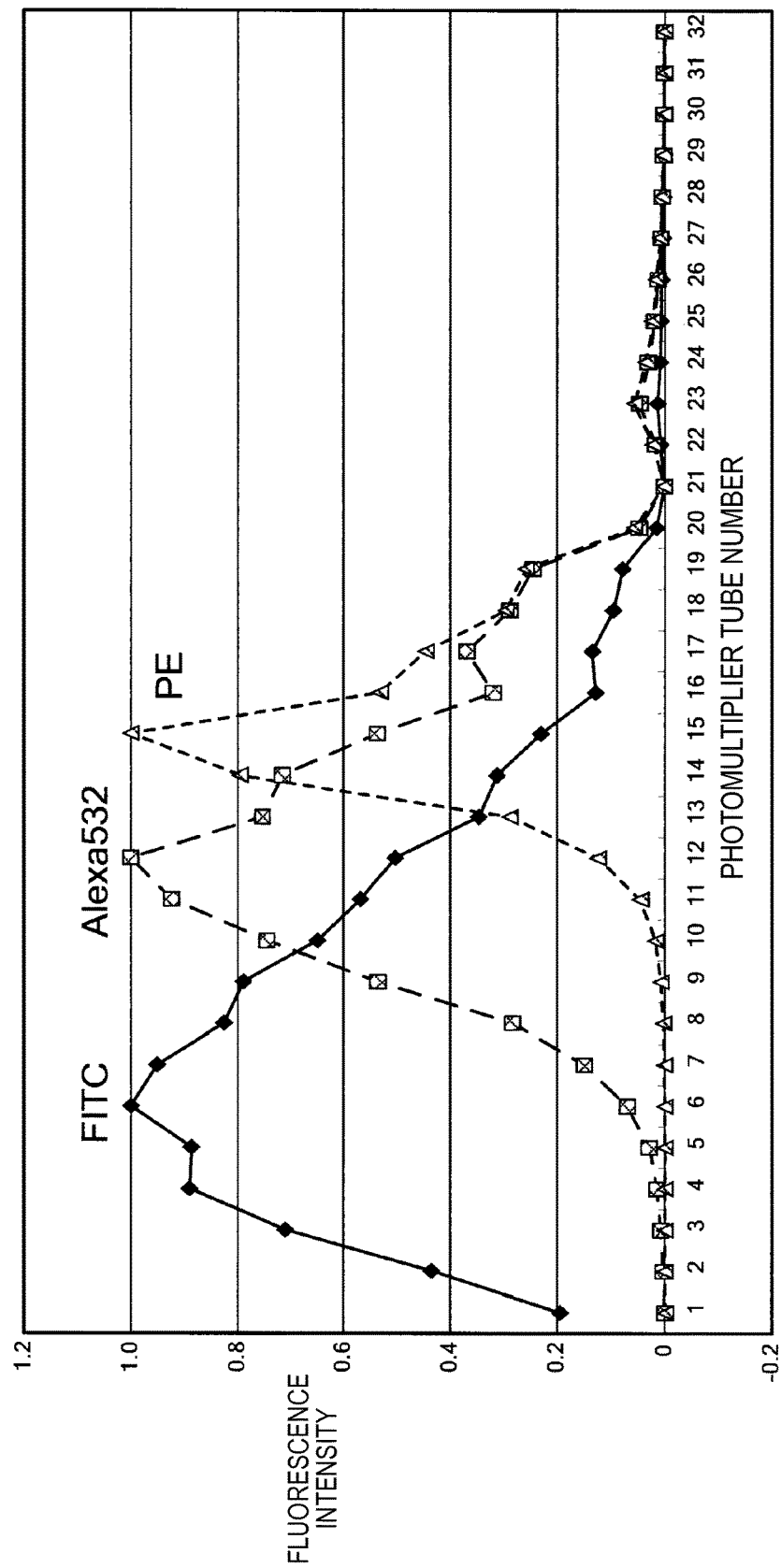
FIG. 16 is a graph chart which shows the fluorescence characteristics of fluorescent dyes used to dye a mixed sample.

FIG. 16 is a graph chart which shows the fluorescence characteristics of the fluorescent dyes used to stain the mixed sample. The fluorescence characteristics shown in FIG. 16 were measured by using the flow cytometer shown in FIGS. 6 and 7. Here, the horizontal axis of the graph chart shown in FIG. 16 corresponds to the number given to the photomultiplier tubes mounted in the flow cytometer used for the measurement, and corresponds to the wavelength of the fluorescence spectrum. Further, the vertical axis of the graph chart represents the fluorescence intensity.

Here, as is evident from the results shown in FIG. 16, it can be understood that the peaks which represent each of the fluorescence characteristics of the three types of fluorescent dyes, FITC, Alexa 532, and PE, mutually overlap one another. From the graph chart of FIG. 16, it can be said that a combination of such three types of fluorescent dyes is a combination of the fluorescent dyes for which the calculation of the genuine fluorescence intensity is difficult.

Hereinafter, the usability of the information processing method (intensity correction method) according to the present embodiment will be examined, by comparing a case where the base vectors measured by simple staining cells are used with a case where the base vectors measured by simple staining latex beads are used.

Note that, hereinafter, the base vector measured by performing simple staining on the cells will be called a cell simple staining base vector or a cell simple staining prior distribution, and the base vector measured by performing simple staining on the latex beads will be called a bead simple staining base vector or a bead simple staining prior distribution.

Figure 17:
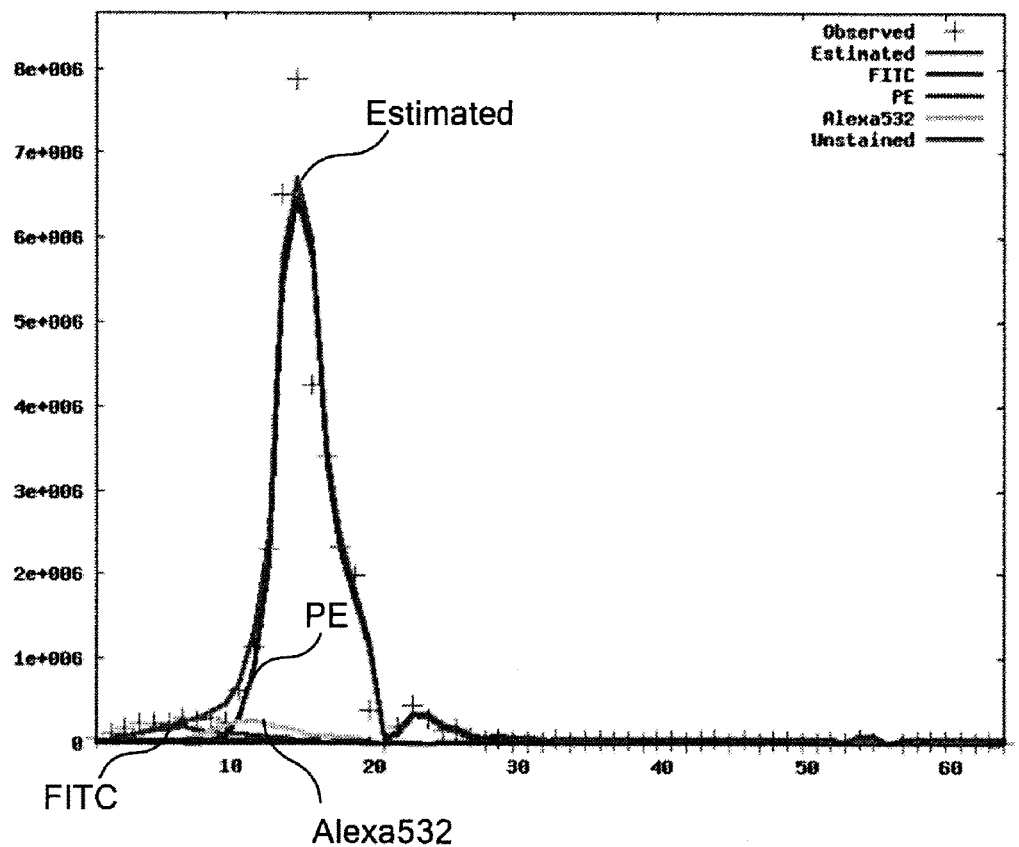
FIG. 17 is a graph chart which shows a fitting state of measurement data.
Figure 18:
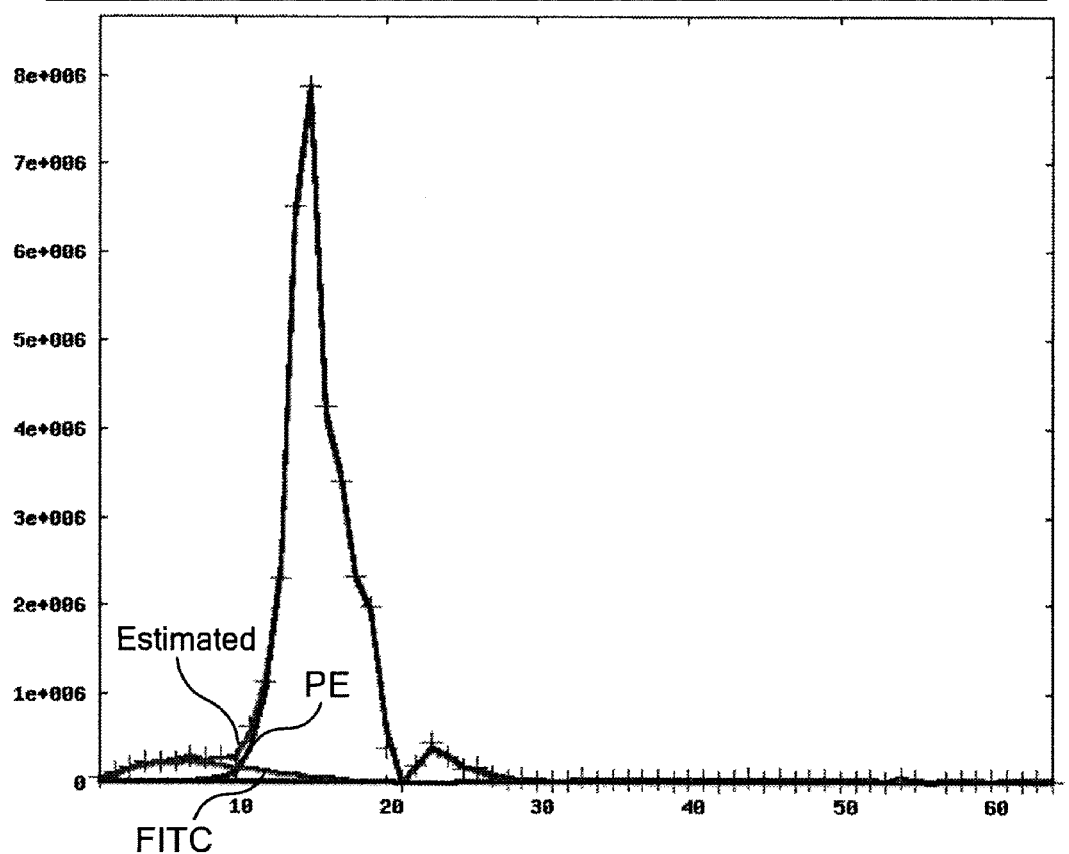
FIG. 18 is a graph chart which shows a fitting state of measurement data.
Figure 19:
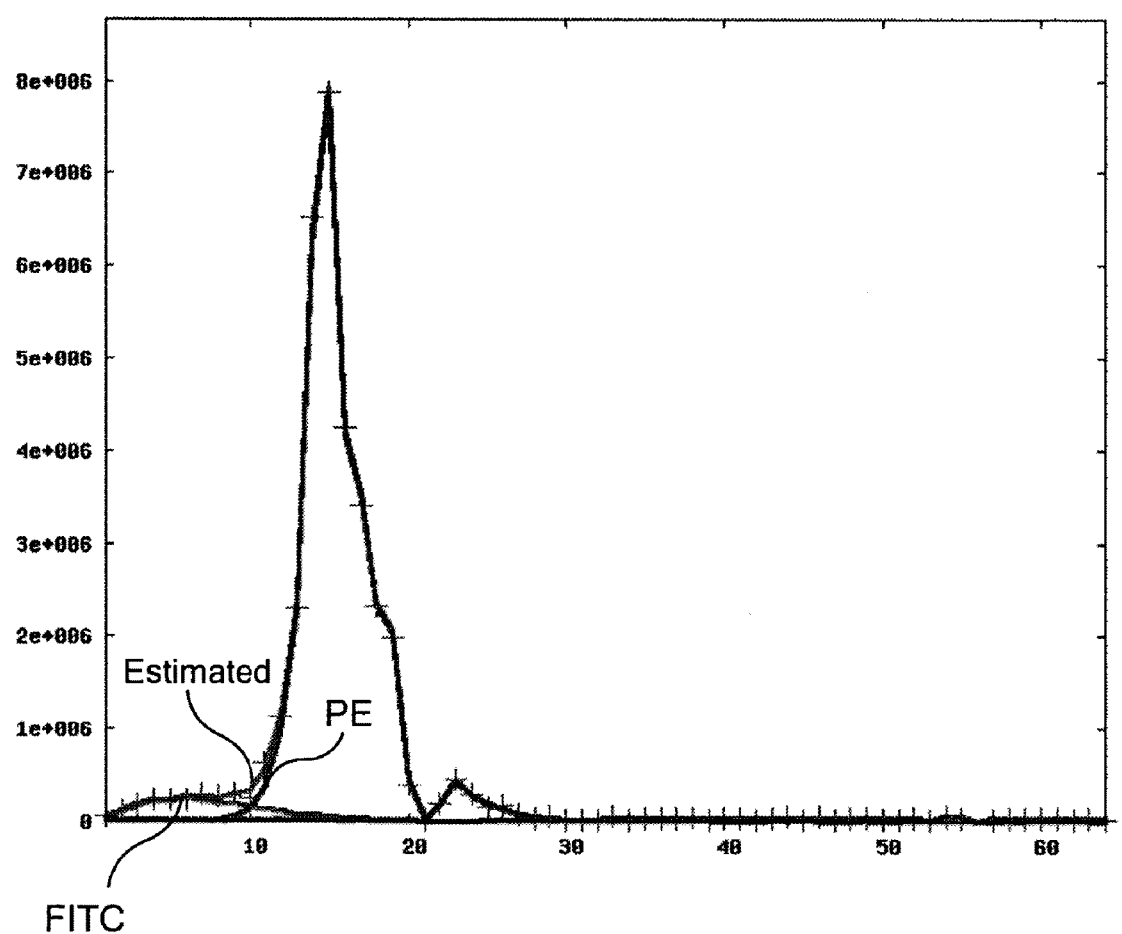
FIG. 19 is a graph chart which shows a fitting state of measurement data.

FIGS. 17 to 19 show a state of fitting the measurement results of the fluorescence spectrum measured upon performing multiple staining the mixed sample as described above by using the respective base vectors.

FIG. 17 shows a state of fitting the measurement data by the restricted least square method, such as shown by example in FIGS. 3 and 4, by using the bead simple staining base vector. As is evident when referring to FIG. 17, it can be understood that the approximate curve (the curve represented by "Estimated" in the figure) obtained by the least square method is not able to reproduce an actually measured fluorescence spectrum. Further, when the base vectors used for calculating the approximate curve are under consideration, it can be understood that the base vector related to Alexa 532 is used in addition to the base vector related to FITC and the base vector related to PE.

FIG. 18 shows a state of fitting the measurement data by the restricted least square method, by using the cell simple staining base vector. When referring to FIG. 18, it can be understood that the approximate curve (the curve represented by "Estimated" in the figure) obtained by the least square method can reproduce an actually measured fluorescence spectrum. Further, when the base vectors used for calculating the approximate curve are under consideration, it can be understood that the base vector related to FITC and the base vector related to PE are mainly used, and the base vector related to Alexa 532 is not used.

As is evident when comparing FIGS. 17 and 18 with each other, in order to fit the measurement data by the restricted least square method, the use of the cell simple staining base vector, which may necessitate a time and cost to generate the base vector, rather than the bead simple staining base vector, is sought after.

Further, FIG. 19 shows a state of fitting the measurement data by the fluorescence intensity correction method according to the present embodiment, by using the bead simple staining base vector. When referring to FIG. 19, it can be understood that the approximate curve (the curve represented by "Estimated" in the figure) can reproduce the actually measured fluorescence spectrum. Further, when the base vectors used for calculating the approximate curve are under consideration, it can be understood that the base vector related to FITC and the base vector related to PE are mainly used, and the base vector related to Alexa 532 is not used.

In this way, when applying the fluorescence intensity correction method according to the present embodiment, the same result can be obtained as that of the case where the cell simple staining base vector is used, even in the case where there is a possibility that the bead simple staining base vector is lower in accuracy than that of the cell simple staining base vector.

Here, knowledge of how the base vector of the fluorescent dye under consideration changes, in accordance with a fitting process such as described above, is shown in FIGS. 20 and 21 for the example of the fluorescent dyes FITC and PE.

Figure 20:
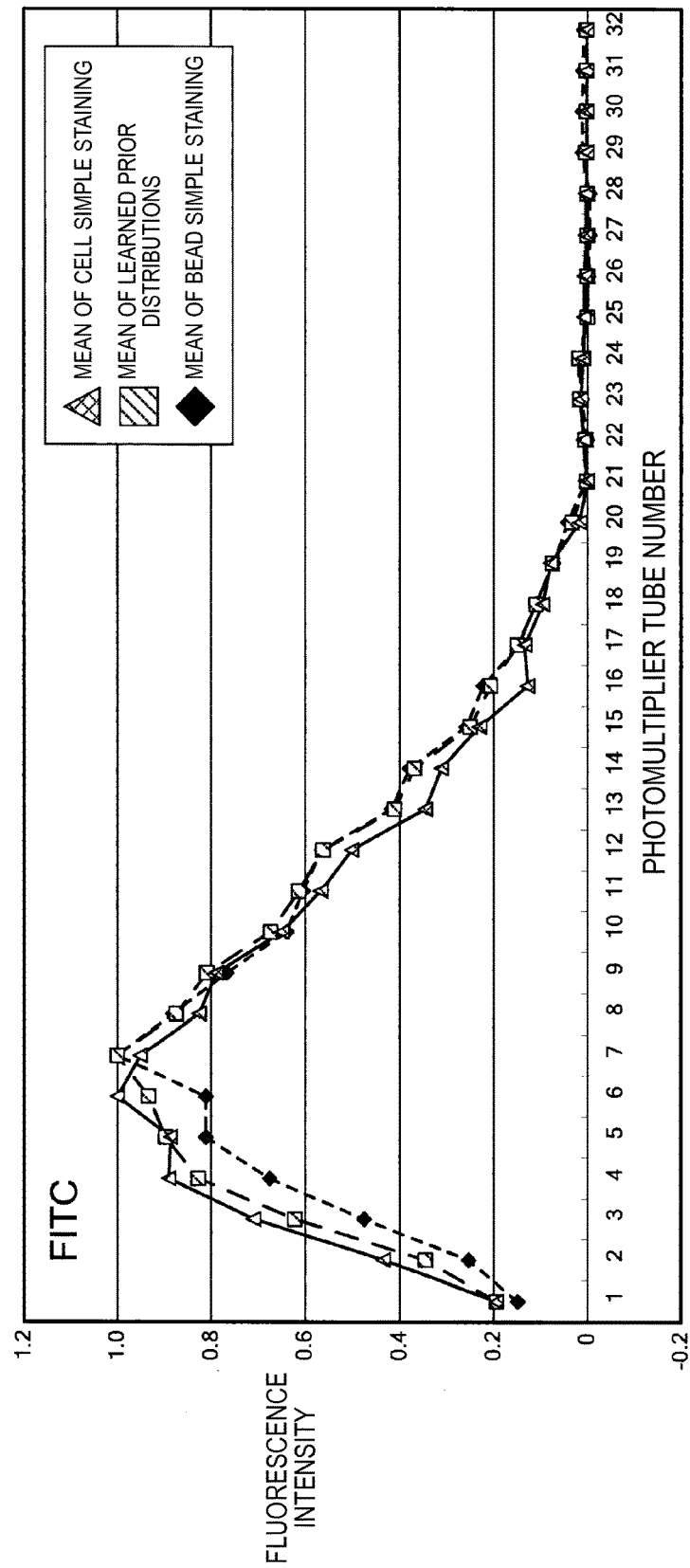
FIG. 20 is a graph chart which shows a change in a base vector of a fluorescent dye FITC.

FIG. 20 is a graph chart which shows the change of the base vector of the fluorescent dye FITC. Further, FIG. 21 is a graph chart which shows the change of the base vector of the fluorescent dye PE.

Figure 21:
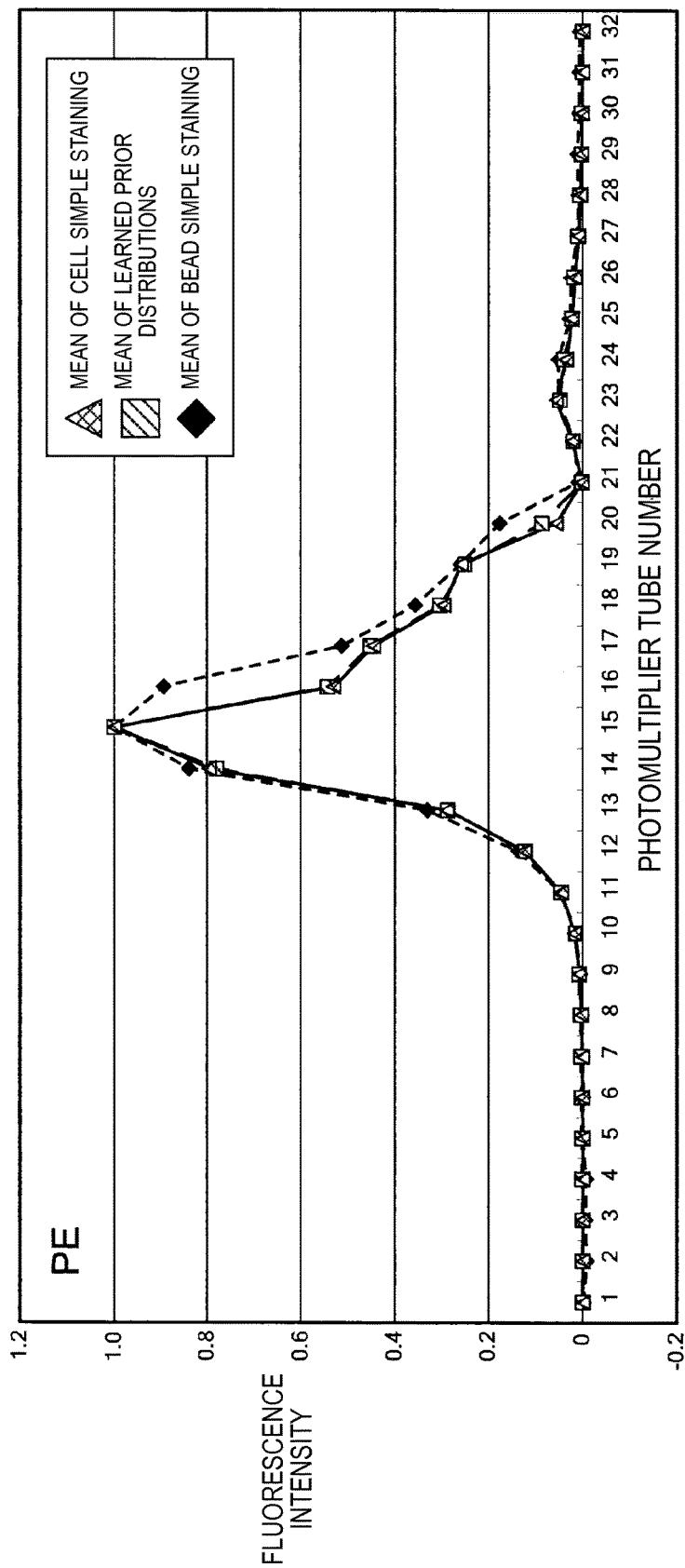
FIG. 21 is a graph chart which shows a change in a base vector of a fluorescent dye PE.

In FIGS. 20 and 21, the plot shown by Δ represents the mean of the cell simple staining base vectors, the plot shown by ♦ represents the mean of the bead simple staining base vectors, and the plot shown by □ represents the mean of the base vectors (that is, the prior distributions) estimated by the present proposed method. Since the parameters which represent the prior distribution are frequently corrected based on the measurement data or the like, the present proposed method is capable of being seen as the result when the plot shown by □ is learned by the prior distributions so as to be suitable for the measurement data.

As is evident from both FIGS. 20 and 21, it can be understood that the mean of the prior distributions, in which the measurement data is learned by the present proposed method, are distributions which are very similar to the cell simple staining base vector. As is evident from this result, since the prior distributions (base vectors) are learned so as to be suitable for the measurement data, it can be understood that a result which is very similar to the cell simple staining base vector can be obtained in the present proposed method, even when the intensity correction process is started by setting the bead simple staining base vector as an initial value.

To continue, two-dimensional correlation diagrams generated by the restricted least square method and the present proposed method, by using the cell simple staining prior distributions, will be described with reference to FIG. 22. FIG. 22 is a graph chart which shows two-dimensional correlation diagrams for the above described mixed sample, which use the cell simple staining prior distributions and are generated by the restricted least square method and the present proposed method. Here, the two-dimensional correlation diagrams shown in FIG. 22 are diagrams in which the fluorescence intensities of two types of fluorescent dyes selected from three types of fluorescent dyes (FITC, Alexa 532, and PE) are plotted on a logarithmic scale.

When referring to FIG. 22, it can be understood that very similar groups (populations) in the restricted least square method and the present proposed method are shown for the two-dimensional correlation diagrams in which the fluorescence intensity of FITC and the fluorescence intensity of PE are plotted, and for the two-dimensional correlation diagrams in which the fluorescence intensity of FITC and the fluorescence intensity of Alexa 532 are plotted.

However, in the two-dimensional correlation diagrams (the corrected diagrams shown on the right side) in which the fluorescence intensities of PE and the fluorescence intensity of Alexa 532 are plotted, it can be understood that the behaviors of the displayed groups are different in the restricted least square method and the present proposed method for the regions surrounded by a dotted line in the figures. More specifically, in the two-dimensional correlation diagram generated by using the restricted least square method, the region surrounded by the dotted line in the figure appears as a single large group connected in the portion represented by an arrow in the figure. Further, in the two-dimensional correlation diagram generated by using the present proposed method, there are two groups present in the region surrounded by the dotted line in the figure.

Figure 23:
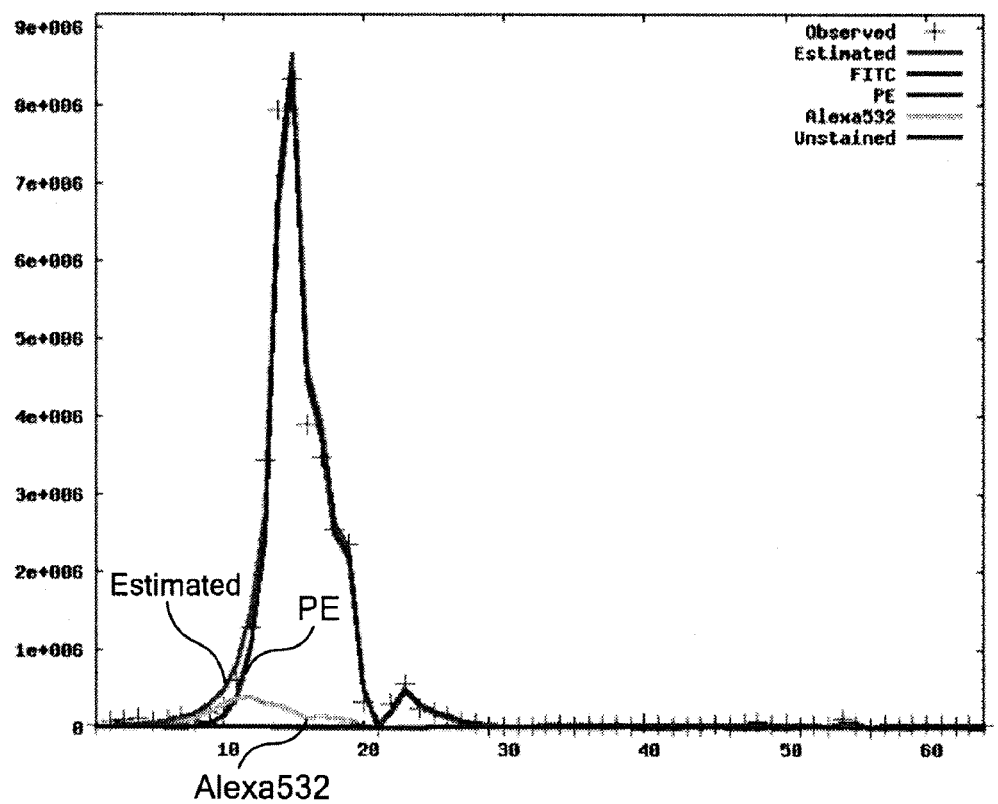
FIG. 23 is a graph chart which shows a fitting result of the measurement data by a restricted least square method.
Figure 24:
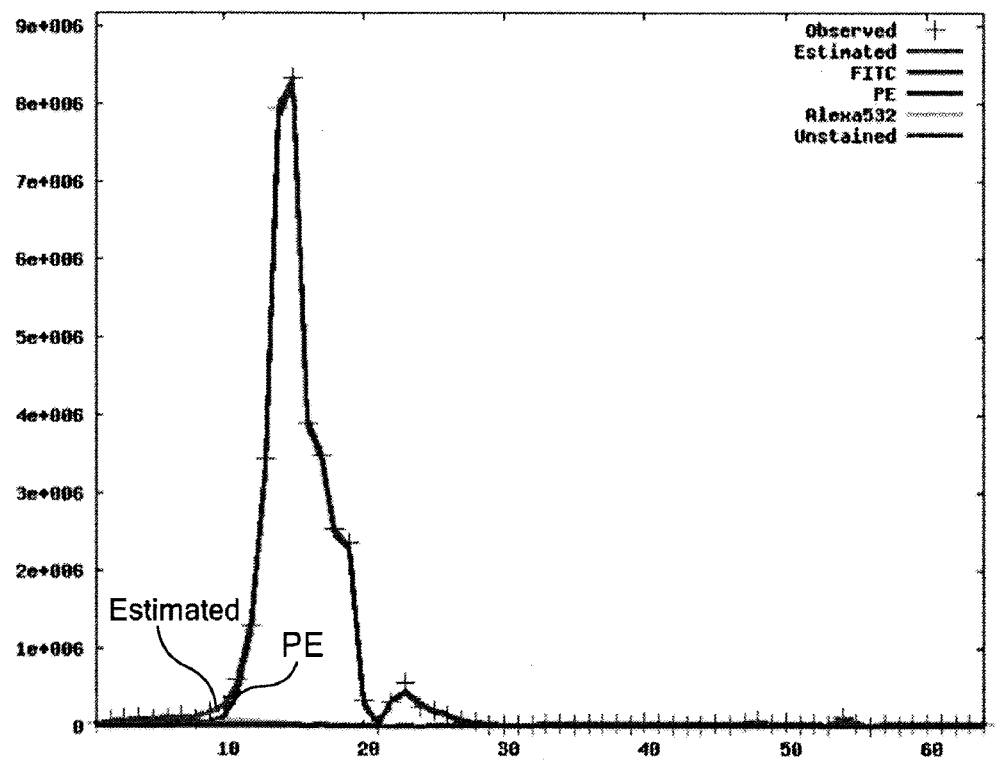
FIG. 24 is a graph chart which shows a fitting result of the measurement data in the case where a cell simple staining base vector is used.

The fitting result of the portion shown by the arrow in FIG. 22(a) is shown in FIG. 23, and the fitting result of the portion shown by the arrow in FIG. 22(b) is shown in FIG. 24. When observing FIG. 23, it can be understood that the measurement data of this portion is fitted by using the base vectors of the fluorescent dyes PE and Alexa 532. In this way, since there is room for accuracy of the fitting using the base vector of the fluorescent dye PE, it can be considered that the fluorescence intensity of the fluorescent dye Alexa 532 may leak into the fluorescence intensity of the fluorescent dye PE, and as a result the single large group such as shown in FIG. 22(a) may be formed.

Further, since a process which estimates the base vector of the fluorescent dye PE is performed in the fitting result by the present proposed method shown in FIG. 24, the measurement data of this portion is fitted by using the base vector of the fluorescent dye PE (and without using the base vector of the fluorescent dye Alexa 532). In this way, it is suggested that the leakage of the fluorescence intensity, which has occurred in the restricted least square method, is appropriately corrected in the present proposed method, and the two groups such as shown in FIG. 22(b) are shown in the two-dimensional correction diagram.

To continue, two-dimensional correlation diagrams generated by the restricted least square method and the present proposed method, by using the bead simple staining prior distributions, will be described with reference to FIG. 25. FIG. 25 is a graph chart which shows two-dimensional correlation diagrams for the above described mixed sample, which use the bead simple staining prior distributions and are generated by the restricted least square method and the present proposed method. Here, the two-dimensional correction diagrams shown in FIG. 25 are diagrams in which the fluorescence intensities of two types of fluorescent dyes selected from three types of fluorescent dyes (FITC, Alexa 532, and PE) are plotted on a logarithmic scale.

In FIG. 25, a plurality of groups estimated from the distributions of the plots are segmented in each two-dimensional correlation diagram, and the boundaries of each group are represented by solid lines. Further, a number written in each region represents the number of plots included in each region, and a number written in parentheses represents the difference in the number of plots from the case where the cell simple staining prior distributions are used.

As is evident from the two-dimensional correlation diagrams shown on the right side of FIG. 25, it can be understood that the leakage of fluorescence intensity, which has occurred in the restricted least square method, is appropriately corrected by the present proposed method, even in the case where the bead simple staining prior distributions are used. Further, when comparing the three types of two-dimensional correlation diagrams, it can be understood that the difference in the number of plots from that of the cell simple staining prior distributions is large for the two dimensional correction diagrams by the restricted least square method, while in contrast the difference in the number of plots from that of the cell simple staining prior distributions is very small for the present proposed method. From this result, it is shown that a similar result to that of the cell simple staining prior distribution can be obtained by using the intensity correction method by the present proposed method, by setting the bead simple staining prior distributions as starting points, and by performing learning by the measurement data.

Figure 26:
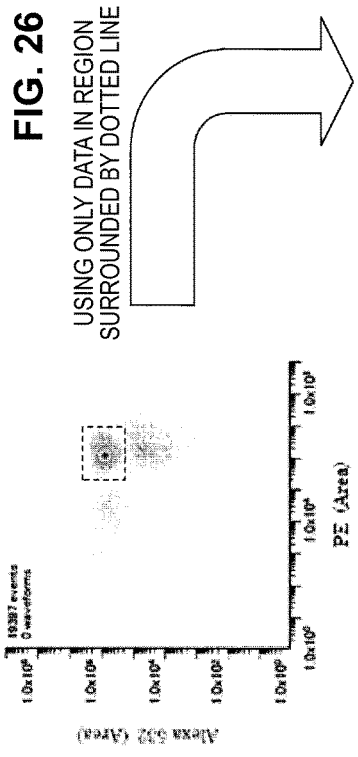
FIG. 26 is an explanatory diagram which shows a learning result of prior distributions using part of the measurement data.

FIG. 26 is an explanatory diagram which shows the learning result of the prior distributions using one part of the measurement data. In the example shown in FIG. 26, a result is shown which verifies whether or not the prior distributions can be appropriately learned, by using only the measurement data corresponding to the groups present in the upper right portion of the two-dimensional correlation diagram. As is evident from the graph chart shown in FIG. 26, the mean of the prior distributions learned from only the data of the region surrounded by a dotted line is more similar to the mean of the cell simple staining prior distributions than that of the mean of the bead simple staining prior distributions. From this result, it becomes evident that the prior distributions can be appropriately learned, even if the learning is performed using only part of the measurement data, by using the present proposed method.

As is evident from the example described above, since the fluorescence characteristics of each fluorescent dye are estimated for each measurement in the above described intensity correction method, the leakage of the problematic fluorescence intensity can be corrected with fluorescence correction by the restricted least square method.

Further, in the intensity correction method according to the present embodiment, since prior knowledge (for example, measurement data or the like of each fluorescent dye obtained by prior measurements) related to the fluorescence characteristics of each fluorescent dye can be corrected in accordance with the measurement data of the sample, it becomes possible to obtain an intensity correction result with high accuracy, even in the case where prior knowledge, in which there is room for accuracy, is set as an initial value.

2-5: Masking Process

As described above, by applying the intensity correction method according to the present embodiment, an intensity correction result can be obtained with higher accuracy. However, in order to further improve the accuracy, it may be necessary to consider the influence of noise originating from the autofluorescence of a cell or from the apparatus (hereinafter, called noise or the like).

Usually, a dye emits fluorescence in a specific frequency band and does not emit fluorescence in the other frequency bands. However, there are times when the fluorescence intensity is observed in frequency bands other than the specific frequency band. This means that noise originating from the autofluorescence of a cell or from the apparatus is observed, similar to when measuring an unstaining sample. Therefore, even if the observation results of microparticles singly labeled by some dye are used as base vectors, there are times where the application of these base vectors may occur in the observation results of samples not including this dye, due to the influence of noise or the like. As a result, there is a concern that an adverse influence may be exerted on the fluorescence correction.

Accordingly, a technique (hereinafter, called the present technique) is conceived in the present embodiment which does not consider the fluorescence of a dye in a region where the dye does not shine (the value of the base vector is set to 0). Hereinafter, not considering (the value of the base vector is set to 0) some channel (frequency) will be called "applying a mask" to this channel. Further, hereinafter, a specific method will be referred to which decides the channels to which to apply a mask.

Specifically, a technique is proposed which performs a t-test for unstaining observation data and simple staining observation data in each channel, and a mask is applied if a hypothesis (null hypothesis) of "no difference" is not rejected under a set level of significance p, and a mask is not applied if the hypothesis is rejected. Further, in the case where the simple staining observation data includes stained cells and unstained cells, the simple staining observation data is clustered into an unstaining cluster and a simple staining cluster, and a t-test is performed for the observation data allocated to the simple staining cluster and the unstaining observation data.

By such a configuration, it becomes possible to appropriately eliminate the influence of noise or the like originating from the autofluorescence of a cell or from the apparatus, and it becomes possible to perform fluorescence correction so that an intended spectrum component can be extracted with higher accuracy. Note that while a description is carried forward hereinafter in accordance with an example in which the fluorescence intensity of a masked channel is set to 0, a method can also be considered which fixes the fluorescence intensity of a masked channel at a small value without being set to 0. Further, while a description is carried forward which includes a t-test as an example of the testing technique, it is also possible to use a statistical testing technique other than that of a t-test.

Figure 27:
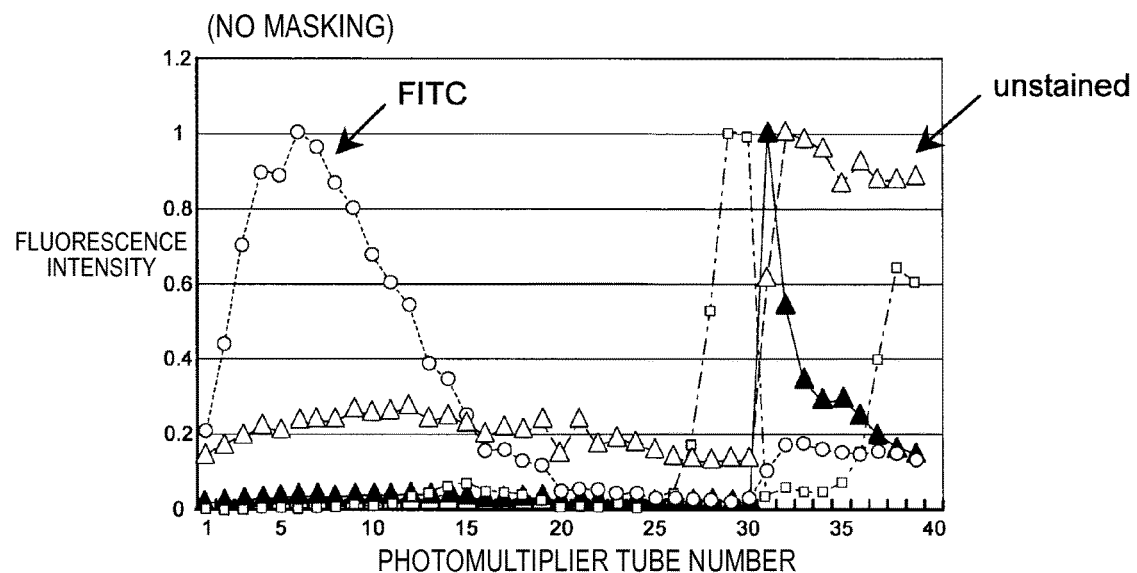
FIG. 27 is an explanatory diagram which shows the fluorescence characteristics of fluorescent dyes used to stain a mixed sample.
Figure 28:
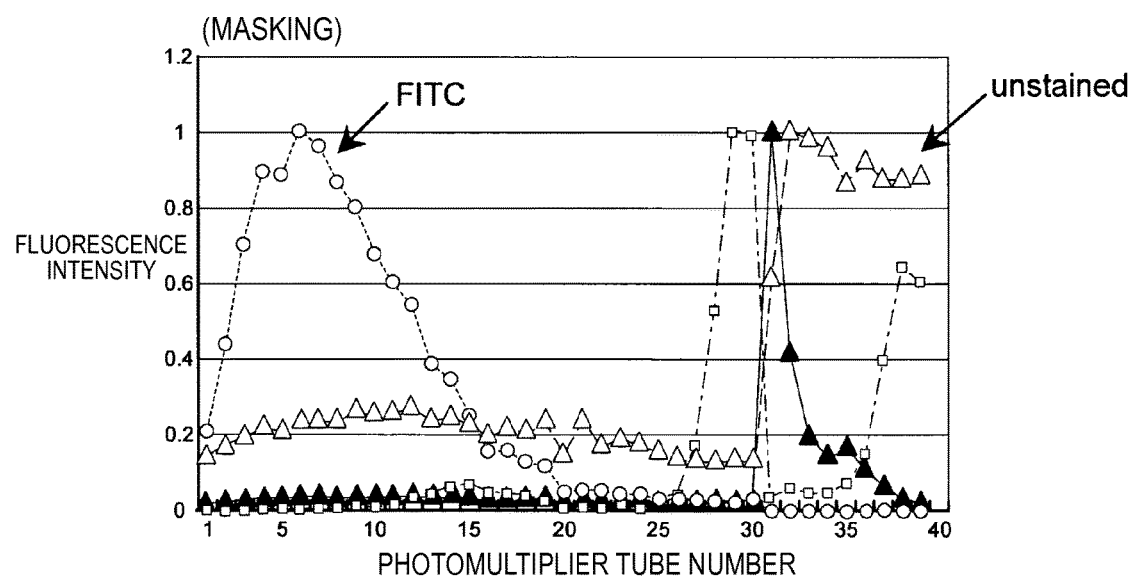
FIG. 28 is a graph chart which shows the fluorescence characteristics of fluorescent dyes used to stain a mixed sample.

First, FIGS. 27 and 28 will be referred to. The graph including "unstained" in the figures shows the result of measuring unstained microparticles. While the results of measuring microparticles stained with FITC, PE-Cy7, and APC are also shown in addition to the results of unstained microparticles, here attention will be paid to the unstained and the FITC measurement results.

As shown in FIG. 27, there is a tendency shown in the unstained graph towards a fluorescence intensity which is high for the number of photomultipliers tubes in the range of 30-39. Turning our eyes to the FITC graph, the FITC graph shows a characteristic of fluorescence intensity such that a peaked curve is drawn for the number of photomultiplier tubes in the range of 1-20. Further, there is a tendency shown in the FITC graph shown in FIG. 27 towards a fluorescence intensity which is somewhat high for the number of photomultiplier tubes in the range of 30-39.

However, it is expected that FITC originally has no fluorescence characteristics in the frequency band corresponding to the range of photomultiplier tube numbers 30-39. Therefore, the characteristics shown by the FITC graph in this range can be considered to be caused by the influence of noise or the like. When considering such an influence of noise or the like, there is the possibility that the base vector of FITC will be applied by mistake, as the base vector which expresses a measurement result having fluorescence intensity, to the frequency bands to which the fluorescence from the FITC is not obtained.

Accordingly, for example, a method (hereinafter, called a masking process) is proposed which fixes the fluorescence intensity of the frequency bands to which FITC does not emit fluorescence to 0 or a sufficiently small value. When applying this method, as shown in FIG. 28, the fluorescence intensity of FITC in the range of photomultiplier tube numbers 30-39 is suppressed, and the base vector of FITC being applied by mistake to the frequency bands corresponding to this range can be avoided. Needless to say, the result is similar for other staining materials, such as PE-Cy7 or APC.

A method, for example, which maintains a table (refer to FIGS. 29 and 30) for setting whether or not a mask is applied for each channel, and estimates the channels to which the masking process will be applied based on this table, can be considered as a specific method of a masking process. In the examples of FIGS. 29 and 30, a channel to which a masking process is not applied is expressed as "1", and a channel to which a masking process is applied is expressed as "0". Note that the example of FIGS. 29 and 30 shows the suitability of a masking process applied to the measurement results of FITC, PE-Cy7, and APC.

Figure 33:
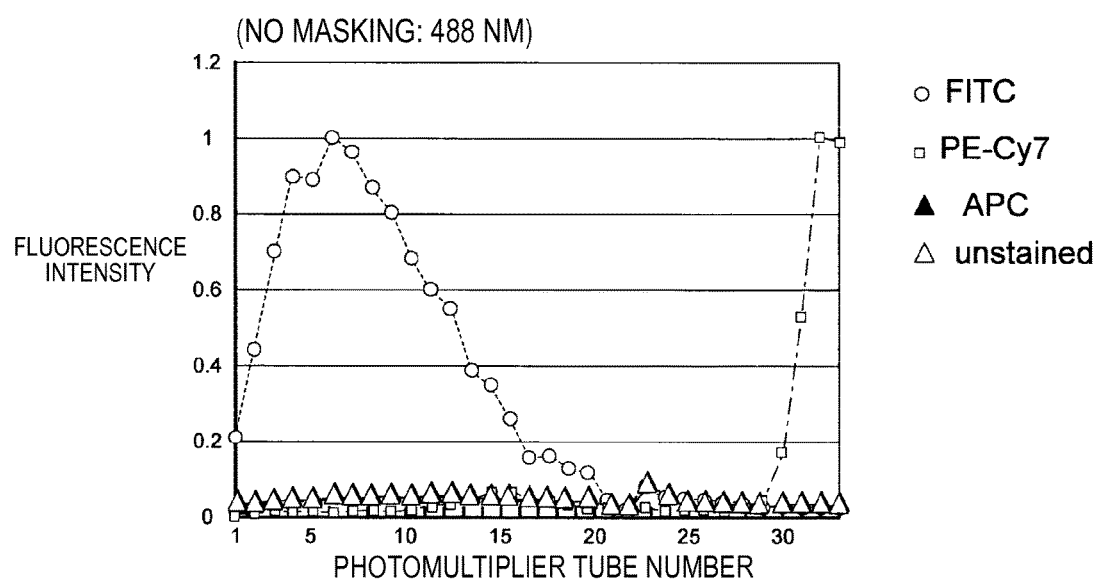
FIG. 33 is a graph chart which shows fluorescence characteristics (no masking) of fluorescent dyes used to stain a mixed sample.
Figure 34:
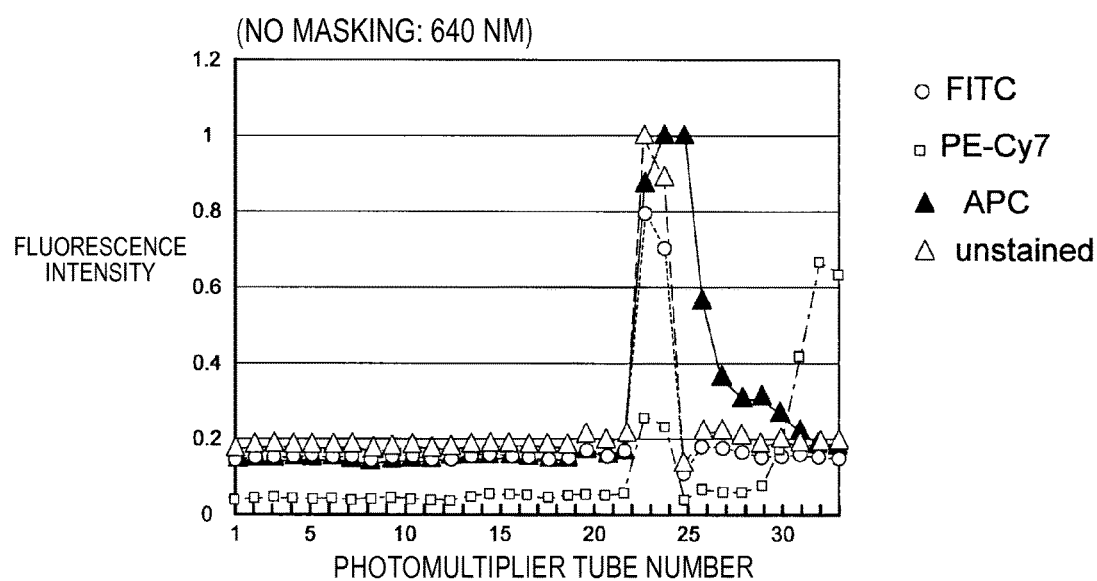
FIG. 34 is a graph chart which shows fluorescence characteristics (no masking) of fluorescent dyes used to stain a mixed sample.

The example of FIGS. 29 and 30 shows settings in which a masking process is not applied to all the channels. In this case, a detection result of fluorescence intensity can be obtained, such as shown in FIGS. 31 and 33, for FIG. 29. Similarly, a detection result of fluorescence intensity can be obtained, such as shown in FIGS. 32 and 34, for FIG. 30. While it is somewhat difficult to understand from the example of FIG. 33, in which the excitation wavelength is set to 488 nm, it can be understood from the example of FIG. 34, in which the excitation wavelength is set to 640 nm, that each of FITC, PE-Cy7, and APC are considerably affected by noise or the like. In such a case, there is a concern that an adverse influence may be applied to the intensity correction result.

Accordingly, as shown in FIGS. 35 and 36, the channels corresponding to the frequency bands in which fluorescence is not emitted, for each of FITC, PE-Cy7, and APC, are masked. As shown in FIG. 35, in the case of an excitation wavelength of 488 nm, FITC has almost no fluorescence characteristics in channels 19-32. Further, PE-Cy7 has almost no fluorescence characteristics in channels 1-12 and 17-27. In addition, APC has almost no fluorescence characteristics in channels 1-32. Accordingly, settings are made so as to apply a masking process for these channels.

Similarly, as shown in FIG. 36, in the case of an excitation wavelength of 640 nm, FITC has almost no fluorescence characteristics in channels 1-32. Further, PE-Cy7 has almost no fluorescence characteristics in channels 1-28. In addition, APC has almost no fluorescence characteristics in channels 1-23 and 27-32. Accordingly, settings are made so as to apply a masking process to these channels.

Figure 39:
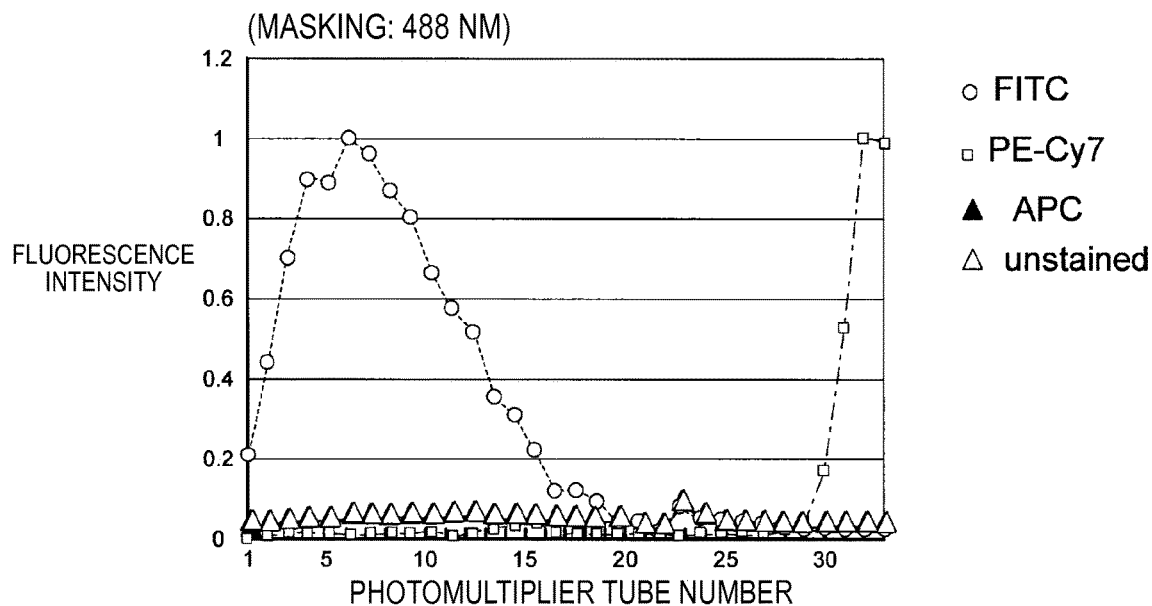
FIG. 39 is a graph chart which shows fluorescence characteristics (masking) of fluorescent dyes used to stain a mixed sample.
Figure 40:
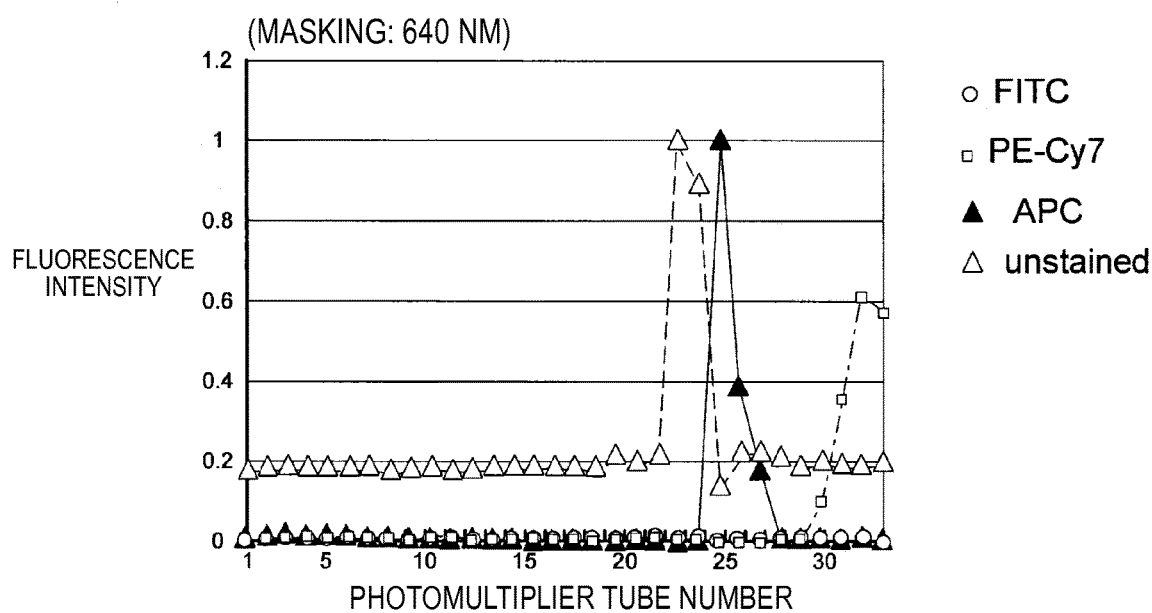
FIG. 40 is a graph chart which shows fluorescence characteristics (masking) of fluorescent dyes used to stain a mixed sample.

As a result, a mean waveform by performing simple staining for each dye, such as shown in FIG. 37, is obtained for the excitation wavelength of 488 nm. Similarly, a mean waveform by performing simple staining for each dye, such as shown in FIG. 38, is obtained for the excitation wavelength of 640 nm. The data of FIG. 37, when plotted, will become that such as shown in FIG. 39. Similarly, the data of FIG. 37, when plotted, will become that such as shown in FIG. 40. In this way, by applying a masking process, it becomes possible to suppress the fluorescence intensity of wavelength regions which do not originally have fluorescence characteristics, and it becomes possible to avoid an occurrence of the application of an incorrect base vector.

Here, the effect of a masking process will be confirmed for a two-dimensional correlation diagram related to the fluorescence intensity of FITC and the fluorescence intensity of PE-Cy7, a two-dimensional correlation diagram related to the fluorescence intensity of FITC and the fluorescence intensity of APC, and a two-dimensional correlation diagram related to the fluorescence intensity of PE-Cy7 and the fluorescence intensity of APC.

Figure 41:
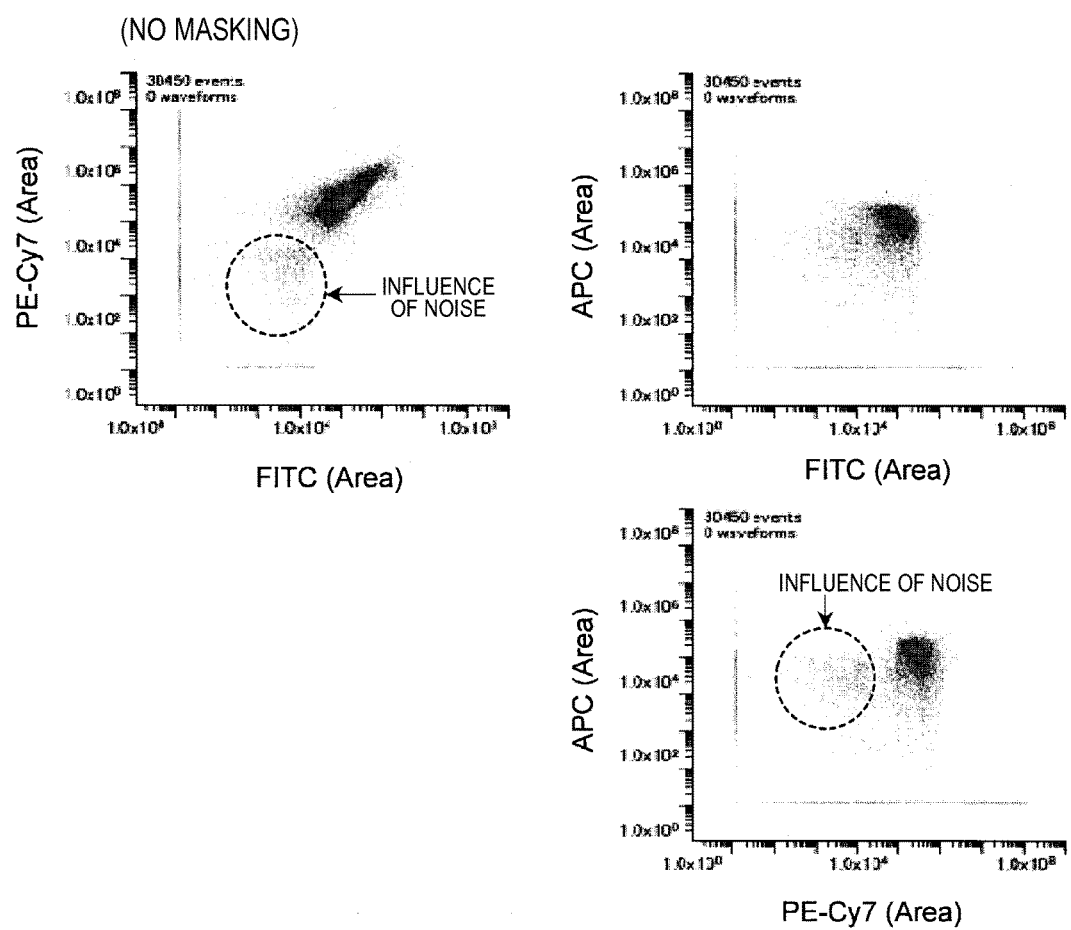
FIG. 41 is a graph chart which shows a two-dimensional correlation diagram (no masking) of a mixed sample.

First, FIG. 41 will be referred to. The two-dimensional correlation diagrams of FIG. 41 show calculation results in the case where a masking process is not applied. A group is detected in the bottom left portion, within the two-dimensional correlation diagram shown in FIG. 41 of the fluorescence intensity of FITC and the fluorescence intensity of PE-Cy7, which can be considered to be an influence of noise or the like. In addition, a group is detected in the center left portion, within the two-dimensional correlation diagram of the fluorescence intensity of PE-Cy7 and the fluorescence intensity of APC, which can be considered to be an influence of noise or the like.

Figure 42:
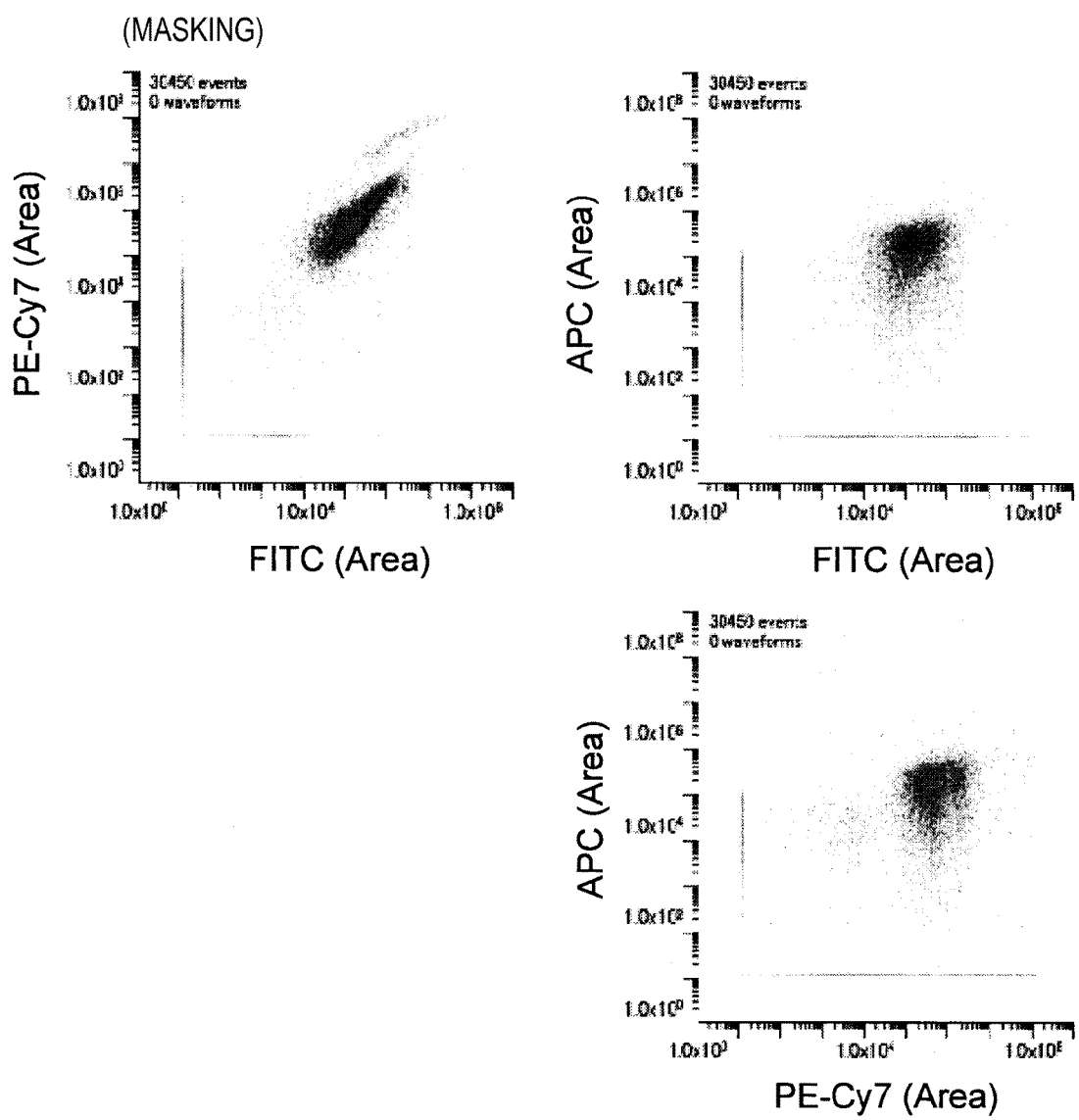
FIG. 42 is a graph chart which shows a two-dimensional correlation diagram (masking) of a mixed sample.

Next, FIG. 42 will be referred to. The two-dimensional correlation diagrams of FIG. 42 show calculation results in the case where a masking process is applied. When referring to FIG. 42 and comparing with FIG. 41, while, a group (population) is detected in the bottom left portion, within the two-dimensional correlation diagram of the fluorescence intensity of FITC and the fluorescence intensity of PE-Cy7, which can be considered to be an influence of noise or the like, the group which causes an influence of noise or the like has almost completely disappeared in FIG. 42. In addition, while a group is detected in the center left portion, within the two-dimensional correlation diagram of the fluorescence intensity of PE-Cy7 and the fluorescence intensity of APC, which can be considered to be an influence of noise or the like, the group which causes an influence of noise or the like is significantly diminished in FIG. 42.

From such a result, by applying a masking process which takes into consideration the fluorescence characteristics for each dye, it becomes difficult for an occurrence of the application of an incorrect base vector, and it can be considered that the correction accuracy of the fluorescence intensity can be improved. A method which sets a table, such as shown in FIGS. 35 and 36, based on a user's experience, for example, may be a selection method of the channels to which a masking process is applied. However, since the burden is large for constructing the table manually for each type of sample and dye, a method has been proposed which determines the suitability of an automatic masking process by using a statistical test such as that described below.

Further, a method can be considered which compares data in which unstained microparticles are observed (hereinafter, called unstaining data) with data in which simple staining microparticles are observed (hereinafter, called simple staining data) for each channel, and in the case where the mean of the simple staining data significantly exceeds the mean of the unstaining data, does not apply a masking process for this channel. That is, a method can be considered which performs statistical testing, and applies a masking process in the case where a null hypothesis of "no difference" is not rejected for both, and does not apply a masking process in the case where the null hypothesis is rejected.

For example, the intensity correction processing section 103 executes a t-test for unstaining data and simple staining data for each channel, and determines whether or not a hypothesis of "no difference" is rejected under a set level of significance p. Then, the intensity correction processing section 103 is set so as to not apply a masking process to the simple staining data which corresponds to a channel corresponding to the case where the hypothesis is rejected, and to apply a masking process to the simple staining data which corresponds to a channel corresponding to the case where the hypothesis is not rejected. By such a configuration, a table, such as shown in FIGS. 35 and 36, is automatically constructed.

Further, when obtaining simple staining data, in the case where stained microparticles and unstained microparticles are included in an observation target, the intensity correction processing section 103 performs clustering in advance which separates an undyed cluster from a simple staining cluster. Then, after performing clustering, the intensity correction processing section 103 executes a t-test for both the simple staining data observed for the simple staining cluster, and the unstaining data observed for the unstaining cluster. By such a configuration, a setting of an automatic and appropriate masking process is achieved, even if unstained microparticles or insufficiently stained microparticles are included in an observation target.

Heretofore, a setting method of a masking process and a masking process target has been described. By such a configuration, a channel to which a masking process is to be applied is automatically determined by a statistical testing technique, and a channel to which an influence of noise or the like is to be removed is appropriately masked. As a result, the chance of an occurrence of the application of an incorrect base vector is suppressed, and the correction accuracy of the fluorescence intensity is improved.

3: EXAMPLE HARDWARE CONFIGURATION

Figure 43:
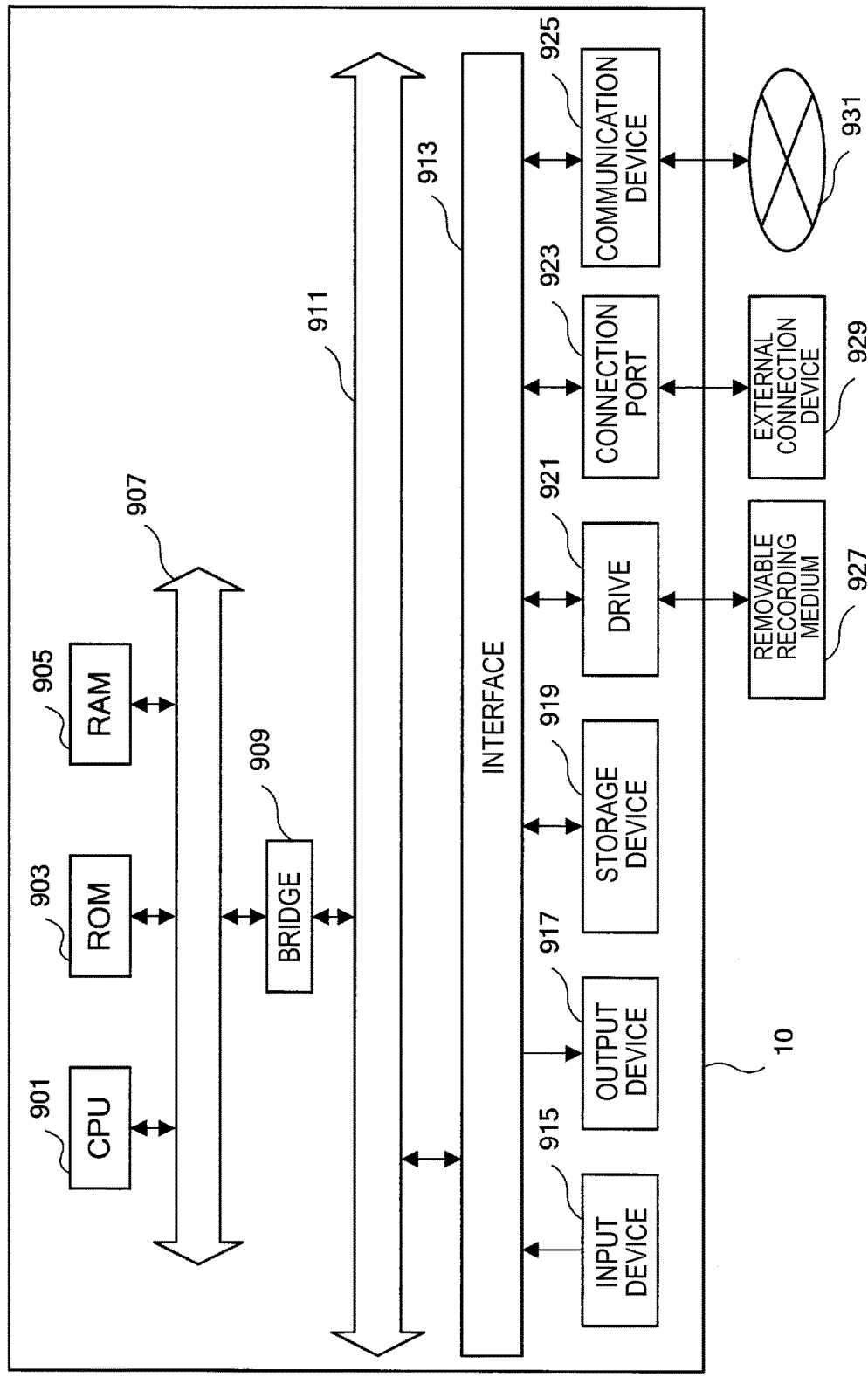
FIG. 43 is a block diagram which shows a hardware configuration of the information processing apparatus according to the embodiments of the present disclosure.

Next, a hardware configuration of the information processing apparatus 10 according to an embodiment of the present disclosure will be described in detail with reference to FIG. 43. FIG. 43 is a block diagram illustrating the hardware configuration of the information processing apparatus 10 according to the embodiment of the present disclosure.

The information processing apparatus 10 mainly includes a CPU 901, a ROM 903, and a RAM 905. The information processing apparatus 10 further includes a host bus 907, a bridge 909, an external bus 911, an interface 913, an input device 915, an output device 917, a storage device 919, a drive 921, a connection port 923, and a communication device 925.

The CPU 901 serves as an arithmetic processing device and a control device. Thus, the CPU 901 controls all or some of operations of the information processing apparatus 10 in accordance with various programs stored in the ROM 903, the RAM 905, the storage device 919, or a removable recording medium 927. The ROM 903 stores programs, arithmetic parameters, or the like used by the CPU 901. The RAM 905 temporarily stores the programs used by the CPU 901 or parameters or the like appropriately changed in execution of the programs. The CPU, the RAM, and the ROM are connected to each other by a host bus 907 configured by an internal bus such as a CPU bus.

The host bus 907 is connected to an external bus 911 such as a peripheral component interconnect/interface (PCI) bus via the bridge 909.

The input device 915 is an operation unit operated by a user, such as a mouse, a keyboard, a touch panel, a button, a switch, or a lever. For example, the input device 915 may be a remote control unit (so-called remote controller) using infrared rays or other radio waves or may be an external connection device 929 such as a portable telephone or a PDA responding to an operation of the information processing apparatus 10. For example, the input device 915 is configured by an input control circuit or the like that generates an input signal based on information input by the user and outputs the generated input signal to the CPU 901. The user of the information processing apparatus 10 can operate the input device 915 to input various kinds of data or give processing instructions to the information processing apparatus 10.

The output device 917 is configured by a device that is capable of visually or audibly notifying a user of acquired information. Examples of the device include display devices such as CRT display devices, liquid crystal display devices, plasma display devices, EL display devices, or lamps, audio output devices such as speakers and headphones, printer devices, portable telephones, and facsimiles. For example, the output device 917 outputs results obtained through various processes of the information processing apparatus 10. Specifically, a display device displays the results obtained through the various processes of the information processing apparatus 10 in the forms of text or images. On the other hand, an audio output device converts an audio signal formed by reproduced audio data or acoustic data into an analog signal and outputs the converted analog signal.

The storage device 919 is a data storing device which is configured as an example of the storage unit of the information processing apparatus 10. The storage device 919 is configured by, for example, a magnetic storage device such as a hard disk drive (HDD), a semiconductor storage device, an optical storage device, or a magneto-optical storage device. The storage device 919 stores the programs or various kinds of data to be executed by the CPU 901 and various kinds of data acquired from the outside.

The drive 921 is a reader and writer for a storage medium and is included in or attached externally to the information processing apparatus 10. The drive 921 reads information stored in the removable recording medium 927 such as a magnetic disk, an optical disc, a magneto-optical disc, or a semiconductor memory mounted on the information processing apparatus and outputs the read information to the RAM 905. Further, the drive 921 can also write information on the removable recording medium 927 such as a magnetic disk, an optical disc, a magneto-optical disc, or a semiconductor memory mounted on the information processing apparatus. Examples of the removable recording medium 927 include a DVD medium, an HD-DVD medium, and a Blu-ray medium. The removable recording medium 927 may be a CompactFlash (registered trademark) (CF), a flash memory, a secure digital (SD) memory card, or the like. Further, the removable recording medium 927 may be an integrated circuit (IC) card or an electronic apparatus on which a non-contact type IC chip is mounted.

The connection port 923 is a port that directly connects an apparatus to the information processing apparatus 10. Examples of the connection port 923 include a universal serial bus (USB) port, an IEEE1394 port, and a small computer system interface (SCSI) port. Other examples of the connection port 923 include an RS-232C port, an optical audio terminal, and a high-definition multimedia interface (HDMI) port. When the external connection device 929 is connected to the connection port 923, the information processing apparatus 10 directly acquires various kinds of data from the external connection device 929 or provides various kinds of data to the external connection device 929.

For example, the communication device 925 is a communication interface configured by a communication device connected to a communication network 931. Examples of the communication device 925 include a wired or wireless local area network (LAN), Bluetooth (registered trademark), and a communication card for a wireless USB (WUSB). The communication device 925 may be an optical communication router, an asymmetric digital subscriber line (ADSL) router, or modems for various communications. For example, the communication device 925 can transmit or receive a signal or the like to or from the Internet or another communication device in conformity with a predetermined protocol such as TCP/IP. The communication network 931 connected to the communication device 925 is configured by networks connected to each other in a wireless or wired manner. For example, the communication network 931 may be the Internet, a household LAN, infrared communication, radio wave communication, or satellite communication.

An example of the hardware configuration capable of realizing the functions of the information processing apparatus 10 according to the embodiment of the present disclosure has been described above. Each constituent element described above may be configured by a general member or may be configured by hardware specialized in the function of each constituent element. Accordingly, the hardware configuration to be used can be modified appropriately in accordance with a technical level when this embodiment is realized.

4: CONCLUSION

Additionally, the present technology may also be configured as below.

(1) An information processing apparatus, including:
a testing section which performs statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band;
a masking processing section which sets, in a case where there is no significant difference between the simple staining data and the unstaining data for the frequency band, the simple staining data to 0 or a prescribed value; and
an estimation section which estimates, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

(2) The information processing apparatus according to (1),
wherein the estimation section models the base vectors in a manner that the base vectors occur in accordance with a prescribed probability distribution, and estimates the combination coefficient by using the base vectors estimated from the simple staining data.

(3) The information processing apparatus according to (1) or (2),
wherein the testing section determines, by a t-test, whether or not a null hypothesis that there is no difference between the simple staining data and the unstaining data is rejected under a prescribed significance level p.

(4) The information processing apparatus according to any one of (1) to (3), further including:
a clustering section which clusters, in a case where an unstained particle and a particle subjected to simple staining are included in a sample subjected to fluorescence measurement, an unstaining cluster including the unstained particle and a simple staining cluster including the particle subjected to simple staining,
wherein the testing section performs the statistical testing by using observation data corresponding to the unstaining cluster as the unstaining data and observation data corresponding to the simple staining cluster as the simple staining data.

(5) The information processing apparatus according to (2),
wherein the estimation section models an intensity component of light other than fluorescence emitted from the staining material in a manner that the intensity component occurs in accordance with another prescribed probability distribution different from the prescribed probability distribution, and estimates the combination coefficient by using the base vectors estimated from the simple staining data.

(6) The information processing apparatus according to any one of (1) to (5),
wherein the staining material is a fluorescent dye.

(7) An information processing method, including:
performing statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band;
setting, in a case where there is no significant difference between the simple staining data and the unstaining data for the frequency band, the simple staining data to 0 or a prescribed value; and
estimating, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

(8) A program for causing a computer to implement:
a testing function which performs statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band;
a masking processing function which sets, in a case where there is no significant difference between the simple staining data and the unstaining data for the frequency band, the simple staining data to 0 or a prescribed value; and
an estimation function which estimates, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

(9) A computer-readable recording medium having a program recorded thereon, the program causing a computer to implement:
a testing function which performs statistical testing on simple staining data obtained by performing fluorescence measurement on a particle subjected to simple staining with a staining material having a prescribed fluorescence characteristic and unstaining data obtained by performing fluorescence measurement on an unstained particle for comparison for a frequency band;

a masking processing function which sets, in a case where there is no significant difference between the simple staining data and the unstaining data for the frequency band, the simple staining data to 0 or a prescribed value; and an estimation function which estimates, in a manner that double staining data obtained by performing fluorescence measurement on a particle stained with a plurality of staining materials is represented by a linear combination of base vectors representing a distribution of the simple staining data corresponding to each staining material, a combination coefficient of the linear combination.

REMARKS

The above described intensity correction processing section 103 is an example of a detection section, a masking processing section, an estimation section, and a clustering section.

It should be understood by those skilled in the art that various modifications, combinations, sub-combinations and alterations may occur depending on design requirements and other factors insofar as they are within the scope of the appended claims or the equivalents thereof.

The present disclosure contains subject matter related to that disclosed in Japanese Priority Patent Application JP 2012-122161 filed in the Japan Patent Office on May 29, 2012, the entire content of which is hereby incorporated by reference.

What is claimed is:

1. An information processing apparatus, comprising:
a processor; and
at least one non-transitory computer-readable storage medium storing processor-executable instructions that, when executed by the processor, cause the processor to:
compare, by performing statistical testing, a spectrum of a particle stained with a single fluorescent material to a spectrum of an unstained particle, wherein the spectrum of the particle stained with the single fluorescent material and the spectrum of the unstained particle are obtained by measuring fluorescence intensities over a first plurality of frequency bands;
identify, from the statistical testing, a frequency band of the first plurality of frequency bands where a difference between the spectrum of the particle stained with the single fluorescent material and the spectrum of the unstained particle is below a threshold;
generate, from the spectrum of the particle stained with the single fluorescent material, a base vector for the fluorescent material by setting a value of fluorescence intensity for the identified frequency band to 0 or a prescribed value, wherein the base vector includes fluorescence intensity values representative of a spectrum of the fluorescent material over a portion of the first plurality of frequency bands; and
detect a presence of the fluorescent material in a particle stained with a plurality of different staining materials by estimating a linear combination of base vectors, including the generated base vector, for a spectrum of the particle stained with the plurality of different staining materials obtained by measuring fluorescence intensities over a second plurality of frequency bands that include the portion of the first plurality of frequency bands, wherein a combination coefficient of the linear combination is for the generated base vector.

2. The information processing apparatus according to claim 1,
wherein estimating the linear combination includes modeling the base vectors in a manner that the base vectors occur in accordance with a prescribed distribution.

3. The information processing apparatus according to claim 1,
wherein performing statistical testing includes determining, by a t-test, whether or not a null hypothesis that there is no difference between the spectrum of the particle stained with a single fluorescent material and the spectrum of the unstained particle is rejected under a prescribed significance level p.

4. The information processing apparatus according to claim 1, wherein the processor-executable instructions further cause the processor to:
cluster, in a case where the unstained particle and the particle stained with the single fluorescent material are included in a sample subjected to fluorescence measurement, an unstaining cluster including the unstained particle and a simple staining cluster including the particle stained with the single fluorescent material, and
wherein performing the statistical testing includes using observation data corresponding to the unstaining cluster as the spectrum of the unstained particle and observation data corresponding to the simple staining cluster as the spectrum of the particle stained with the single fluorescent material.

5. The information processing apparatus according to claim 2,
wherein estimating the linear combination includes modeling an intensity component of light other than fluorescence emitted from the fluorescent material in a manner that the intensity component occurs in accordance with another prescribed distribution different from the prescribed distribution.

6. The information processing apparatus according to claim 1,
wherein the fluorescent material is a fluorescent dye.

7. The information processing apparatus according to claim 1,
wherein the processor-executable instructions further cause the processor to generate a second base vector that includes fluorescence intensity values representative of a spectrum of a different fluorescent material over a plurality of frequency bands that overlaps with the portion of the first plurality of frequency bands, and
wherein the base vectors used to estimate the linear combination further includes the second base vector.

8. The information processing apparatus according to claim 7,
wherein the processor-executable instructions further cause the processor to detect a presence of the different fluorescent material in the particle stained with the plurality of different staining materials based on a combination coefficient for the second base vector.

9. The information processing apparatus according to claim 1,
wherein the second plurality of frequency bands further includes a plurality of frequency bands that overlaps with a spectrum of a second fluorescent material of the plurality of different staining materials other than the fluorescent material.

10. An information processing method, comprising:

comparing, by performing statistical testing using a processor, a spectrum of a particle stained with a single fluorescent material to a spectrum of an unstained particle, wherein the spectrum of the particle stained with the single fluorescent material and the spectrum of the unstained particle are obtained by measuring fluorescence intensities over a first plurality of frequency bands;

identifying, from the statistical testing, a frequency band of the first plurality of frequency bands where a difference between the spectrum of the particle stained with the single fluorescent material and the spectrum of the unstained particle is below a threshold;

generating, from the spectrum of the particle stained with the single fluorescent material, a base vector for the fluorescent material by setting a value of fluorescence intensity for the identified frequency band to 0 or a prescribed value, wherein the base vector includes fluorescence intensity values representative of a spectrum of the fluorescent material over a portion of the first plurality of frequency bands; and detecting a presence of the fluorescent material in a particle stained with a plurality of different staining materials by estimating a linear combination of base vectors, including the generated base vector, for a spectrum of the particle stained with the plurality of different staining materials obtained by measuring fluorescence intensities over a second plurality of frequency bands that include the portion of the first plurality of frequency bands, wherein a combination coefficient of the linear combination is for the generated base vector.

11. A non-transitory computer-readable storage medium having stored thereon instructions which when executed by a processor implement a method when executed, the method comprising:

comparing, by performing statistical testing, a spectrum of a particle stained with a single fluorescent material to a spectrum of an unstained particle, wherein the spectrum of the particle stained with the single fluorescent material and the spectrum of the unstained particle are obtained by measuring fluorescence intensities over a first plurality of frequency bands;

identifying, from the statistical testing, a frequency band of the first plurality of frequency bands where a difference between the spectrum of the particle stained with the single fluorescent material and the spectrum of the unstained particle is below a threshold;

generating, from the spectrum of the particle stained with the single fluorescent material, a base vector for the fluorescent material by setting a value of fluorescence intensity for the identified frequency band to 0 or a prescribed value, wherein the base vector includes fluorescence intensity values representative of a spectrum of the fluorescent material over a portion of the first plurality of frequency bands; and detecting a presence of the fluorescent material in a particle stained with a plurality of different staining materials by estimating a linear combination of base vectors, including the generated base vector, for a spectrum of the particle stained with the plurality of different staining materials obtained by measuring fluorescence intensities over a second plurality of frequency bands that include the portion of the first plurality of frequency bands, wherein a combination coefficient of the linear combination is for the generated base vector.

* * * * *